(12) United States Patent
Rose et al.

(10) Patent No.: US 8,298,830 B2
(45) Date of Patent: *Oct. 30, 2012

(54) ORGANIC MATERIALS ABLE TO DETECT ANALYTES

(75) Inventors: Aimee Rose, Cambridge, MA (US); Timothy M. Swager, Newton, MA (US); Zhengguo Zhu, Chelmsford, MA (US); Vladimir Bulovic, Lexington, MA (US); Conor Francis Madigan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/795,279

(22) Filed: Jun. 7, 2010

(65) Prior Publication Data

US 2010/0310424 A1    Dec. 9, 2010

Related U.S. Application Data

(63) Continuation of application No. 11/005,631, filed on Dec. 6, 2004, now Pat. No. 7,759,127.

(60) Provisional application No. 60/527,395, filed on Dec. 5, 2003.

(51) Int. Cl.
    *G01N 33/00* (2006.01)
(52) U.S. Cl. ........................................................ 436/164
(58) Field of Classification Search .................. 436/164
    See application file for complete search history.

(56) References Cited

U.S. PATENT DOCUMENTS 4,839,112 A    6/1989  Wynne et al.
(Continued)

FOREIGN PATENT DOCUMENTS
WO    WO 95/16681    6/1995
(Continued)

OTHER PUBLICATIONS

Armengaud et al., "Electrochemistray of conducting polypyrrole films containing cobalt porphyrin," J. Electroanal. Chem., 1990, 277:197-211.

(Continued)

*Primary Examiner* — Sam P Siefke
(74) *Attorney, Agent, or Firm* — Wolf, Greenfield & Sacks, P.C.

(57) ABSTRACT

The present invention generally relates to polymers with lasing characteristics that allow the polymers to be useful in detecting analytes. In one aspect, the polymer, upon an interaction with an analyte, may exhibit a change in a lasing characteristic that can be determined in some fashion. For example, interaction of an analyte with the polymer may affect the ability of the polymer to reach an excited state that allows stimulated emission of photons to occur, which may be determined, thereby determining the analyte. In another aspect, the polymer, upon interaction with an analyte, may exhibit a change in stimulated emission that is at least 10 times greater with respect to a change in the spontaneous emission of the polymer upon interaction with the analyte. The polymer may be a conjugated polymer in some cases. In one set of embodiments, the polymer includes one or more hydrocarbon side chains, which may be parallel to the polymer backbone in some instances. In another set of embodiments, the polymer may include one or more pendant aromatic rings. In yet another set of embodiments, the polymer may be substantially encapsulated in a hydrocarbon. In still another set of embodiments, the polymer may be substantially resistant to photobleaching. In certain aspects, the polymer may be useful in the detection of explosive agents, such as 2,4,6-trinitrotoluene (TNT) and 2,4-dinitrotoluene (DNT).

29 Claims, 39 Drawing Sheets

U.S. PATENT DOCUMENTS

| | | | |
|---|---|---|---|
| 4,841,099 | A | 6/1989 | Epstein et al. |
| 4,957,615 | A | 9/1990 | Ushizawa et al. |
| 4,992,244 | A | 2/1991 | Grate |
| 5,091,502 | A | 2/1992 | Narang et al. |
| 5,237,582 | A | 8/1993 | Moses |
| 5,250,439 | A | 10/1993 | Musho et al. |
| 5,312,896 | A | 5/1994 | Bhardwaj et al. |
| 5,323,309 | A | 6/1994 | Taylor et al. |
| 5,387,462 | A | 2/1995 | Debe |
| 5,493,017 | A | 2/1996 | Therien et al. |
| 5,549,851 | A | 8/1996 | Fukushima et al. |
| 5,675,001 | A | 10/1997 | Hoffman et al. |
| 6,020,426 | A | 2/2000 | Yamaguchi et al. |
| 6,323,309 | B1 | 11/2001 | Swager et al. |
| 6,783,814 | B2 | 8/2004 | Swager et al. |
| 7,041,910 | B2 | 5/2006 | Swager et al. |
| 7,088,757 | B1 | 8/2006 | Yu et al. |
| 7,291,503 | B2 | 11/2007 | Swager |
| 7,462,325 | B2 | 12/2008 | Hancock et al. |
| 7,521,232 | B2 | 4/2009 | Moon |
| 2002/0040805 | A1 | 4/2002 | Swager et al. |
| 2003/0178607 | A1 | 9/2003 | Swager et al. |
| 2004/0116650 | A1 | 6/2004 | Swager et al. |
| 2004/0121337 | A1 | 6/2004 | Deans et al. |
| 2004/0170775 | A1 | 9/2004 | Swager et al. |
| 2005/0147534 | A1 | 7/2005 | Swager et al. |
| 2006/0024707 | A1 | 2/2006 | Deans et al. |

FOREIGN PATENT DOCUMENTS

| | | |
|---|---|---|
| WO | WO 99/57222 | 5/1999 |
| WO | WO 00/05774 | 7/1999 |
| WO | WO 00/05774 | 2/2000 |
| WO | WO 02/16463 | 8/2001 |
| WO | WO 02/16463 | 2/2002 |

OTHER PUBLICATIONS

Audebert et al., "Description of New Redox and Conducting Polymers Based on Copper Containing Units; Emphasis on the Role of Copper in the Electron Transfer Mechanism," Synthetic Metals, 1991, 3049-3052.

Audebert et al., "Redox and Conducting Polymers Based on Salen-Type Metal Units; Electrochemical Study and Some Characteristics," New Journal of Chemistry, 1992 16(6):697-703.

Audebert et al., "Synthesis and Characteristics of New Redox Polymers Based on Copper Containing Units; Evidence for the Participation of Copper in the Electron Transfer Mechanism," New Journal of Chemistry, 1991, 15(4):235-237.

Bedioui et al., "Electrochemistry of conducting polypyrrole films containing cobalt porphyrin, Part 2. New Developments and inclusion of metallic aggregates in the coordination polymer," J. Electroanal. Chem., 1991, 297:257-269.

Bedioui et al., "Electrooxidative polymerization of cobalt, nickel and manganese salen complexes in acetonitrile solution," J. Electroanal. Chem., 1991, 301:267-274.

Bedioui et al., "Poly(Pyrrole-Manganese Tetraphenylporphyrin) film Electrodes in Acetonitrile Solution," J. Electroanal. Chem., 1988, 239:433-439.

Bettelheim et al., "Electrochemical Polymerization of Amino-, Pyrrole-, and Hydroxy-Substituted Tetraphenylporphyrins," Inorganic Chemistry, 1987, 26(7):1009-1017.

Cameron et al., "A conjugated polymer/redox polymer hybrid with electronic communication between metal centres," Chem. Commun., 1997, 303-304.

Cumming et al., "Using Novel Fluorescent Polymers as Sensory Materials for Above-Ground Sensing of Chemical Signature Compounds Emanating from Buried Landmines," IEEE Transactions on Geoscience and Remote Sensing, 2001, 39:1119-1128.

Dahm et al., "Catalytic Reduction of Iodoethane and 2-Iodopropane at Carbon Electrodes Coated with Anodically Polymerized Films of Nickel(II) Salen," Analytical Chemistry, 1994, 66(19):3117-3123.

Goldsby et al., "Oxidation of Nickel(II) Bis(salicylaldimine) Complexes: Solvent Control of the Ultimate Redox Site," Polyhedron, 1989, 8(1):113-115.

Goldsby et al., "Symmetric and Unsymmetric Nickel(II) Schiff Base Complexes; Metal-Localized Versus Ligand-Localized Oxidation," J. Coord. Chem., 1988, 19:83-90.

Hoferkamp et al., "Surface-Midfied Electrodes Based on Nickel(II) and Copper(II) Bis(salicylaldimine) Complexes," Chemistry of Materials, 1989, 1(3):348-352.

Horwitz et al., "Oxidative Electropolymerization of Metal Schiff-Base Complexes," Mol. Cryst. Liq. Cryst., 1988, 160:389-404.

Levitsky et al., "Energy Migration in a Poly(phenylene ethynylene): Determination of Interpolymer Transport in Anisotropic Langmuir—Blodgett Films," J. Am. Chem. Soc., 1999, 121:1466-1472.

McQuade et al., Conjugated Polymer-Based Chemical Sensors, Chem. Rev., 2000 100:2537-2574.

Moisy et al., "Epoxidation of cis-cyclooctene by Molecular Oxygen Electrocatalysed by Polypyrrole-Manganese Porphyrin Film Modified Electrodes," J. Electroanal. Chem., 1988, 250:191-199.

Reddinger et al., "Electroactive π-Conjugated Polymers Based on Transition Metal-Containing Thiophenes Capable of Sensing Ionic and Neutral Species," ACS Polym. Prepr., 1997, 321-322.

Reddinger et al., "Electroactive π-Conjugated Polymers Based on Transition Metal-Containing Thiophenes," Synthetic Metals, 1997, 84:225-226.

Reddinger et al., "Tunable Redox and Optical Properties Using Transition Metal-Complexed Polythiophenes," Macromolecules, 1997, 30(3):673-675.

Rose et al., "Excited-State Lifetime Modulation in Triphenylene-Based Conjugated Polymers," J. Am. Chem. Soc., 2001, 123:11298-11299.

Segawa et al., "Approaches to conducting polymer devices with nano-structure: Electrochemical construction of one-dimensional and two-dimensional prophyrin-oligothiophene co=polymers," Synthetic Metals, 1995, 71:2151-2154.

Shimidzu et al., "Approaches to conducting polymer devices with nanostructures: photoelectrochemical function of one-dimensional and two-dimensional porphyrin polymers with oligothienyl molecular wire," Journal of Photochemistry and Photobiology A: Chemistry 99, 1995, Article 4168:1-7.

Swager, "The Molecular Wire Approach to Sensory Signal Application," Acc. Chem. Res., 1998, 31:201-207.

Vilas-Boas et al., "New Insights into the Strucitre and Properties of Electroactive Polymer Films Derived from [Ni(salen)]," Inorganic Chemistry, 1997, 36(22):4919-4929.

Yang et al., Porous Shape Persistent Fluorescent Polymer Films: An Approach to TNT Sensory Materials, J. Am. Chem. Soc. , 1998, 120:5321-5322.

Zahn et al., "Three-Dimensional Electronic Delocalization in Chiral Conjugated Polymers," Angew. Chem. Int. Ed. Engl., 2002, 41(22):4225-4230.

Zhou et al., "Fluorescent Chemosensors Based on Energy Migration in Conjugated Polymers: The Molecular Wire Approach to Increased Sensitivity," J. Am. Chem. Soc., 1995, 117:12593-12602.

Zhou et al., "Methodology for Enhancing the Sensitivity of Fluorescent Chemosensors: Energy Migration in Conjugated Polymers," J. Am. Chem. Soc., 1995, 117:7017-7018.

Zhu et al., "Conducting Polymetallorotaxanes: A Supramolecular Approach to Transition Metal Ion Sensors," Journal of the American Chemical Society, 1996, 118(36):8713-8714.

Zotti et al., "Conductivity in Redox Modified Conducting Polymers. 2. Enhanced Redox Conductivity in Ferrocene-Substituted Polypyrroles and Polythiophenes," Chem. Mater., 1995 7(12):2309-2315.

ORGANIC MATERIALS ABLE TO DETECT ANALYTES

RELATED APPLICATIONS

This application is a continuation of U.S. patent application Ser. No. 11/005,631, filed Dec. 6, 2004, entitled "Organic Materials Able To Detect Analytes," by Rose et al., which claims priority under 35 U.S.C. §119(e) to U.S. Provisional Patent Application Ser. No. 60/527,395, filed Dec. 5, 2003, entitled "Organic Materials Able To Detect Analytes," by Rose, et al, both of which applications are incorporated herein by reference in their entirety.

FEDERALLY SPONSORED RESEARCH

This invention was made with government support under Contract Number 6891253, awarded by DARPA, and Grant No NAS2-02056, awarded by NASA. The government has certain rights in the invention.

FIELD OF INVENTION

The present invention generally relates to polymers with lasing characteristics and, in particular, to polymers with lasing characteristics that allow the polymers to be useful in detecting analytes. In some cases, the polymers may be thermally, photochemically, and/or chemically stable in thin films. In certain instances, the polymers may be soluble in organic solvents. In one set of embodiments, the polymers comprise conjugated backbones and use electron withdrawing groups to affect the electron affinity of the polymers.

BACKGROUND

Semiconducting organic polymers have emerged as important class of luminescent sensor materials due to their ability to self-amplify. Non-limiting examples of organic polymers that may be semiconductive are disclosed in the following: U.S. patent application Ser. No. 09/305,379, filed May 5, 1999, entitled "Emissive Polymers and Devices Incorporating These Polymers," by Swager, et al.; U.S. patent application Ser. No. 09/935,060, filed Aug. 21, 2001, entitled "Polymers with High Internal Free Volume," by Swager, et al.; and U.S. patent application Ser. No. 10/680,714, filed Oct. 27, 2003, entitled "Emissive Sensors and Devices Incorporating These Sensors," by Swager, et al. Each of these is incorporated herein by reference.

SUMMARY OF THE INVENTION

The present invention generally relates to polymers with lasing characteristics that allow the polymers to be useful in detecting analytes. The subject matter of the present invention involves, in some cases, interrelated products, alternative solutions to a particular problem, and/or a plurality of different uses of one or more systems and/or articles.

One aspect of the invention provides a device. In one set of embodiments, the device is a device for detecting an analyte. In one embodiment, the device includes a polymer that, upon interaction with an analyte, exhibits a change in a lasing characteristic. The device also includes, in some cases, an energy source able to cause the polymer to lase.

In another aspect of the invention, an article is provided. According to one set of embodiments, the article includes a polymer, that, upon interaction with an analyte, exhibits a change in a stimulated emission signal that is at least 10 times greater than a change in a spontaneous emission signal of the polymer. In another set of embodiments, the article includes a polymer that, upon interaction with an analyte, exhibits a change in a lasing characteristic. In some cases, the polymer further includes a binding site for an analyte which, when it binds at the site, changes the lasing characteristic.

The invention, in yet another aspect, provides a method. The method, according to one set of embodiments, is a method of determining an analyte. The method, in one embodiment, includes acts of contacting a polymer with a sample suspected of containing an analyte, and determining a change in a lasing characteristic of the polymer indicative of the presence of the analyte in the sample. In another embodiment, the method includes acts of contacting a polymer with a sample suspected of containing an analyte, and determining a change in a stimulated emission signal of the polymer that is at least 10 times greater than a change in a spontaneous emission signal of the polymer indicative of the presence of the analyte in the sample.

In one set of embodiments, the polymer is fluorescent. The polymer may also be semiconductive in some cases. In one embodiment, the polymer comprises a conjugated backbone and one or more electron donating and/or electron withdrawing groups bonded to or otherwise associated with the polymer. For example, electron withdrawing groups may be bonded directly to the conjugated backbone, or bonded to the polymer, but not bonded directly to the conjugated backbone.

In another aspect, the present invention is directed to a method of making one or more of the embodiments described herein. In yet another aspect, the present invention is directed to a method of using one or more of the embodiments described herein. In still another aspect, the present invention is directed to a method of promoting one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the later-filed application shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
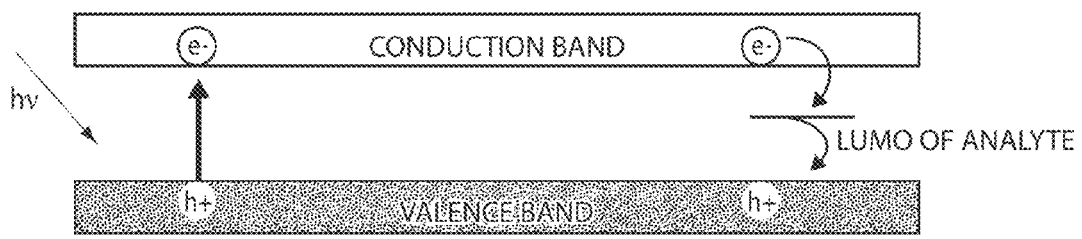
FIG. 1 is a schematic diagram of a fluorescence quenching mechanism.

The present invention generally relates to polymers with lasing characteristics that allow the polymers to be useful in detecting analytes. In one aspect, the polymer, upon an interaction with an analyte, may exhibit a change in a lasing characteristic that can be determined in some fashion. For example, interaction of an analyte with the polymer may affect the ability of the polymer to reach an excited state that allows stimulated emission of photons to occur, which may be determined, thereby determining the analyte. In another aspect, the polymer, upon interaction with an analyte, may exhibit a change in stimulated emission that is at least 10 times greater with respect to a change in the spontaneous emission of the polymer upon interaction with the analyte. The polymer may be a conjugated polymer in some cases. In one set of embodiments, the polymer includes one or more hydrocarbon side chains, which may be parallel to the polymer backbone in some instances. In another set of embodiments, the polymer may include one or more pendant aromatic rings. In yet another set of embodiments, the polymer may be substantially encapsulated in a hydrocarbon. In still another set of embodiments, the polymer may be substantially resistant to photobleaching. In certain aspects, the polymer may be useful in the detection of explosive agents, such as 2,4,6-trinitrotoluene (TNT) and 2,4-dinitrotoluene (DNT).

The following documents are incorporated herein by reference: U.S. patent application Ser. No. 09/305,379, filed May 5, 1999, entitled "Emissive Polymers and Devices Incorporating These Polymers," by Swager, et al.; U.S. patent application Ser. No. 09/935,060, filed Aug. 21, 2001, entitled "Polymers with High Internal Free Volume," by Swager, et al., now U.S. Pat. No. 6,783,814, issued Aug. 31, 2004; U.S. patent application Ser. No. 10/324,064, filed Dec. 18, 2002, entitled "Emissive Polymers and Devices Incorporating These Polymers," by Swager, et al., published as 2003-0178607 on Sep. 25, 2003; U.S. patent application Ser. No. 10/680,714, filed Oct. 27, 2003, entitled "Emissive Sensors and Devices Incorporating These Sensors," by Swager, et al.; U.S. Provisional Patent Application Ser. No. 60/527,395, filed Dec. 5, 2003, entitled "Organic Materials Able To Detect Analytes," by Rose, et al.; and U.S. patent application Ser. No. 10/823,093, filed Apr. 12, 2004, entitled "Emissive Sensors and Devices Incorporating These Sensors," by Swager, et al.; U.S. patent application Ser. No. 10/764,768, filed Jan. 26, 2004, entitled "Polymers with High Internal Free Volume," Swager, et al.

In some embodiments, the polymer is provided in conjunction with a material defining a substantially non-light scattering optical medium which can interact optically with the polymer to cause light emission, changes in which can be caused by interaction of the polymer and/or the optical medium with an analyte. The light emitted may be substantially monochromatic, include a limited number of wavelengths (or "modes"), or the light may be emitted in a broad range of wavelengths. The polymer can be provided in conjunction with the medium by being in optical communication with the medium in some manner, for example, being positioned proximate the medium such that light can readily move between the polymer and the medium, or provided directly upon the medium itself. For example, the polymer can be provided as a thin layer on a surface of the optical medium, such as a substrate.

The substantially non-light scattering medium can be transparent to (i.e., not substantially scattered by) wavelengths of electromagnetic radiation of interest, that is, wavelengths at which emission occurs and can be changed by the presence of an analyte. The optical medium can be readily selected by those of ordinary skill in the art based upon the present disclosure from materials including silica, other glasses, polymers such as polycarbonate, or the like. In one embodiment, the optical medium provides optical feedback to the polymer, which acts as an emitter of light, sufficient to create amplified stimulated emission. In this case, the optical medium serves as a medium for the collection of light at a concentration high enough to provide amplified stimulated emission. Those of ordinary skill in the art will recognize and readily be able to select and construct combinations of polymers and optical media of dimension and geometry such that optical characteristics including amplified stimulated emission as described here and can occur. Where the optical medium provides feedback at selective modes, the optical medium alone and/or in combination with the polymer can define a laser.

A variety of definitions are now provided, which will aid in understanding various aspects of the invention. Following, and interspersed with these definitions, is additional disclosure that will more fully describe the invention.

The term "fluid," as used herein, is defined as a substance that tends to flow and to conform to the outline of its container. Typically, fluids are materials that are unable to withstand a static shear stress. When a shear stress is applied to a fluid, it experiences a continuing and permanent distortion. Typical fluids include liquids and gases.

As used herein, the term "determining" (and similar terms) generally refers to the measurement and/or analysis of a species, for example, quantitatively or qualitatively, and/or the detection of the presence or absence of the species. "Determining" may also refer to the measurement and/or analysis of an interaction between two or more species, for example, quantitatively or qualitatively, and/or by detecting the presence or absence of the interaction.

As used herein, the term "sample" refers to any medium that can be evaluated in accordance with the invention, such as air, soil, water, a biological sample, etc. A "sample suspected of containing" a particular component means a sample with respect to which the content of the component is unknown. For example, a soil sample may be suspected of having one or more explosive agents, but is not known to have the explosive agent. "Sample" in this context includes naturally-occurring samples, such as soil samples, water samples, air samples, samples from food, livestock, plants, etc.

As used herein, "binding" includes covalent binding, ionic binding, hydrogen binding, van der Waals interactions, metal ligand binding, dative binding, coordinated binding, hydrophobic interactions, or the like.

As used herein, "alkyl" is given its ordinary meaning as used in the field of organic chemistry. Alkyl (i.e., aliphatic) moieties useful for practicing the invention can contain any of a wide number of carbon atoms, for example, between and 1 and 25 carbon atoms, between 1 and 20 carbon atoms, between 1 and 15 carbon atoms, between 1 and 10 carbon atoms, or between 1 and 5 carbon atoms. In some embodiments, the alkyl moiety will contain at least 1 carbon atom, at least 3 carbon atoms, at least 5 carbon atoms, or at least 10 carbon atoms; in other embodiments, the alkyl moiety will have at most 10 carbon atoms, at most 5 carbon atoms, or at most 3 carbon atoms. The carbon atoms within the alkyl moiety may be arranged in any configuration within the alkyl moiety, for example, as a straight chain (i.e., a n-alkyl such as methyl, ethyl, propyl, butyl, pentyl, hexyl, heptyl, octyl, etc.) or a branched chain, i.e., a chain where there is at least one carbon atom that is covalently bonded to at least three carbon atoms (e.g., a t-butyl moiety, an isoalkyl moiety such as an isopropyl moiety or an isobutyl moiety, etc.). In certain embodiments, a straight chain or branched chain alkyl has about 30 or fewer carbon atoms (e.g., $C_1$-$C_{30}$ for straight chain, $C_3$-$C_{30}$ for branched chain), in some cases, about 20 or fewer atoms, etc. The alkyl moiety may contain only single bonds (i.e., the alkyl is "saturated"), or may contain one or more double and/or triple bonds within its structure (i.e., the alkyl is "unsaturated"), for example, as in an alkene, an alkyne, an alkadiene, an alkadiyne, an alkenyne, etc.

In some cases, the alkyl moiety contains only carbon and hydrogen atoms; however, in other embodiments, the alkyl moiety may also contain one or more substituents, i.e., a non-carbon and non-hydrogen atom ("a "heteroatom") may be present within the alkyl moiety. Non-limiting examples of heteroatoms include halogens, boron, nitrogen, oxygen, phosphorus, sulfur, and selenium. For example, the alkyl moiety may include a halogen, an alkoxy moiety (e.g., methoxy or ethoxy), an amine moiety (e.g., a primary, secondary, or tertiary amine), a carbonyl (e.g., an aldehyde and/or a ketone), and/or a hydroxide as a substituent. If more than substituent is present within the alkyl moiety, then the substituents may each independently be the same or different. In one embodiment, an alkyl is a perhalogenated alkyl, as further discussed below.

An alkyl may be acyclic, or cyclic in some cases. Cyclic alkyls include, but are not limited to, cycloalkyl (alicyclic) moieties, aromatic moieties, aralkyl moieties, alkyl substituted cycloalkylmoieties, cycloalkyl substituted alkylmoieties, etc. Certain cycloalkyls may have from about 3 to about 10 carbon atoms in their ring structure, for instance, 5, 6, or 7 carbons in a ring structure.

An "aromatic" moiety is given its ordinary meaning as used in the art, i.e., a moiety having at least one ring in which some electrons are delocalized in the ring. For instance, the aromatic moiety may include a benzene moiety, a naphthalenyl moiety, an anthracenyl moiety, a pyridinyl moiety, a furanyl moiety, etc. Examples of aromatic compounds include, but are not limited to, nitroaromatics such as 2,4,6-trinitrotoluene (TNT), 2,4-dinitrotoluene (DNT), nitrotoluene, etc. Other non-limiting examples of aromatics that are of biological or environmental importance include, but are not limited to, dioxin, dopamine, aniline, benzene, toluene, and phenols.

The term "aryl" is art-recognized, and includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryls." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls. Similarly, the term "aralkyl" is art-recognized, and includes alkyl groups substituted with an aryl group (e.g., an aromatic or heteroaromatic group).

The terms "heterocyclyl" and "heterocyclic group" are art-recognized, and, in some cases, include 3- to 10-membered ring structures, such as 3- to 7-membered rings, for example, whose ring structures include one to four heteroatoms. Heterocycles may also be polycycles in some cases. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The definition of each expression, e.g. alkyl, m, n, etc., when it occurs more than once in any structure, is intended to be independent of its definition elsewhere in the same structure unless otherwise indicated expressly or by the context.

A "polymer," as used herein, is an extended molecular structure comprising a backbone which optionally contains pendant side groups, where "backbone" generally refers to the longest continuous bond pathway of the polymer. Those of ordinary skill in the art will be able to identify the backbone of a polymer. In one embodiment, the polymer includes one or more polyarylenes, polyarylene vinylenes, polyarylene ethynylenes, and/or ladder polymers, i.e. polymers having a backbone that can only be severed by breaking two bonds. Examples of such polymers include, but are not limited to, polythiophene, polypyrrole, polyacetylene, polyphenylene and substituted derivatives thereof.

Non-limiting examples of polymers suitable for the invention include those disclosed in U.S. patent application Ser. No. 09/305,379, filed May 5, 1999, entitled "Emissive Polymers and Devices Incorporating These Polymers," by Swager, et al.; U.S. patent application Ser. No. 09/935,060, filed Aug. 21, 2001, entitled "Polymers with High Internal Free Volume," by Swager, et al.; and U.S. patent application Ser. No. 10/680,714, filed Oct. 27, 2003, entitled "Emissive Sensors and Devices Incorporating These Sensors," by Swager, et al, each incorporated herein by reference. Other examples of polymers suitable for the invention are described in more detail herein.

The polymer is, in some cases, a homo-polymer or a co-polymer, such as a random co-polymer or a block co-polymer. In one embodiment, the polymer is a block co-polymer. An advantageous feature of block co-polymers is that the effect of a multi-layer can be mimicked. For example, each block may have different band gap components, and by nature of the chemical structure of a block co-polymer, each gap component may be segregated in some embodiments. Thus, amplified emissions can be achieved with block co-polymers, and a broad scope of structures can be produced, according to certain embodiments of the invention. Band gaps, amplifications and selectivities for analytes can thus be achieved by modification or incorporation of different polymer types. The polymer compositions can vary continuously to give a tapered block structure, according to some embodiments, and the polymers can be synthesized by methods known to those of ordinary skill in the art, such as step growth, chain growth, or the like.

One aspect of the present invention provides a polymer capable of emission, wherein the emission may be variable and sensitive to a dielectric constant of a surrounding medium. In some cases, the polymer is semiconductive. In one set of embodiments, the polymer has a backbone including a plurality of chromophores, which may be interrupted by non-conjugated groups in some cases. Non-conjugated groups include, for example, saturated units such as a chain of alkyl groups optionally interrupted by heteroatoms. A "chromophore," as used herein, refers to a species that can either absorb or emit electromagnetic radiation. In some embodiments, the chromophore is capable of absorbing or emitting radiation in the ultraviolet and/or visible range, i.e. absorbing or emitting energy involving excited electronic states. In one embodiment, the chromophore is a conjugated group. As used herein, a "conjugated group" refers to an interconnected chain of at least three atoms, each atom participating in delocalized pi-bonding.

In another set of embodiments, at least a portion of the polymer is conjugated, i.e. the polymer has one or more conjugated portions. For example, in one embodiment, the polymer backbone includes at least one conjugated group. In the conjugated portion, electron density and/or electronic charge can be conducted along that portion, and such electron density and/or electronic charge may be referred to as being "delocalized." Within the conjugated portion, each p-orbital participating in the conjugation may have sufficient overlap with adjacent conjugated p-orbitals. In one embodiment, the conjugated portion is at least about 3 nm in length and in some cases, the conjugated portion is at least about 5 nm, at least about 10 nm, at least about 15 nm, at least about 25 nm, or more in length. In another embodiment, the entire backbone, or substantially all of the entire backbone, is conjugated and the polymer is referred to as a "conjugated polymer," i.e., the entire polymer, or substantially all of the entire polymer, is the "conjugated portion." Polymers having a conjugated backbone capable of conducting electronic charge along the backbone are typically referred to herein as "conducting polymers." In the present invention, the conducting polymers may comprise, in some cases, chromophore monomeric units, or chromophores interspersed between other conjugated groups. In certain cases, the atoms directly participating in the conjugation essentially define a plane, which may arise from a preferred arrangement of the p-orbitals to maximize p-orbital overlap, thus maximizing conjugation and electronic conduction. An example of a conjugated-backbone defining essentially a plane of atoms are the carbon atoms of a polyacetylene chain.

In one embodiment, a polymer is provided having a conjugated backbone defining essentially a plane of atoms. A first group of atoms and a second group of atoms are attached to the backbone of the polymer. Both the first and second groups have at least some atoms that are not planar with the plane of atoms, such that the atoms can be positioned above and/or below the conjugated plane of atoms. It is a feature of certain embodiments of the invention that these heights are fixed, where the term "fixed height" is defined herein as a height of an atom that is not planar with the plane of atoms, and where the atom is free of substantial rotational motion.

In another embodiment, the present invention relates to a polymer comprising a conjugated backbone and one or more electron donating and/or electron withdrawing groups associated with the polymer, for example, bonded to the polymer.

The polymer may comprise, in some cases, one or more electron withdrawing groups, where a portion of the electron withdrawing group is directly bonded to the conjugated backbone, and/or the polymer may comprise one or more electron withdrawing groups that are not bonded directly to the backbone. For example, in some embodiments, the polymer comprises a first moiety where the electron withdrawing group is not bonded directly to the backbone, and a second moiety where the electron withdrawing group is bonded directly to the conjugated backbone. The term "electron-withdrawing group" is art-recognized, and generally refers to the tendency of a substituent to attract valence electrons from neighboring atoms, i.e., the substituent is electronegative with respect to neighboring atoms. In some cases, quantification of the level of electron-withdrawing capability may be given by the Hammett sigma ($\sigma$) constant. This constant is described in many references, for instance, March, *Advanced Organic Chemistry*, 251-59 (McGraw Hill Book Company: New York, 1977). The Hammett constant values are generally negative for electron donating groups (e.g., sigma(P) or $\sigma(P)=-0.66$ for $NH_2$) and positive for electron withdrawing groups (e.g., sigma(P) or $\sigma(P)=0.78$ for $NO_2$). Examples of electron-withdrawing groups include, but are not limited to, halogenated alkyl groups such as trifluoromethyl, acyl, formyl, sulfonyl, sulfonium, sulfate, nitrile, halide, any electron deficient ring as compared to benzene (e.g. a benzene ring with an electron withdrawing group attached to the ring or a nitrogen containing aromatic ring, etc.), or the like. In some embodiments, the electron withdrawing groups are not bonded directly to the conjugated backbone, and in certain instances, the polymer may have a hyperconjugated 3-D structure. Other non-limiting examples of electron withdrawing groups include esters, perhalogenated alkyls, perhalogenated aryls, nitriles, electron deficient heteroaryls, perfluorinated alkyls, or the like. Non-limiting examples of perfluorinated alkyls include perfluorinated $C_1$-$C_{12}$ alkyls; specific examples include —$CF_3$, —$C_2F_5$, —$C_3F_7$, —$C_4F_9$, —$C_5F_{11}$, —$C_6F_{13}$, —$C_7F_{15}$, —$C_8F_{17}$, —$C_9F_{19}$, —$C_{10}F_{21}$, —$C_{11}F_{23}$, etc. and all isomers thereof. For example, a polymer may be substituted with fluorinated alcohol groups for hydrogen bonding with weak hydrogen bonded acceptors such as nitro groups. In some cases, electron-poor polymers, for example, produced through the use of electron withdrawing groups, can enable quenching by electron-rich analytes and thus, in one embodiment, sensors having specificity for electron-rich analytes are provided. Sensitivity to electron-rich analytes can be achieved, in some cases, by substituting a polymer with groups that increase electron affinity, such as electron withdrawing groups.

Certain perfluorinated alkyls may provide a higher degree of solubility than the analogous polymers of equal chain length hydrocarbon substituents, according to some embodiments of the invention. In some cases, the perfluorinated alkyls may prevent strong interpolymer interactions, and in some instances, thin films of these materials may maintain fluorescence while in the solid state. The high electron affinity of the perfluorinated alkyls, in some embodiments, may complement other sensor materials, e.g., as described herein.

The polymer may be fluorescent and/or semiconductive in some cases. The term "fluorescence" is art-recognized and generally refers to the emission of electromagnetic radiation caused by an electronic transition from an excited electronic state of a given spin to a lower energy electronic state. In yet another embodiment, the present invention includes conjugated polymers that produce high fluorescence quantum yields. In some cases, the polymer can also be used to tune electron affinity. Architectures are provided herein for the covalent attachment of the conjugated polymers to peptides, nucleic acids, antibodies, etc., e.g., for biosensor applications that avoid deleterious reductions in their electronic delocalization. In some cases, conjugated polymers having three-dimensional structures that display efficient solid-state fluorescence may be used, and hyperconjugation can be used to tune electron affinities of the polymers. In one embodiment, multiple conjugated polymers having different electronic properties due to strongly electron withdrawing groups directly attached to their backbones may be used.

Semiconductive polymers having electron withdrawing substituents directly attached to conjugated portions of the polymers are provided in another embodiment of the invention. For example, semiconductive polymers containing perfluorinated alkyl groups, or other electron withdrawing groups, may have a relatively high electron affinity that prevents oxidative degradation (photobleaching). The term "photobleaching" is art-recognized, and refers to the decrease in absorbance intensity upon exposure to light and/or, in the case of fluorescent materials, a decrease in emission intensity. The perfluorinated alkyl polymers disclosed herein are generally stable after one or more hours of irradiation with UV light (e.g. a 450 W, short-arc, Xe lamp) in solid state, under ambient atmosphere.

Polymers having hydrogen-bonding capabilities can also be synthesized, according to other embodiments of the invention. For example, in one embodiment, the invention provides the ability to detect analytes capable of hydrogen-bonding interactions. In another embodiment, the polymer is soluble in an organic solvent.

In some embodiments of the invention, the polymers may be present in a composition that is rigid with respect to the relative orientation between the polymers. In one embodiment, the compositions of the present invention are rigid to the extent that the polymer arrangement does not substantially change over time, upon exposure to solvent or upon heating to a temperature of no more than about 150° C. That is, the rigidity of the side group defining a fixed height may not substantially change and the height may not be affected upon heating. In one embodiment, the exposure to solvent or heating step occurs over a period of time of about 5 minutes, about 10 minutes, about 15 minutes, about 30 minutes, or about 1 hour. In one embodiment, the composition is characterized by a first optical spectrum having at least one maximum or maxima. The composition is then exposed to a solvent or heated to a temperature of less than about 140° C. and a second optical spectrum is obtained. A maximum or maxima in the first spectrum differ by no more than about 15 nm from a corresponding maximum or maxima in the second spectrum, and in some cases, by no more than about 10 nm or about 5 nm. In another embodiment, the maxima in the second spectrum may have an intensity change of less than about 10%, or about 15% relative to the maxima in the first spectrum.

In one set of embodiments, the polymer has a structure:

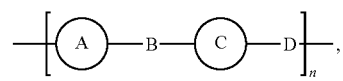

where n is at least 1, A and C are each independently aromatic, and at least one of B and D comprises a —C═C— structure (i.e., a double bond) or —C≡C— structure (i.e., a triple bond). In another set of embodiments, the polymer has a structure:

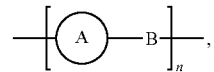

where n is at least 1, A is aromatic, and B comprises a —C═C— structure (i.e., a double bond) or —C≡C— structure (i.e., a triple bond).

In some embodiments, the polymer may include one or more pendant aromatic groups. The pendant aromatic groups may increase the optical cross-section of the polymer, which may enhance absorption efficiency and/or emission efficiency in some cases. In one set of embodiments, the polymer has a structure:

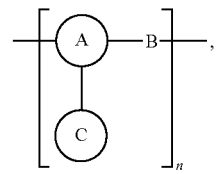

where n is at least 1, A and C are each independently aromatic, and B comprises a —C═C— structure (i.e., a double bond)

or —C≡C— structure (i.e., a triple bond). In another set of embodiments, the polymer has a structure:

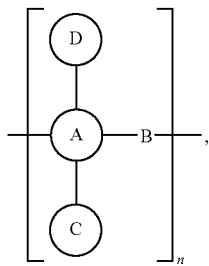

where n is at least 1, A, C, and D are each independently aromatic; and B comprises a —C=C— structure (i.e., a double bond) or —C≡C— structure (i.e., a triple bond). In another set of embodiments, the polymer has a structure:

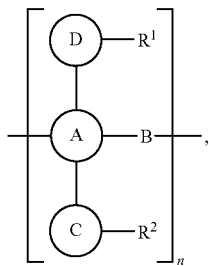

where n is at least 1, A, C, and D are each independently aromatic; B comprises a —C=C— structure (i.e., a double bond) or —C≡C— structure (i.e., a triple bond), and each of $R^1$ and $R^2$ independently comprises a hydrocarbon, as further discussed herein. In yet another set of embodiments, the polymer has a structure:

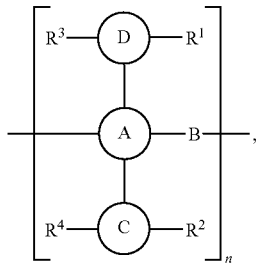

where n is at least 1, A, C, and D are each independently aromatic, B comprises a —C=C— structure (i.e., a double bond) or —C≡C— structure (i.e., a triple bond), and each of $R^1$, $R^2$, $R^3$, and $R^4$ independently comprises a hydrocarbon. In the above structures, n may be, for example, at least 2, at least 3, at least 5, at least 10, at least 30, at least 100, at least 300, at least 1,000, at least 3,000, at least 10,000, at least 100,000, or at least 1,000,000. In one embodiment, n is less than $10^8$.

In some embodiments, the polymer includes one or more hydrocarbon side chains substantially parallel to the backbone of the polymer, i.e., the side chains may substantially parallel the 3-dimensional structure of the backbone (which may or may not be linear). In some cases, one or more pendant groups may be used to secure the hydrocarbon side chains in an orientation such that they are substantially parallel to the backbone of the polymer. As used herein, a "hydrocarbon" is a moiety comprising at least carbon and hydrogen, and in some cases, the hydrocarbon comprises heteroatoms such as oxygen, nitrogen, sulfur, etc. In one embodiment, the hydrocarbon is an alkyl moiety, which may be straight or branched.

In another set of embodiments, the polymer may be substantially surrounded by hydrocarbon. For example, a hydrocarbon may sufficiently surround the polymer to reduce interaction of the polymer with adjacent polymer molecules such that the polymers, for instance, so that the polymer molecules cannot substantially quench each other. As another example, the hydrocarbon may sufficiently surround the polymer such that the ability of $O_2$ or radicals to interact with the polymer is reduced. As yet another example, the hydrocarbon may sufficiently surround the polymer such that the polymer is not photobleached, i.e., after exposure to light for long periods of time, the polymer does not substantially lose its lasing abilities.

In another set of embodiments, the polymer has a structure:

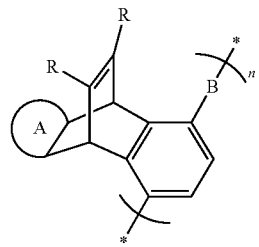

where, independently for each occurrence, R is an electron donating and/or electron withdrawing group or the two instances of R taken together form an electron deficient ring; B is a double bond, triple bond, or aryl group substituted by one or more $R_1$; $R_1$ is R, H, $C_{1-12}$ alkyl, $C_{2-12}$ alkenyl, $C_{2-12}$ alkynyl, aryl, aralkyl, heteroaryl, or heteroaralkyl; A is a fused aryl, cycloalkyl, or cycloalkenyl ring; * depicts an end group for the polymer, for example, H, halide, alkyl, alkoxy, and aryl; and n is an integer greater than 1. In some cases, R may be an ester, a perhalogenated alkyl group, a perfluorinated alkyl group (for example, a $C_{1-12}$ perfluorinated alkyl group), —$CO_2CH_3$, —$CO_2C(CH_3)_3$. Examples of perfluorinated alkyl group include, but are not limited to, —$CF_3$, —$C_2F_5$, —$C_3F_7$, —$C_4F_9$, —$C_5F_{11}$, —$C_6F_{13}$, —$C_7F_{15}$, —$C_8F_{17}$, —$C_9F_{19}$, —$C_{10}F_{21}$, —$C_{11}F_{23}$, etc. In certain embodiments, at least one set of two R groups taken together form an electron deficient heteroaryl moiety. In some cases, A may be a fused benzene ring. In some embodiments, n is greater than about 10, about 100, about 1,000, about 10,000, or about 100,000. In one embodiment, n is less than about $10^8$. As a particular example, R may be —$CO_2CH_3$ or —$CF_3$, $R_1$ may be H, A may be a fused benzene ring, and n may be greater than about 10, 100, 1000, etc.

In yet another set of embodiments, the polymer has a structure:

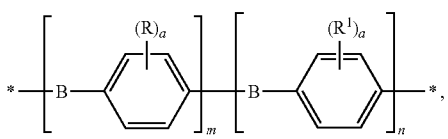

where, independently for each occurrence, B is a double bond, triple bond, or aryl; R is an electron donating and/or electron withdrawing group; $R^1$ is R, H, $C_{1-6}$ alkyl, $C_{2-8}$ alkenyl, $C_{2-8}$ alkynyl, aryl, aralkyl, heteroaryl, heteroaralkyl, $C_{1-12}$ alkoxy, electron deficient ring, or any two adjacent $R^1$ taken together form a monocyclic, bicyclic, tricyclic, or tetracyclic ring which may be substituted by 1 or more R; * depicts an end group for the polymer selected from the group consisting of H, halide, alkyl, alkoxy or aryl; a is an integer from 1-4 inclusive; and m and n are integers 1 or greater. The polymer may be, for example, a random polymer, a block polymer, an alternating polymer, etc. In some cases, R may be an ester, a perhalogenated alkyl group, a perfluorinated alkyl group (for example, a $C_{1-12}$ perfluorinated alkyl group), $-CO_2CH_3$, $-CO_2C(CH_3)_3$. Examples of perfluorinated alkyl group include, but are not limited to, $-CF_3$, $-C_2F_5$, $-C_3F_7$, $-C_4F_9$, $-C_5F_{11}$, $-C_6F_{13}$, $-C_7F_{15}$, $-C_8F_{17}$, $-C_9F_{19}$, $-C_{10}F_{21}$, $-C_{11}F_{23}$, etc. In certain embodiments, at least one set of two R groups taken together form an electron deficient heteroaryl moiety. In some cases, at least one or at least two of $R^1$ is a perfluorinated $C_{1-12}$ alkyl or a $C_{1-12}$ alkoxy group. In some cases, a may be 2 or more, and in certain instances, m and n may independently be greater than about 10, about 100, about 1,000, about 10,000, about 100,000, etc., and in one embodiment, less than about $10^8$. In one embodiment, two sets of adjacent $R^1$ each form a monocyclic ring, a bicyclic ring, a tricyclic ring, or a tetracyclic ring. In some cases, at least one structure comprises a heteroaryl ring. For example, in one embodiment, two sets of $R^1$ each may form a structure:

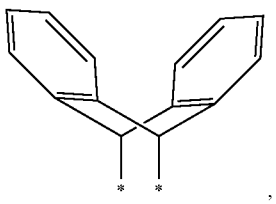

where * depicts a point of contact with the polymer.

Additional, non-limiting examples of polymers suitable for use in the present invention are shown in FIGS. 15A-15G.

In one set of embodiments, the polymer may be present in a film. A film typically has a geometry such that one dimension is substantially less than the other dimensions (i.e., the "thickness" of the material may be substantially less than the other dimensions of the material). In some cases, the thickness of the film may affect the sensitivity of the polymer. For example, the film have a thickness of less than about 1 micron, and in some cases, the film may have a thickness of less than about 750 nm, less than about 600 nm, less than about 500 nm, less than about 400 nm, less than about 200 nm, less than about 100 nm, less than about 40 nm, less than about 30 nm, less than about 20 nm, less than about 10 nm, less than about 5 nm, or less than about 2 nm. In one embodiment, the film has a thickness of at least 1 nm.

Figure 3A:
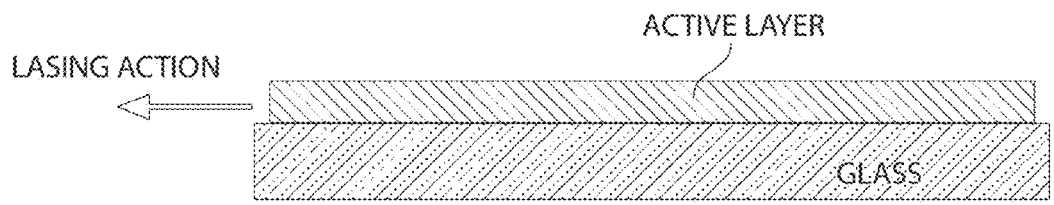
FIGS. 3A-3C are schematic diagrams of various planar lasing structures, in accordance with various embodiments of the invention.
Figure 3B:
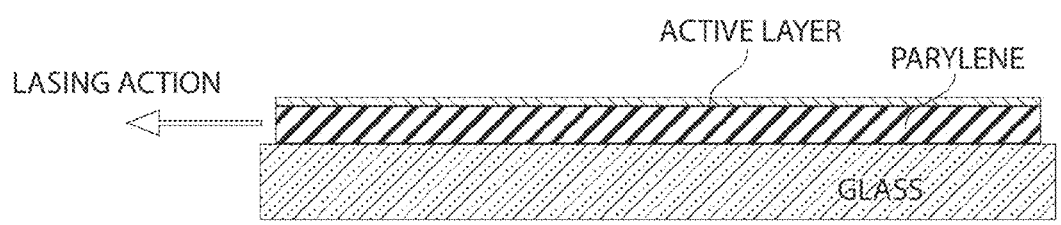
Figure 3C:
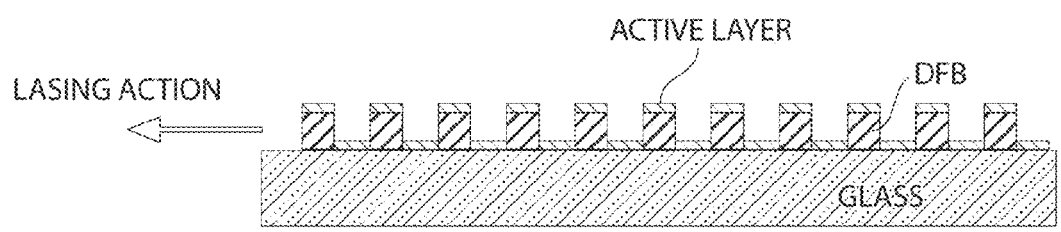

In one embodiment, the film is attached to a substrate, which may serve as an optical medium in some cases. The film may be attached to the substrate using any suitable technique, for example, spin-coating techniques. The substrate may have any shape, and include any material able to support the film. For example, the substrate may be substantially planar or curved, the substrate may be a rod, a wire, or a fiber (for example, a silica fiber), the substrate may comprise discrete particles (e.g., spherical particles), etc. In some embodiments, e.g., as shown in FIG. 3, more than one substrate may be present. As a non-limiting example, a glass substrate may be coated with a film of parylene, then a film of polymer may be coated on the parylene. In FIG. 3, FIG. 3A shows a polymer waveguide on a glass substrate, and FIG. 3B shows a thin polymer layer on parylene. The combined thickness of polymer and parylene may act as a waveguide. FIG. 3C shows a thin polymer layer on a DFB grating, which may significantly reduces the lasing threshold in some cases.

In some cases, the film and the substrate together operate as a waveguide, e.g., as is shown in FIG. 3A. In such cases, the refractive index of the film and the refractive index of the substrate may be chosen such that they are nearly or substantially equal. In some instances, one of the substrate and/or film may be doped in some fashion to match the refractive index of the other. In some cases, one or more of the substrates may be at least substantially transparent, e.g., to the excitation and/or emission wavelengths, and/or optically.

In one embodiment, the substrate has the form of a distributed feedback structure ("DFB") or a distributed feedback grating or other structure. As used herein, a "distributed feedback" structure is given its ordinary meaning in the art, e.g., a structure in which feedback is used to make certain modes in the resonator oscillate more strongly than others. The structure may include a grating (e.g., a Bragg grating) having a spacing chosen to distribute the feedback in both directions, creating a condition that can approach single-mode oscillation, as is shown in FIG. 3C. Those of ordinary skill in the art will know of techniques for producing distributed feedback structures, for example, by using micromolding techniques.

Other substrates may be used in other embodiments of the invention. For example, in one set of embodiments, the polymer (or film comprising the polymer) may be attached to or otherwise associated with a non-light scattering optical medium. Examples of non-light scattering optical medium include, but are not limited to, silica, other glasses, polymers such as polycarbonate, or the like. In another set of embodiments, the non-light scattering optical medium includes an optical fiber. For example, the polymer may be at least partially coated on a surface of the optical fiber (for example, as a film). An interaction of the polymer with an analyte may cause the polymer to alter an optical characteristic of the optical fiber. For example, if the optical fiber is used as a laser, then the interaction may cause the polymer to alter a lasing characteristic of the optical fiber. The non-light scattering optical medium, in some embodiments, may carry or "collect" photons, and, through the use of a feedback mechanism (for example, a distributed feedback structure), may create selective modes for lasing, for example through amplified stimulated emission.

In one aspect, the present invention generally relates to polymers able to generate amplified stimulated emission of electromagnetic radiation, i.e., a laser, and devices such as sensors able to detect analytes which incorporate these polymers, e.g., in films. As used herein, a "laser" is given its ordinary meaning, i.e., an article able to emit amplified and coherent electromagnetic radiation having one or more discrete frequencies, typically in response to an electrical or an optical stimulus (e.g., incident light, or "stimulation" light). The article, when it exhibits such behavior, is said to "lase." The emitted light may have any frequency or wavelength, for example, in the ultraviolet, visible, or infrared wavelengths. Within the laser, atoms may be excited into a metastable "excited" energy state (for example, due to electrical or optical stimulation), such that these excited atoms decay to a lower energy level, releasing photons. Thus, a coherent beam of radiation may be produced within the laser. Any suitable lasing mechanism may be used within the invention. In one aspect of the invention, the ability of the polymer to reach a metastable excited energy state may be affected by the interaction or association of an analyte with the polymer.

In one set of embodiments, the polymer is able to produce coherent light under certain conditions. In some cases, the polymer may exhibit an enhanced lasing characteristic. As used herein, a "lasing characteristic" is a characteristic of the polymer that relates to the ability of the polymer to enter a metastable excited energy state. Examples of lasing characteristics include, but are not limited to, the "lasing threshold" (i.e., the minimal amount of incident stimulation needed for the polymer to reach a metastable excited energy state, for example, the minimal amount of energy, light (photon) intensity, etc.), the stimulated emission (i.e., the amount of energy produced by the polymer, relative to a fixed standard, such as spontaneous emission), the gain (i.e., the relative amount of energy or photons emitted by the laser, relative to the amount of incident energy), etc.

In one set of embodiments, interaction of an analyte with the polymer may alter a lasing characteristic of the polymer. For example, lasing of the polymer may increase or decrease upon interaction of the polymer with the analyte. In some cases, interaction of the analyte with the polymer may change (i.e., increase or decrease) stimulated emission of the polymer, relative to spontaneous emission of the polymer, and such a change may be detectable in some fashion, as described herein. In some cases, the relative change between stimulated emission of the polymer, relative to spontaneous emission of the polymer may be at least a factor of 5 times, and in some cases, at least a factor of 10, 20, 30, 40, 50, 60, 70, 80, 90, 100, 125, 150, 200, 400, 600, 800, 1,000, or more.

In some embodiments, the laser is an electrically-driven laser. In other embodiments, the laser may be "optically-driven" to generate amplified stimulated emission of radiation. As used herein, "optically-driven" refers to components powered by an external optical or electromagnetic radiation source. In an optically-driven device, electromagnetic radiation is directed towards a material (such as a polymer) where the atoms are to be excited. The electromagnetic radiation source may be any suitable source, for example, a flash tube, a diode, or another laser. In yet other embodiments, the laser may include a waveguide or an amplifier.

In one embodiment, the polymer has a quantum yield of at least about 50%, at least about 60%, at least about 70%, at least about 75%, at least about 80%, at least about 85%, at least about 90%, at least about 95%, or at least about 97%. As used herein, the "quantum yield" refers to a number of photons emitted per adsorbed photon of a material (such as a polymer). In some cases, the quantum yield is determined at a wavelength of electromagnetic radiation produced by the power source.

In some embodiments, the analyte, upon association with the polymer, introduces a non-radiative pathway in the polymer, which may attenuate lasing. In some cases, an electron transfer event from the excited state of the polymer to the LUMO of the analyte provides non-radiative decay pathway for the exciton, e.g., as is shown in FIG. 1. Thus, association of the analyte to the polymer may result in a change in the lasing properties of the polymer, and such a change may be determinable.

One aspect of the invention provides a sensor comprising one or more of the polymers described herein. A "sensor," as used herein, refers to any device or article capable of determining an analyte, i.e., a molecule which is to be determined. In one embodiment, the analyte comprises an aromatic moiety. In another embodiment, the analyte is an "explosive agent," i.e., an agent able to detonate. Examples of explosive agents include, but are not limited to 2,4,6-trinitrotoluene (TNT) and 2,4-dinitrotoluene (DNT), nitroglycerine, gunpowder, etc. Other non-limiting examples include RDX (hexahydro-1,3,5-trinitro-1,3,5-triaxine), PETN (2,2-bis[(nitrooxy)-methyl]-1,3-propanediol dinitrate (ester)) and nitroaromatics and other nitro-($NO_2$) containing species, as further described herein. The sensor may determine the absolute value and/or a change in a physical or chemical quantity, such as temperature, pressure, flow rate, or pH, the intensity of light, sound, or radio waves, the presence of a small molecule, the presence of a biological molecule, a change in a characteristic of a bound molecule, or the like, and convert that determination into a useful input signal for an information gathering system. For instance, in one set of embodiments, the polymer exhibits a change in a lasing characteristic upon interaction of the polymer with an analyte. The interaction between the polymer and the analyte may be, e.g., through covalent binding, ionic binding, hydrogen binding, van der Waals interactions, metal ligand binding, dative binding, coordinated binding, hydrophobic interactions, etc. In one embodiment, the polymer ceases to lase upon interaction of the polymer with the analyte. In another embodiment, the polymer begins to lase upon interaction of the polymer with the analyte. In yet another embodiment, the lasing threshold of the polymer may increase or decrease upon interaction of the polymer with the analyte.

In one set of embodiments, the present invention relates to a sensor comprising a polymer as described herein, and a detector capable of detecting an increase or a decrease in fluorescence. In some cases, the sensor is a biosensor. In certain cases, the polymer and the analyte may be optically coupled. the term "optically coupled" when used herein with reference to a polymer and an analyte, or other moiety such as a reaction entity, refers to an association between any of the analyte, other moiety, and the polymer such that energy can move from one to the other, or in which a change in the association can be detected by a change in a lasing characteristic of the polymer. The coupling between the analyte and the polymer may be direct or indirect (i.e., through a linking agent).

In one set of embodiments, the polymer inherently includes the ability to determine the analyte. The polymer may be functionalized in some cases, e.g., comprising pendant groups, functional moieties, linking agents associated with binding partners, etc., to which the analyte may bind and induce a measurable change to the polymer. The binding event can be specific or non-specific. The functional moieties may include simple functional groups, for example, but not limited to, —OH, —CHO, —COON, —$SO_3H$, —CN, —$NH_2$, —SH, —COSH, —COOR, a halide, etc.; and/or biomolecular entities including, but not limited to, amino acids, proteins, sugars, DNA, antibodies, antigens, enzymes, or the like.

In another set of embodiments, the invention provides a polymer and a reaction entity with which the analyte interacts, positioned in relation to the polymer such that the analyte can be determined by determining a change in a characteristic of the polymer, for example, a lasing characteristic. The term "reaction entity" refers to any entity that can interact with an analyte in such a manner to cause a detectable change in characteristic of a polymer. For example, the reaction entity may enhance the interaction between the polymer and the analyte, the reaction entity may generate a new chemical species that has a higher affinity to the polymer, the reaction entity may enrich the analyte around the polymer, or the like. The reaction entity can comprise a binding partner to which the analyte binds in some cases. The reaction entity, when a binding partner, may also comprise a specific binding partner of the analyte. For example, the reaction entity may be a nucleic acid, an antibody, a sugar, a carbohydrate, a protein, etc. A reaction entity that is a catalyst can catalyze a reaction involving the analyte in some instances, resulting in a product that causes a detectable change in a characteristic of the polymer. Another example of a reaction entity is a reactant that reacts with the analyte, which may produce a product that can cause a detectable change in a characteristic of the polymer. The reaction entity can comprise a coating on the polymer in some embodiments, e.g. a coating of a polymer that recognizes molecules in, e.g., a gaseous sample, which may cause a change in conductivity of the polymer which, in turn, can cause a detectable change in a characteristic of the polymer.

The term "binding partner," as used herein, refers to a molecule that can undergo binding with a particular analyte and includes specific, semi-specific, and non-specific binding partners, as known to those of ordinary skill in the art. As used herein the term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair, the ligand would specifically and/or preferentially select its receptor from a complex mixture of molecules, or vice versa. For example, an enzyme would specifically bind to its substrate, a nucleic acid would specifically bind to its complement, an antibody would specifically bind to its antigen, etc. Other non-limiting examples include nucleic acids that specifically bind (hybridize) to their complement, antibodies specifically bind to their antigen, or the like. The binding may be by one or more of a variety of mechanisms including, but not limited to, ionic interactions, covalent interactions, hydrophobic interactions, van der Waals interactions, etc.

Thus, in one set of embodiments, the present invention relates to a method of determining an analyte that is a biological molecule. In one embodiment, the biological molecule is a protein. In another embodiment, the biological molecule is a peptide. In yet another embodiment, the biological molecule is a mono- or oligonucleotide. In a further embodiment, the biological molecule is RNA. In still another embodiment, the biological molecule is DNA. In another embodiment, the biological molecule is determined when it complexes with another peptide molecule, small molecule, RNA, or DNA.

The reaction entity may be positioned, in some embodiments, relative to the polymer in such a way as to cause a determinable change in a lasing characteristic of the polymer. For instance, the reaction entity may be positioned within about 100 nanometers of the polymer, within about 50 nanometers of the polymer, with n about 10 nanometers of the polymer, etc., and the proximity of the reaction entity to the polymer can be determined by those of ordinary skill in the art. In another embodiment, the reaction entity is positioned less than about 5 nanometers from the polymer. In alternative embodiments, the reaction entity is positioned within about 4 nanometers, within about 3 nanometers, within about 2 nanometers, or within about 1 nanometer of the polymer. In one embodiment, the reaction entity is attached to the polymer through a linker. In another embodiment, the polymer itself (or a portion thereof) functions as the reaction entity.

Another set of embodiments of the invention involves an article comprising a sample exposure region and a polymer able to detect the presence or absence of an analyte. The sample exposure region may be any region in close proximity to the polymer where a sample in the sample exposure region addresses at least a portion of the polymer. Examples of sample exposure regions include, but are not limited to, a well, a channel, a microchannel, a gel, or the like. In some embodiments, the sample exposure region holds a sample proximate the polymer, and/or may direct a sample toward the polymer for determination of an analyte in the sample. The polymer may be positioned adjacent to or within the sample exposure region. In other cases, the polymer may be a probe that is inserted into a fluid or fluid flow path. The polymer probe may also comprise a microneedle, and the sample exposure region may be addressable by a biological sample in certain instances. In this arrangement, a device that is constructed and arranged for insertion of a microneedle probe into a biological sample may include a region surrounding the microneedle defining the sample exposure region, and a sample in the sample exposure region may be addressable by the polymer, and vice versa. Fluid flow channels can be created at a size and scale advantageous for use in the invention (microchannels) using a variety of techniques, such as those described in International Patent Publication No. WO 97/33737.

In yet another set of embodiments, an article may comprise a plurality of polymers as described herein able to detect the presence or absence of a plurality of one or more analytes. Different polymers may be differentially doped in some cases, as described above, thereby varying the sensitivity of the polymers to the analyte. Different polymers may also be selected based on their ability to interact with specific analytes in other cases, thereby allowing the determination of a variety of analytes. The plurality of polymers may be arranged in any suitable configuration, for example, randomly oriented, parallel to one another, etc. In one embodiment, the polymers may be oriented in an array on a substrate.

One aspect of the invention involves a sensing element, which can be a sensing element for determining a characteristic of a polymer such as a lasing characteristic, for example, where the polymer has determined the presence, or absence, of an analyte in a sample containing, or suspected of containing, the analyte. Sensors comprising the polymers of the invention may be used, for example, in chemical or environmental applications to detect explosive agents or other analytes of interest. In some cases, the sample size is less than or equal to about 10 microliters, in some cases less than or equal to about 1 microliter, and in some cases less than or equal to about 0.1 microliter. The sample size may be as small as about 10 nanoliters or less in still other cases.

The sensor also may include, in some cases, a source of energy applicable to the polymeric composition to cause stimulated radiation emission. The energy can include optical stimulation (e.g., a laser), electromagnetic radiation, electrical energy, chemical energy, etc. In some instances, the energy is of a frequency that can be absorbed by the polymer to create a metastable excited energy state, resulting in stimulated emission of radiation. The sensor also includes, in some cases, a device for detecting the emission, such as, but not limited to, a photomultiplier, a photodiode or a charge coupled device.

Where a detector is present, any detector capable of determining a characteristic, such as a lasing characteristic, associated with the polymer can be used. The concentration of a species, or analyte, may be detected using the detector from molar concentrations to micromolar concentrations, nanomolar concentrations, or less in some instances. In some cases, sensitivity can be extended to a single molecule. Thus, in one embodiment, an article of the invention is capable of delivering a single analyte molecule to the polymer, and the detector is constructed and arranged to determine a signal resulting from the interaction of the molecule with the polymer.

In another aspect, the present invention relates to a light emitting device (for example, a laser) comprising a polymer as described herein, and a source of electrical current comprising electrodes capable of supplying the polymer with electrons. In some embodiments, the polymer comprises perfluorinated alkyls and/or perfluorinated aryls, and in certain cases, at the interface between the electrodes and the polymer, metal-carbon bonds are formed. For example, the polymer may comprise perfluorinated alkyls and/or perfluorinated aryls, and at the interface between the electrode and the polymer, metal-fluoride complexes may be formed. In another example, the polymer comprises a nitrogen-containing electron-deficient heteroaryl, and at the interface between the electrode and the polymer, metal-nitrogen bonds are formed. In still another example, the polymer comprises a nitrogen-containing electron-deficient heteroaryl and a perfluorinated alkyl and/or a perfluorinated aryl, and at the interface between the electrode and the polymer, metal-carbon bonds, metal-nitrogen bonds and/or metal-fluoride bonds may be formed.

The following examples are intended to illustrate certain embodiments of the present invention, but do not exemplify the full scope of the invention.

EXAMPLE 1

This example demonstrates that attenuation of lasing action in a chemically-sensitive, optically-pumped polymer thin film can be a sensitive probe for detecting airborne analytes. The change in the lasing response can be over 100-fold more pronounced than the attenuation of the spontaneous emission response, which may increase the detection sensitivity by a comparable factor. In this example, sensitivity gains were demonstrated in detection of explosive vapors such as 2,4,6-trinitrotoluene ("TNT") and 2,4-dinitrotoluene ("DNT"). Both TNT and DNT introduced non-radiative pathways in the polymer thin film, which attenuated lasing. The increased optical losses upon analyte detection resulted in the cessation of the lasing action. The sensitivity enhancement can be very pronounced for lasing polymer films pumped at intensities near the lasing threshold. Additionally, this example illustrates the development of a TNT-sensitive polymer with relatively high thin film quantum yields of >85% and relatively high optical damage thresholds. This example also shows low lasing thresholds of about 185 nJ/cm$^2$ for 30 nm thick polymer films in ambient atmosphere, and about 30 nJ/cm$^2$ thresholds for similar films deposited on substrates patterned with distributed feedback gratings. The sensitivity gains via the lasing mechanism produced enhanced sensitivity for fast detection of trace analytes such as explosive vapors.

Semiconducting organic polymers are an important class of luminescent sensor materials due to their ability to self-amplify. Their signal gain has its origins in the facility of these materials to transport excitons, which allows the short-lived excited states to visit a multitude of potential analyte binding sites. The detection of 2,4,6-trinitrotoluene and 2,4-dinitrotoluene using semiconductor polymer thin films enables the detection of buried landmines based on an explosive vapor signature. DNT is a synthetic byproduct of the manufacture of TNT and is often present in landmines containing TNT. The vapor pressure of DNT is much higher (about 100 ppb) than TNT (about 5 ppb). Thus, in some cases, DNT can be used to detect a buried mine even though it is less than 10% of the explosive component of a buried landmine. In TNT/DNT detection, the signal, fluorescence quenching is the result of the interaction between these nitroaromatic compounds (TNT or DNT), an electron-deficient pi-acid, and an electron-rich semiconductive polymer (FIG. 1). This quenching of emission may be the result of causing the polymer to reach ground state i.e., TNT/DNT charge transfer complexes may give rise to non-radiative states within the band gap, and electron-transfer from the organic polymer excited state to a bound TNT/DNT state. In some cases, rapid back-electron transfer may return the polymer to its ground state.

Figure 2:
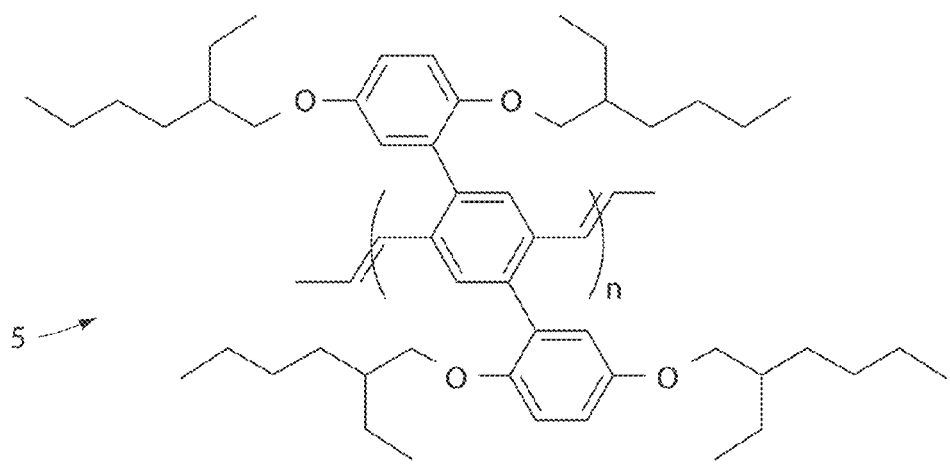
FIG. 2 is a chemical structure of a polymer of an embodiment of the invention.
Figure 11:
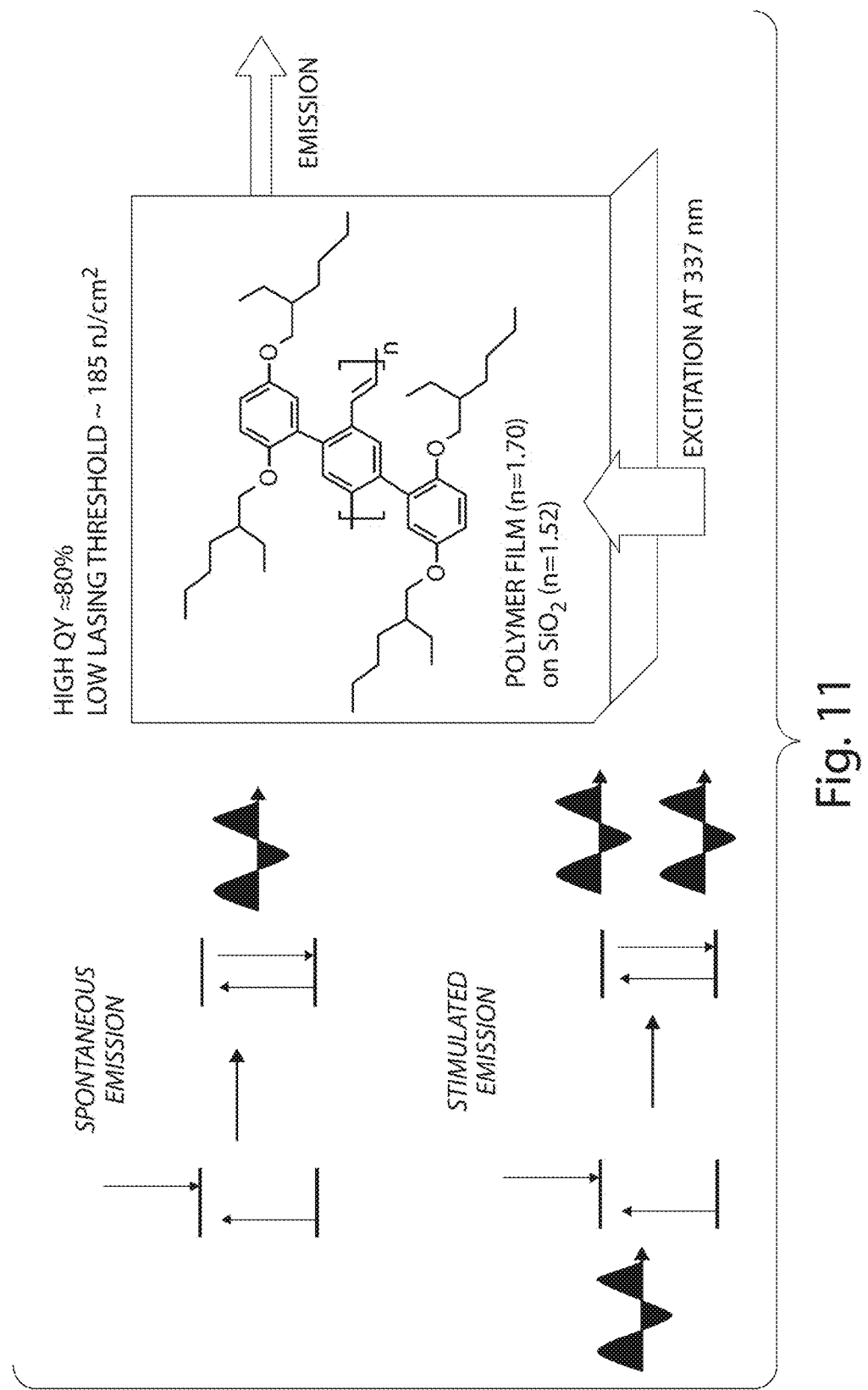
FIG. 11 is a schematic diagram showing excitation of a polymer of one embodiment of the invention.
Figure 12:
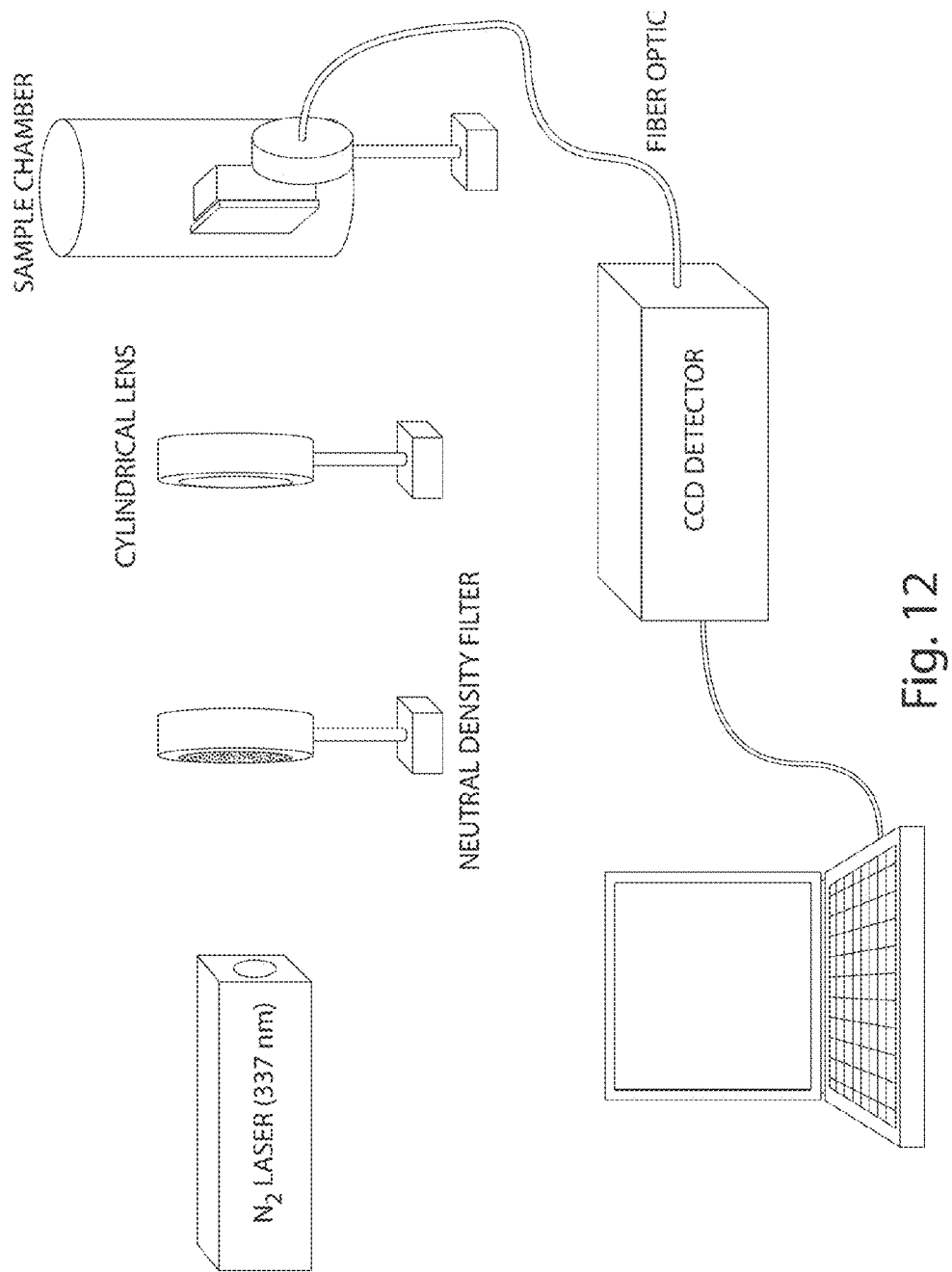
FIG. 12 is a schematic diagram of a detection system of an embodiment of the invention.
Figure 13:
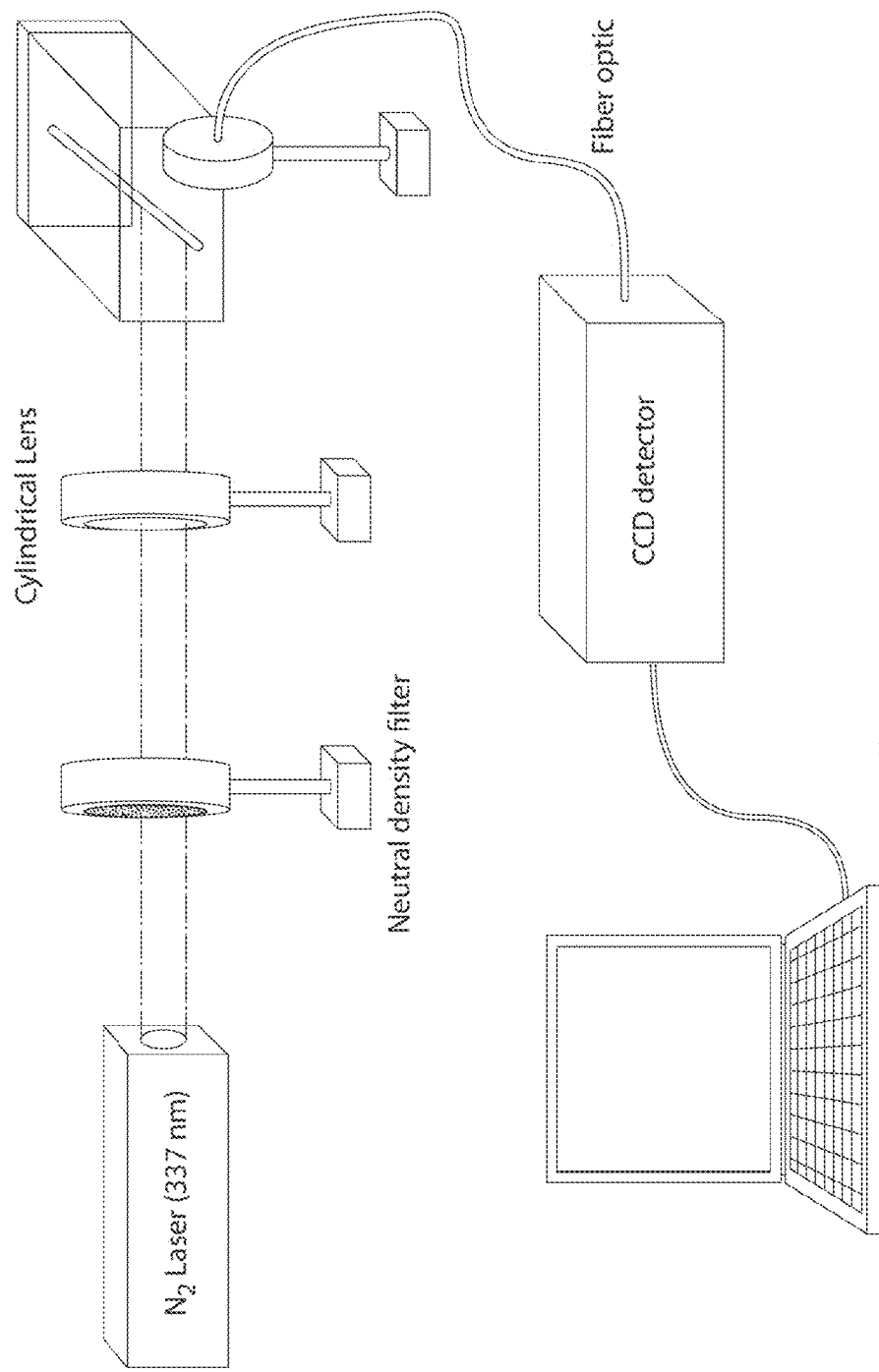
FIG. 13 is a schematic diagram of a detection system of another embodiment of the invention.

In this example, polymer 5 of FIG. 2 was used to demonstrate a lasing amplification scheme in SOPs ("semiconductive organic polymers"). Schematic diagrams of the experimental apparatus used in this example are shown in FIGS. 11-13. Polymer 5 is generally photophysical, stabile, and is also sensitive to TNT and DNT, as discussed in this example. Its thin film luminescence spectrum peaks at $\lambda$ (lambda)=505 nm and has a radiative lifetime of $\tau$ (tau)=650 ps. The rapid radiative relaxation contributes to its high fluorescence efficiency in spun-cast thin films of $\Phi$ (Phi)=85%, measured by comparison to a standard of 9,10-diphenylanthracene in PMMA ($\Phi$ (Phi)=83%). The pendant aromatic rings were designed into this system to increase the optical cross-section, which may enhance both the absorption and emission efficiency. The specific substitution pattern of the pendant rings was chosen to bias the orientation of the hydrocarbon side chains parallel to the polymer backbone. The backbone of polymer 5 was effectively encapsulated in hydrocarbon, thereby preventing strong interpolymer associations that typically lower the emission efficiencies. Furthermore, the resistance of polymer 5 to photobleaching can be attributed to this protective sheath of hydrocarbon chains. The extended pi-orbital interactions in polymer 5 created a band structure that can facilitate exciton transport. Diffusion lengths of about 100 Å (angstroms) have also been measured.

The lasing action was generated by optically exciting thin films of polymer 5 with a 4 ns long nitrogen laser pulses ($\lambda$ (lambda)=337 nm) at an operating frequency of 30 Hz. The beam was focused into a 9 by 0.9 mm stripe, and emission collected at a 60° angle from the excitation beam, which was incident normal to the substrate. All experiments were performed in air.

Simple asymmetric waveguides (FIG. 3A) were formed by spin casting thin films of polymer 5 from 50 mg/mL hexane solution onto glass substrates, with film thickness ranging from about 300 Å (angstroms) to about 4000 Å (angstroms). For films thicker than about 500 Å (angstroms), a multimode amplified stimulated emission (ASE) peaked at $\lambda$ (lambda) =535 nm, coinciding with the first vibronic transition (0,1) of polymer 5. The selective emission from this mode may be governed by the reabsorption of the (0,0) emission within the thin films.

Given that the exciton diffusion length normal to the film surface can be estimated to an order of 100 Å (angstroms), for sensitivity in a TNT/DNT sensory device, film thicknesses of the order of about 100 Å (angstroms) may be needed in some cases. Such thin films, however, may not be able to support waveguided optical modes of the laser structure. TNT/DNT exciton quenching of the surface molecules may be overshadowed by the unattenuated emission of the bulk, which may severely limit sensitivity. As a solution, in this example, glass substrates were coated with a roughly 2000 Å (angstroms) thick layer of optically transparent parylene by chemical vapor deposition and then spin cast thin polymer overcoats of polymer 5 (FIG. 3B). Parylene's refractive index of n=1.67 generally matched the refractive index of the polymer n=1.70, so that two in combination could form a waveguide. In these structures, ASE emission was observed for polymer layers as thin as 400 Å (angstroms). These films were found to be able to detect DNT, in part due to DNT's higher vapor pressure and penetration depth.

Comparisons of the emission intensities at 500 nm and 535 nm of a roughly 600 Å (angstroms) thick film of polymer 5 on parylene as a function of input power revealed the onset of ASE for the 535 nm mode to be about 80 nW. This corresponded to a threshold energy of about 190 $nJ/cm^2$. Typical measured thresholds ranged from about 190 $nJ/cm^2$ to about 4100 $nJ/cm^2$, depending on film quality and age, and the thresholds were easily reproducible. At these low input powers, signal attenuation due to photobleaching exposure was minimized, and for short exposure times could be neglected.

EXAMPLE 2

To further lower the ASE threshold, a distributed feedback (DFB) structure was prepared in this example, as shown in FIG. 3C, with an in-plane periodic reflection matched to the green light of the lasing emission. By facilitation of ASE, the DFB improved device stability by lowering the required optical pumping power, which reduced the photo-oxidation processes. The optical confinement also reduced the need for larger optical densities of the active polymer and thereby allowed for lasing in layers of polymer 5 that were thinner than the exciton diffusion lengths for enhanced sensitivity.

DFB structures were fabricated from PDMS and overcoated with polymer 5 applied by conventional spin-coating with a thickness of about 400 Å (angstroms) The lasing threshold was found to be further reduced (FIG. 4) as compared to structures lacking a DFB. The resulting threshold reduction was about a factor of 3 compared to a similar film on glass.

Figure 4:
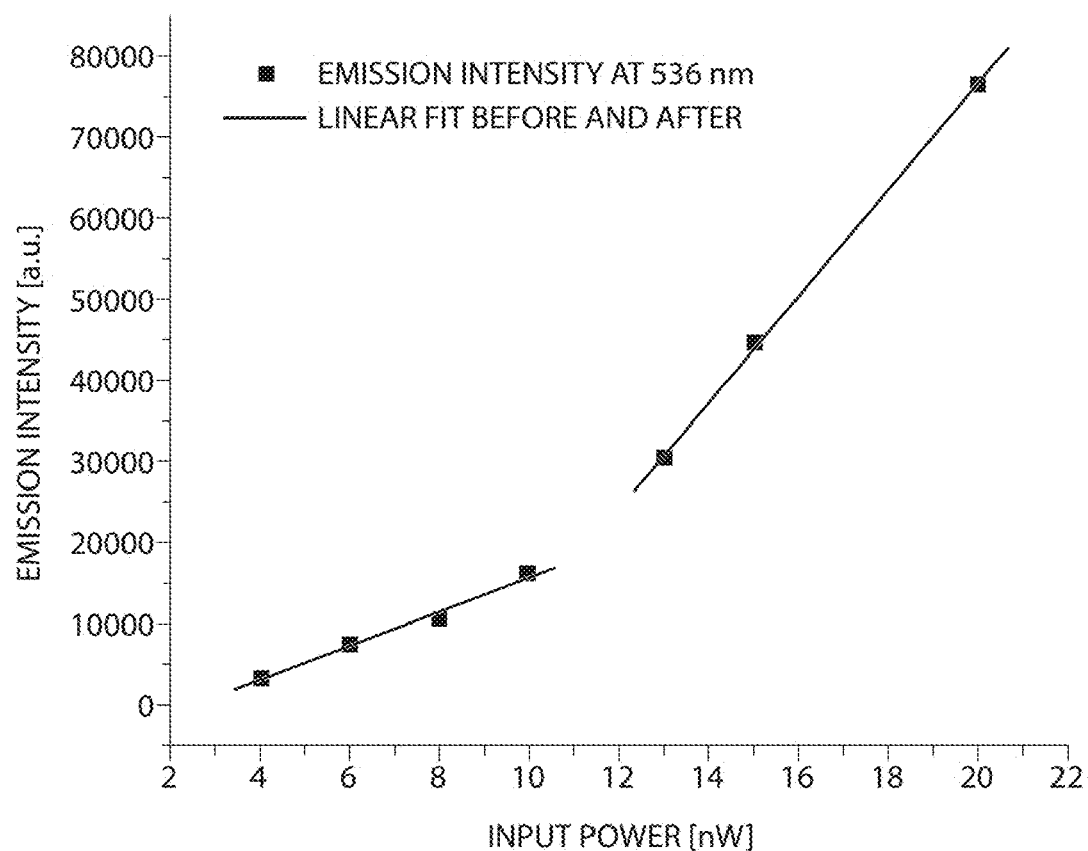
FIG. 4 is a plot of emission intensity vs. input power, according to one embodiment of the invention.

FIG. 4 shows a low lasing threshold of polymer 5 atop a PDMS DFB structure. In FIG. 4, the emission intensity of stimulated peak (536 nm) was a function of the input power. The lasing threshold was approximately at 12 nW with same spot size used on glass and paralene structures.

Figure 5A:
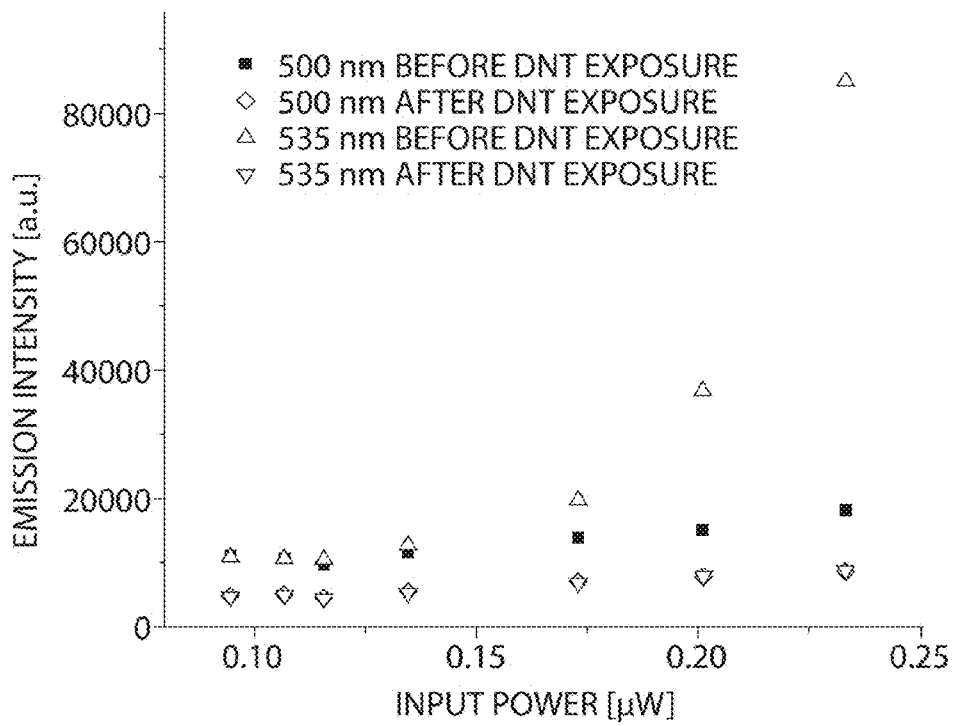
FIGS. 5A-5B are plots of spectral responses of certain embodiments of the invention.
Figure 5B:
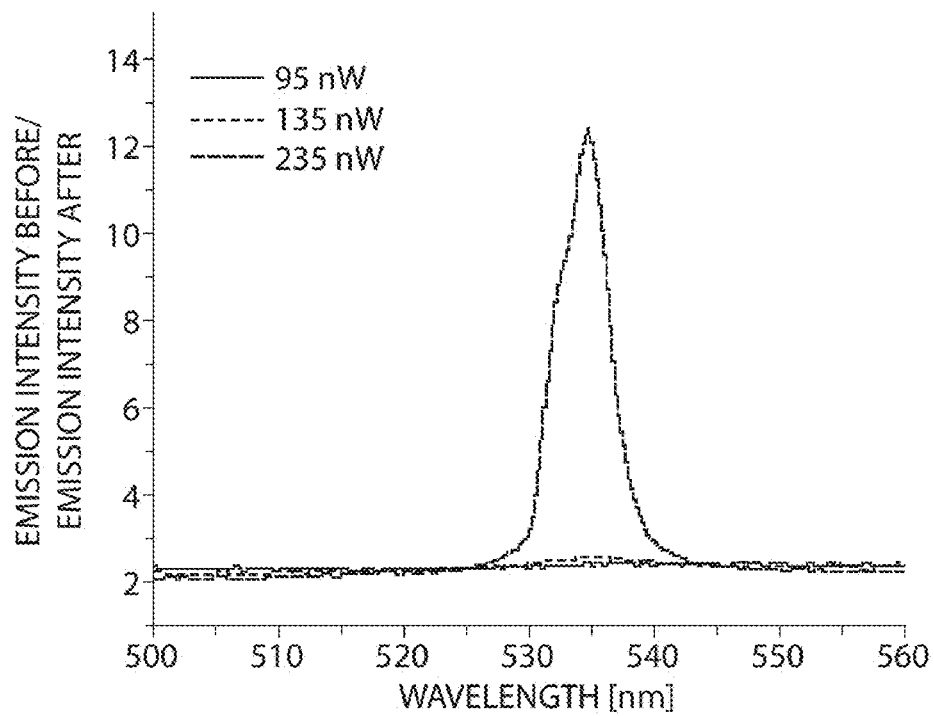

To measure the chemosensing response, paralyene/polymer 5 films were exposed to a static saturated vapor pressure of DNT in air. Two-minute exposures to saturated DNT vapor significantly decreased both the primary PL emission as well as the ASE observed at 535 nm from the first vibronic transition (FIG. 5A). The spontaneous emission peak at 500 nm had its emission intensity reduced by a factor of about 2. In contrast, the 535 nm peak had its intensity reduced by more than a factor of 10 for pumping power of about 230 nW (FIG. 5B). Depending on the power of the excitation beam, larger differential between exposed and unexposed sample can be registered.

FIG. 5 shows a spectral response of the optically pumped 750 Å (angstroms) film of polymer 5 on parelene coated glass before and after a 2 minute exposure to DNT. FIG. 5A shows emission intensity as a function of pump input power at 500 nm (corresponding to spontaneous emission) and at 535 nm (corresponding to ASE) before and after the DNT exposure. FIG. 5B shows emission spectra before exposure divided by emission spectra after exposure at 95 nW, 135 nW, and 223 nW input power. The largest signal was observed at lasing wavelength at highest input power.

Figure 6:
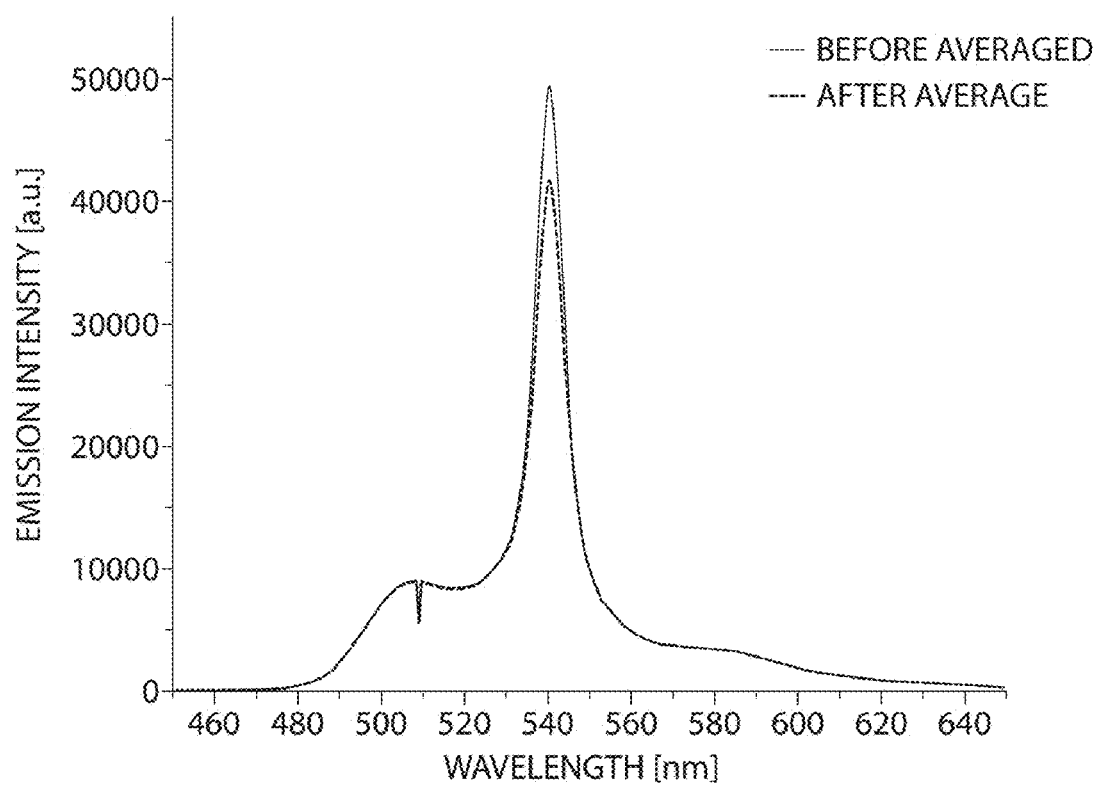
FIG. 6 is a spectral response plot of another embodiment of the invention.

Amplification due to exciton diffusion in SOPs was reduced at high quenching levels where multiple quenchers may be present in the diffusion path of the excitons. Similarly optimal sensitivities to ASE may arise close to the thresholds where small loses may provide maximal attenuation. To realize the optimal sensitivity to DNT with ASE, shorter DNT exposure times were investigated at a pump power of about 330 nW. When films were exposed to saturated DNT vapor (100 ppb) for 1 s, a significant attenuation in the ASE peak was observed. No measurable attenuation was concurrently observed in the spontaneous peak (FIG. 6). FIG. 6 shows ASE attenuation in the absence of spontaneous attenuation upon 1 s exposure to saturated DNT vapor pressure.

EXAMPLE 3

This example illustrates the use of dip-coated fiber optics to show an ASE with significantly thinner SOP coating layer. This device architecture may provide a significant response to DNT in some cases.

Samples were prepared by dipping a 25 micron diameter silica fiber into a methylene chloride solution of polymer 5 (1 mg/mL to 10 mg/mL). A thin polymer film was deposited upon controlled removal of the fiber cladding. The thickness was estimated by dissolving the material after analysis and measuring the absorbance of the resulting solution. The lasing action was generated in the same manner as the previous studies and the samples were exposed to a saturated vapor pressure of TNT for constant time increments.

Figure 7:
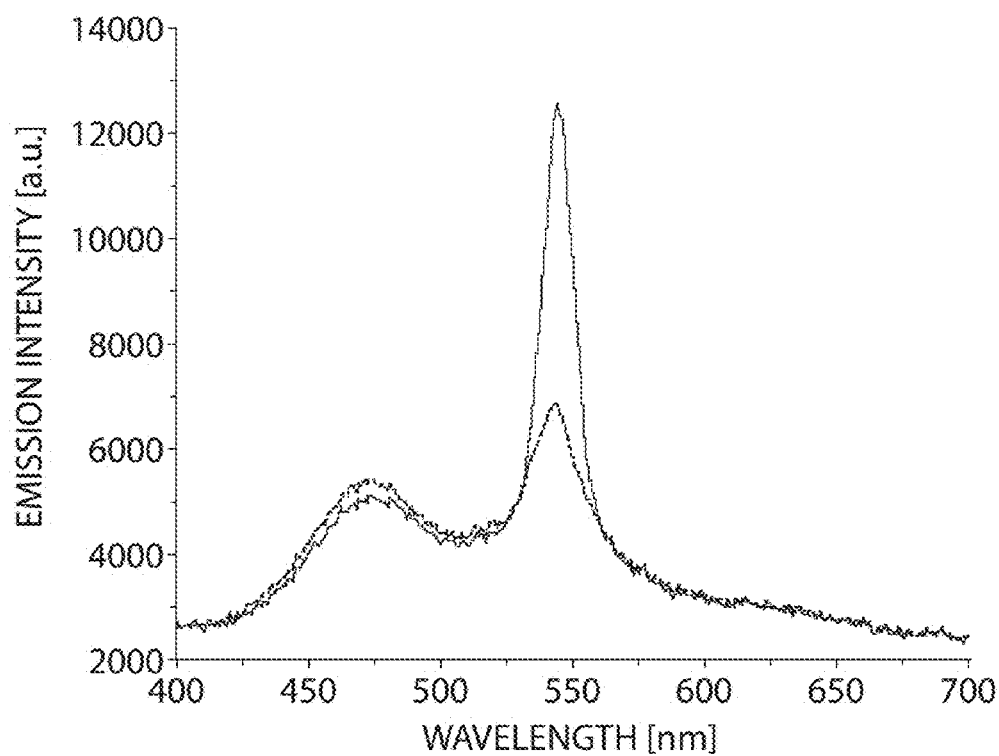
FIG. 7 is a spectral response plot of yet another embodiment of the invention.

In the coated fiber samples, unambiguous ASE attenuation was observed upon saturated TNT exposure for discreet time intervals while the spontaneous emission of the system remained constant (FIG. 7). FIG. 7 shows ASE attenuation in the absence of spontaneous attenuation upon 1.5 min exposure to saturated TNT vapor pressure. The lasing thresholds were higher in the fiber optic configuration due to a thinner active layer, so care was taken to ensure that photobleaching did not contribute to the observed signal. All spectra were averages of five different measurements to minimize the effect of pulse-to-pulse laser power fluctuations.

Figure 9:
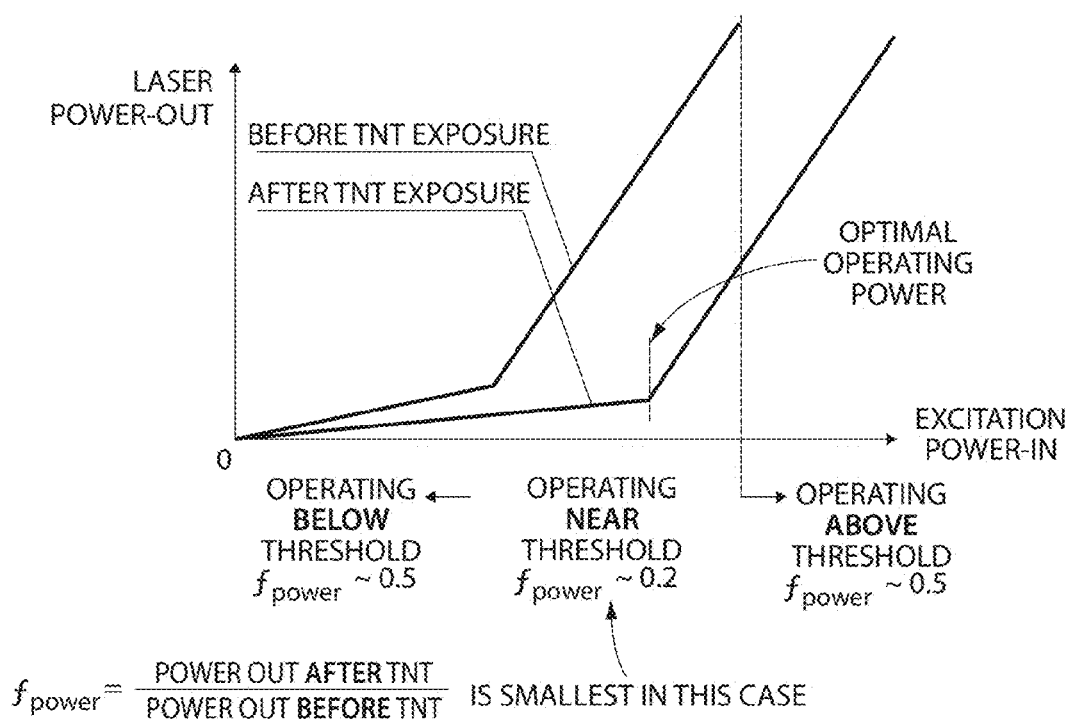
FIG. 9 is a schematic diagram showing laser power output vs. pumping power input, in accordance with an embodiment of the invention.

FIG. 9 shows laser power output versus pumping power input for a chemosensitive laser before and after analyte (in this case TNT) exposure. The biggest differentiation between the "before TNT" and "after TNT" signal was observed when the laser was initially pumped just above the threshold.

Figure 10:
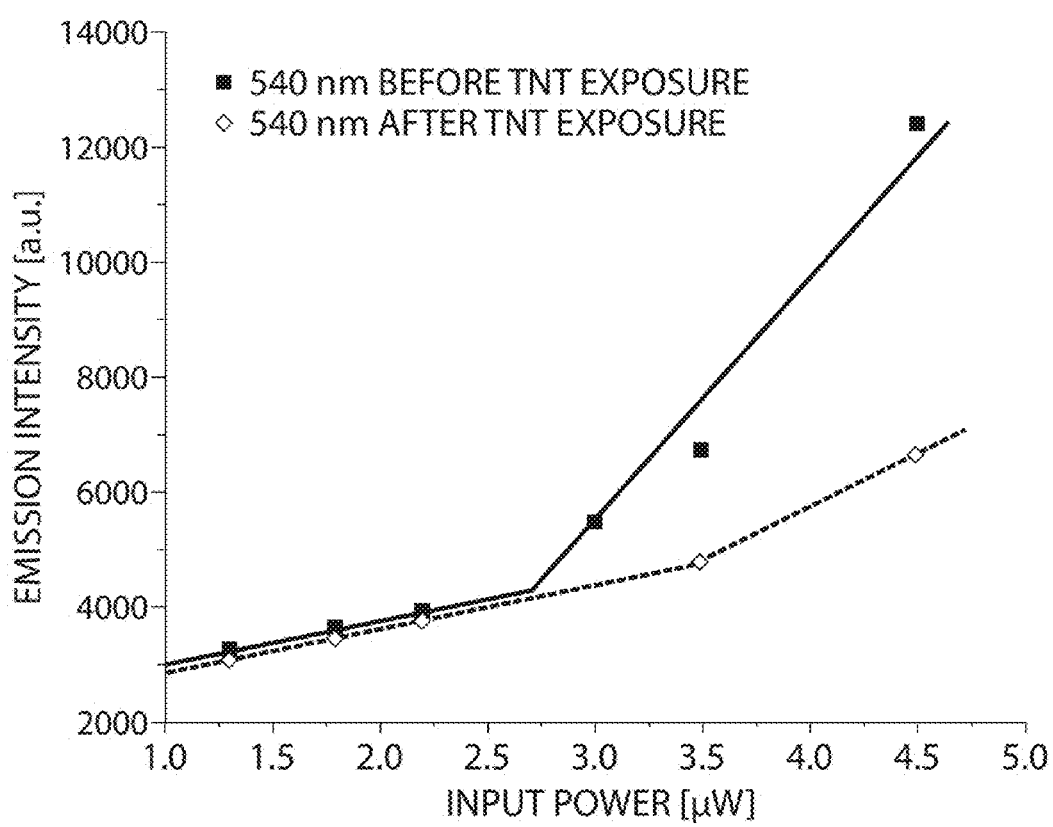
FIG. 10 is a plot of emission intensity vs. input power, in another embodiment of the invention.

FIG. 10 shows an ASE threshold increase upon 1.5 min exposure to saturated TNT vapor pressure at 540 nm.

EXAMPLE 4

Figure 8:
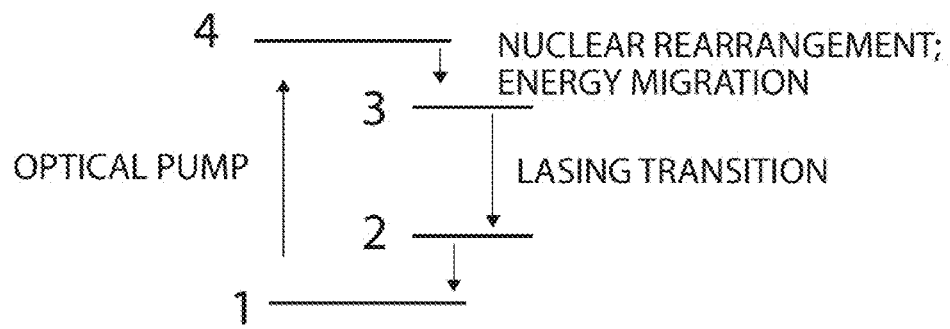
FIG. 8 is a schematic diagram of energy levels in an example of a conjugated polymer of the invention.

To better understand the impact of the quenching process on lasing action, this example modeled the laser electronic levels and excitation populations. Following the formalism previously proposed for lasing in organic solids, a four level system was used (FIG. 8), where the levels refer to: (1) the electronic and geometric ground state of the molecule, (2) the electronic ground state and the nuclear excited state, (3) the electronic excited state and nuclear ground state and (4) the electronic and nuclear excited state. The origin of levels 2 and 4 is based on the than the Franck-Condon principle, which states that electronic transitions occur more quickly than the internuclear distances relay to their equilibrium geometries.

For all organic materials, the Franck-Condon nuclear relaxation is accompanied by a red shift in the electronic transition energy, known as the Franck-Condon shift, thus justifying the treatment of these states as separate levels. In SOPs, there is an additional shift, which is further enhanced by the inherent disorder in the polymer backbone that creates a dispersion of the energy levels. In these materials excitons cascade from the higher energy states to the lower energy levels and thereby increase the Stokes shift. The 4-3 and 2-1 transitions are characterized by the rates $1/\tau_{43}$ (tau$_{43}$) and $1/\tau_{21}$ (tau$_{21}$) respectively. The transition from level 1 to level 4 occurs by optical pumping process, characterized by the rate R. The transition from level 3 to 2 occurs by one of four routes: spontaneous radiative relaxation (with rate $1/\tau_{sp}$ (tau$_{sp}$)), stimulated emission (with rate W), spontaneous non-radiative relaxation (with rate $1/\tau_{nr}$ (tau$_{nr}$)), and TNT quenching (with rate $1/\tau_{q}$ (tau$_{q}$)).

In general, the 4-3 and 2-1 transitions are much faster than any of the other transitions in the system, i.e., $$\tau_{43}, \tau_{21} \ll \tau_{sp}, \tau_{nr}, \tau_{q}, 1/W,$$

and so the pumping process was generally approximated as occurring directly into level 3 and the population in level 2 is generally assumed to be negligible. This yielded the following rate equation governing the population in level 3:

$$\frac{dN_3}{dt} = R - N_3 W - \frac{N_3}{\tau_{32}},$$

where $$\frac{1}{\tau_{32}} = \frac{1}{\tau_{sp}} + \frac{1}{\tau_{nr}} + \frac{1}{\tau_{q}}.$$

Since $N_2 \sim 0$, the population difference, N, is given by $N_3$. At equilibrium, the populations were constant, yielding:

$$N = R\left(W + \frac{1}{\tau_{32}}\right)^{-1}.$$

The population difference in the absence of lasing, $N_0$, was obtained by setting W to zero, yielding:

$$N_0 = R\tau_{32}$$

To achieve lasing, this population difference must increase beyond the so-called threshold population difference, $N_{th}$, which is the population difference at which point the gain due to stimulated emission equals the optical cavity losses.

The optical cavity losses were evaluated in this system, as the optical absorption at the lasing wavelength was negligible (due to the large Franck-Condon shift). Therefore only mirror losses contributed, and assuming a symmetric cavity, the distributed cavity loss coefficient, $\alpha$ (alpha), was obtained:

$$\alpha = \frac{1}{d}\ln\left(\frac{1}{\mathfrak{R}}\right),$$

where d is the cavity length and $\mathfrak{R}$ is the minor power reflectivity.

Prior to the onset of lasing, the photon flux present in the cavity at the lasing mode, $\phi$ (phi), is relatively small and so the effect of stimulated emission on the populations was small. The gain is this case, known as the "small-signal" gain, $\gamma_0$ (gamma$_0$), was given by:

$$\gamma_0(\nu) = N_0 \sigma(\nu),$$

where $\sigma(\nu)$ (sigma (nu)) was the stimulated emission transition cross section. (Note that the stimulated transition rate, W, is related to $\phi$ (phi) and $\sigma(\nu)$ (sigma (nu)) by $W = \phi\sigma(\nu)$.) Using the expression from above for $N_0$:

$$\gamma_0(\nu) = R\sigma(\nu)\tau_{32}.$$

The lasing threshold corresponds to the point at which:

$$\alpha = \gamma_0(\nu),$$

indicating that:

$$\frac{1}{d}\ln\left(\frac{1}{\mathfrak{R}}\right) = R\sigma(\nu)\tau_{32},$$

yielding a threshold pump rate, $R_{th}$, of:

$$R_{th} = \frac{1}{\sigma(\nu)d\tau_{32}}\ln\left(\frac{1}{\mathfrak{R}}\right).$$

From this expression, it can be seen that the introduction of TNT quenching modified the threshold of the laser through $\tau_{32}$ (tau$_{32}$) alone, since $\sigma(\nu)$ (sigma (nu)), d, and $\mathfrak{R}$ were all independent of the presence of TNT. Furthermore, since it has been shown that the presence of TNT does not alter the optical absorption of the polymer film, the relationship between the incident pump power and the pumping rate should remain unchanged as well.

Above threshold, the differential quantum efficiency of the laser is near 100%, meaning that every photon absorbed above threshold goes into the lasing mode. Therefore:

$$P_{laser} \propto P_{pump} - P_{th},$$

where $P_{th}$ is simply the pump power required to reach $R_{th}$. Since the pumping rate R is linearly proportional to the pump power (related by a constant determined by the film absorptivity), the change in $P_{th}$ following the introduction of TNT would be inversely proportional to the change $\tau_{32}$ (tau$_{32}$). In particular, the threshold pump power in the presence of the TNT quenching is given by:

$$P_{th}' = \beta P_{th},$$

and so, for the output power in the presence of the TNT quenching:

$$P_{laser}' \propto P_{pump} - \beta P_{th},$$

where $$\beta = \frac{\tau_{32}}{\tau_{32}'}.$$

This allows the sensitivity of the laser to be specified, in terms of the fraction change in the output power, $f_{power}$, $$f_{power} = \frac{P_{pump} - \beta P_{th}}{P_{pump} - P_{th}},$$

assuming that the sensor is operated using a fixed pump power. This is compared to the case of photoluminescence (PL) quenching, where $f_{power}$ is simply $\beta^{-1}$ (beta$^{-1}$)

The laser had the advantage that one can design a laser with a sensitivity disproportionate to $\beta^{-1}$ (beta$^{-1}$) by operating just above threshold. Consider the following example, where the TNT presence yields a $\beta$ (beta) of 2. If the laser is operated at twice the threshold, then the presence of the TNT brings the laser output down to zero, yielding a quench of 100%, compared to a PL quench of 50%. Therefore, the closer to threshold that the laser can be reliably operated the better the sensitivity. This can be seen in FIG. 9 for a hypothetical example and in FIG. 10 for a measured data set.

The influence of TNT exposure on lasing threshold is shown in FIG. 10. The above equations describe the quenching effects of TNT on the polymer-coated fiber optic. At higher input powers the difference in emission intensity before and after TNT exposure continues to increase. This allows one to gain much more quenching signal by increasing the input power. In some cases, however, with longer operating times (>1 min), the higher power may lead to photobleaching, which may interfere with the quenching response. However, in certain instances where greatest amount of signal is required, one may achieve this through increasing the input power while shortening operating lifetime of the active polymer film.

In conclusion, asymmetric waveguide structures were constructed using the polymers of the invention. Through optical pumping, ASE was readily observed at lower thresholds than any previously reported. Low thresholds are important in preventing photobleaching and hence, in some cases, devices using these polymers may be operated in ambient air. Significantly amplified responses were measured upon exposure of the polymer to saturated vapor pressure of DNT and TNT. Responses were measured in the lasing peak before any attenuation was observed in the spontaneous peak.

EXAMPLE 5

Figure 16A:
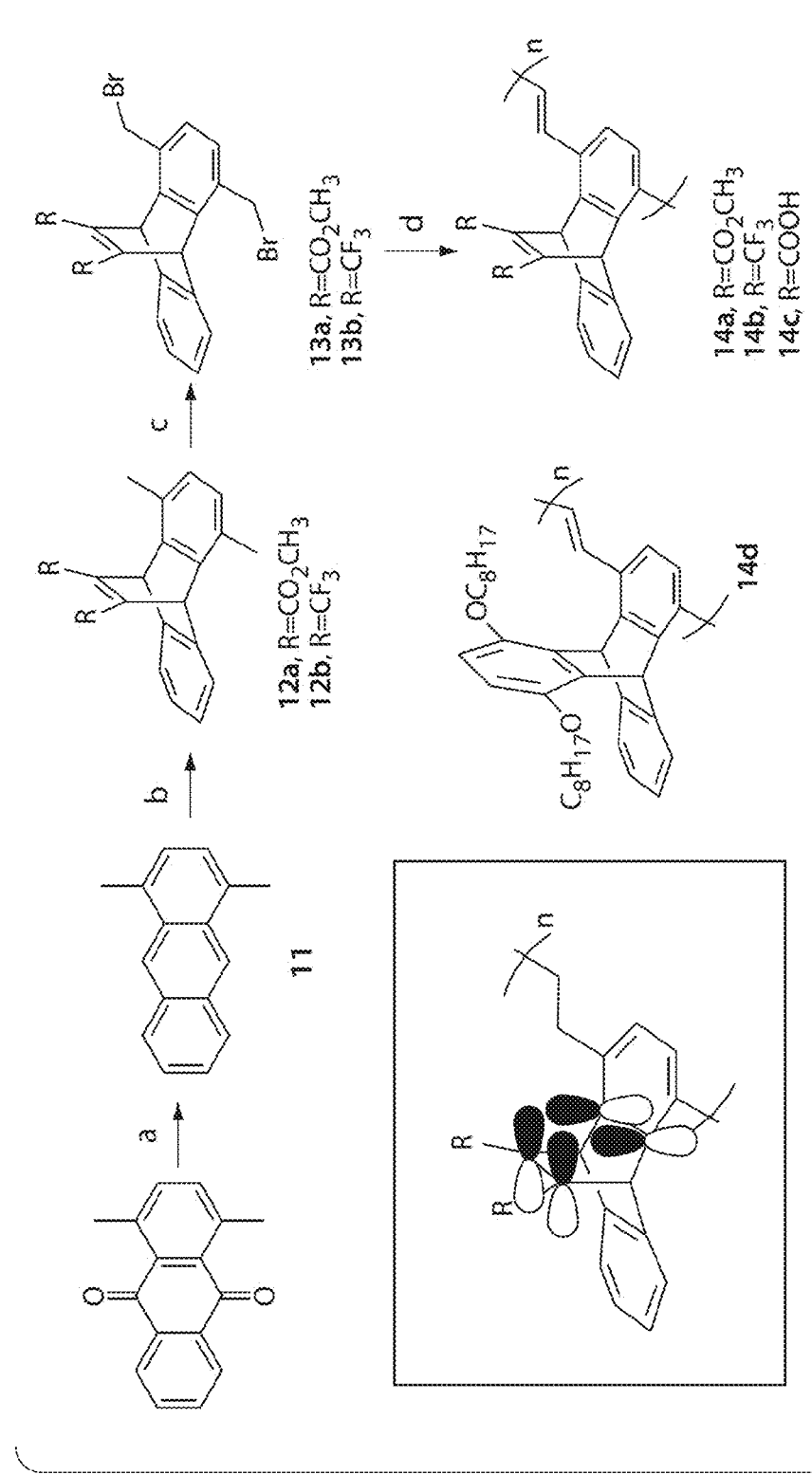
FIGS. 16A-16B illustrate the preparation of certain polymers potentially suitable for use in some embodiments of the invention.

This example illustrates a semiconducting polymer having electron withdrawing groups bonded to a non-conjugated portion of the polymer. To perturb the electronic structure of the conjugated polymer without interrupting conjugation by adding steric bulk in the plane of polymer backbone, a [2.2.2] bicyclic ring system containing an electron-deficient double bond that can interact with the polymer backbone in a hyperconjugative fashion was designed (FIG. 16A). FIG. 16A illustrates the synthesis of the [2.2.2] bicyclic ring poly (phenylene vinylene) ("PPV") compound. In this figure, (a) is NaBH$_4$, 2-propanol, reflux; (b) is dimethylacetylenedicarboxylate or hexafluoroacetylene, xylene, 140° C.; (c) is NBS, AIBN, CCl$_4$, reflux; and (d) KO$^t$Bu, THF, r.t.

Figure 16B:
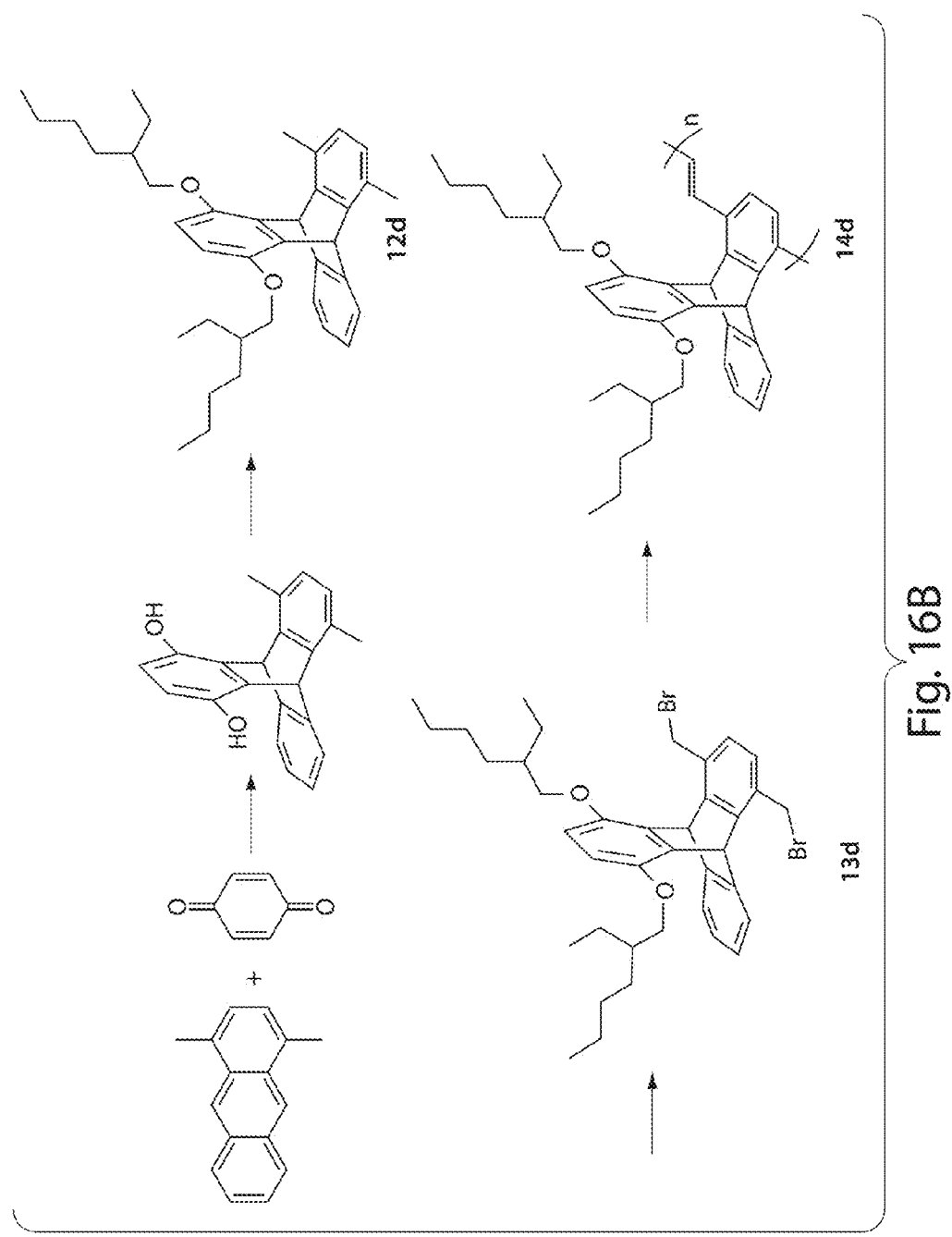

Compounds 13a and 13b, which each have at least one electron withdrawing group appended to the alkene of the bicyclic ring system, were synthesized and then polymerized by reaction with excess KO$^t$Bu to give polymers 14a and 14b (FIG. 16A). The ester groups in polymer 14a included both methyl and (30%) tert-butyl groups, with the latter being produced by transesterification under the polymerization conditions. The triptycene polymer 14d (FIG. 16B) represented an electron-rich model polymer for comparison with relative electron-poor polymers 14a and 14b. The absorption and emission maxima of polymers 14a and 14b were found to be similar (Table 1). High fluorescence quantum yields were observed for all of the polymers in THF solution and in thin films. The latter feature was attributed to the reduced interchain interactions enforced by the three-dimensional frameworks.

TABLE 1

| Polymer | GPC (Mn) | PDI | Abs $\lambda_{max}$ (nm) (log $\epsilon$) | Em $\lambda_{max}$ (nm) | $\Phi$ | $\tau$ (ns) |
|---|---|---|---|---|---|---|
| 14a (THF) | 1.2 × 10$^5$ | 2.5 | 401 (3.83) | 473, 498 | 0.58 | 1.16 |
| 14a (Film) | | | 401 | 507 | 0.42 | |
| 14b (THF) | 6.8 × 10$^4$ | 2.6 | 403 (3.48) | 471, 497 | 0.86 | 0.75 |
| 14b (Film) | | | 405 | 506 | 0.43 | |
| 14d (THF) | 7.9 × 10$^5$ | 2.1 | 413 (4.32) | 469, 499 | 0.76 | 0.62 |
| 14d (Film) | | | 414 | 477, 511 | 0.61 | |

EXAMPLE 6

Figure 17A:
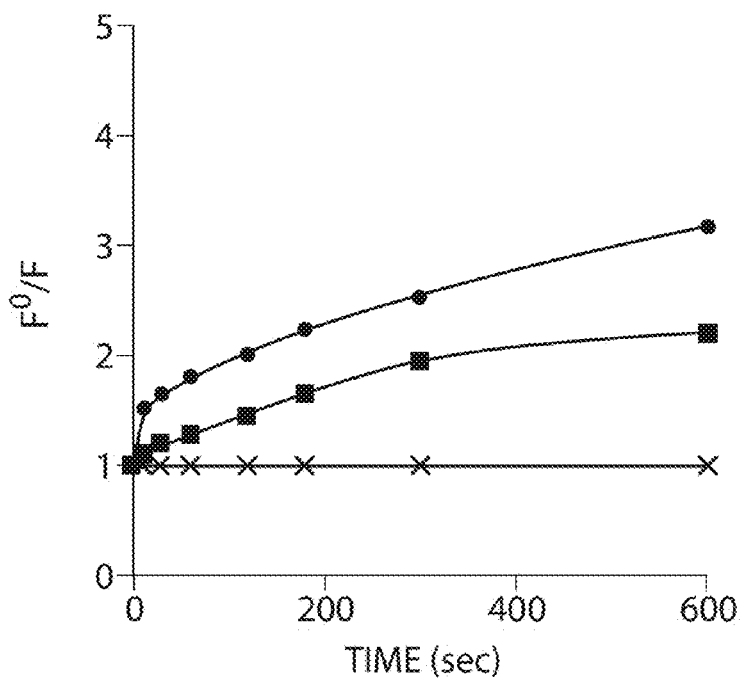
FIGS. 17A-17D illustrate various Stern-Volmer plots of certain polymers of the invention.
Figure 17B:
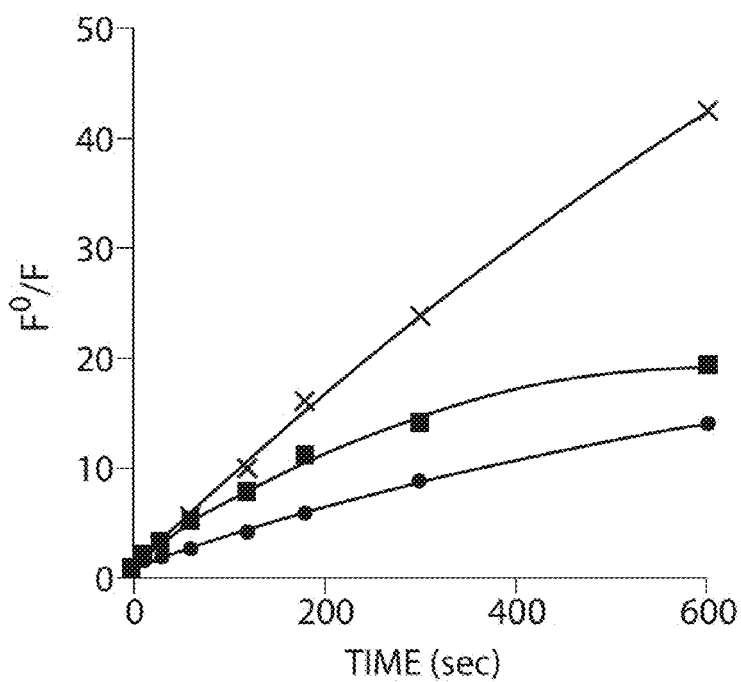

This example illustrates various fluorescence quenching studies, using polymers similar to those described in Example 5. The effect of hyperconjugative perturbations on the sensory properties was determined by investigating fluorescence quenching responses of thin films with exposure to vapors of electron-rich (N,N-dimethyl p-toluidine (DMT)) and electron-deficient (2,4-dinitrotoluene (DNT)) aromatic compounds. All of these thin films displayed the largest quenching response (FIG. 17A) to DNT, despite the fact that it had lower vapor pressure (1.47×10$^{-4}$ mmHg) than DMT (1.78× 10$^{-1}$ mmHg). This result may be due to the former's strong pi-acid character that favors association with electron-donating pi-electron systems. As shown in FIG. 17B, the relative quenching response of polymers 14a, 14b, and 14d reflected the expected hyperconjugative effects, with polymer 14b being the most oxidizing and polymer 14d being the most reducing. Hence, polymer 14b gave the strongest relative response to DMT and the weakest relative response to DNT. Correspondingly, polymer 14d displayed the opposite behavior, having a larger response relative to the other polymers to DNT and a weaker relative response to DMT. Polymer 14a exhibited responses intermediate to those of polymers 14b and 14d.

Figure 17C:
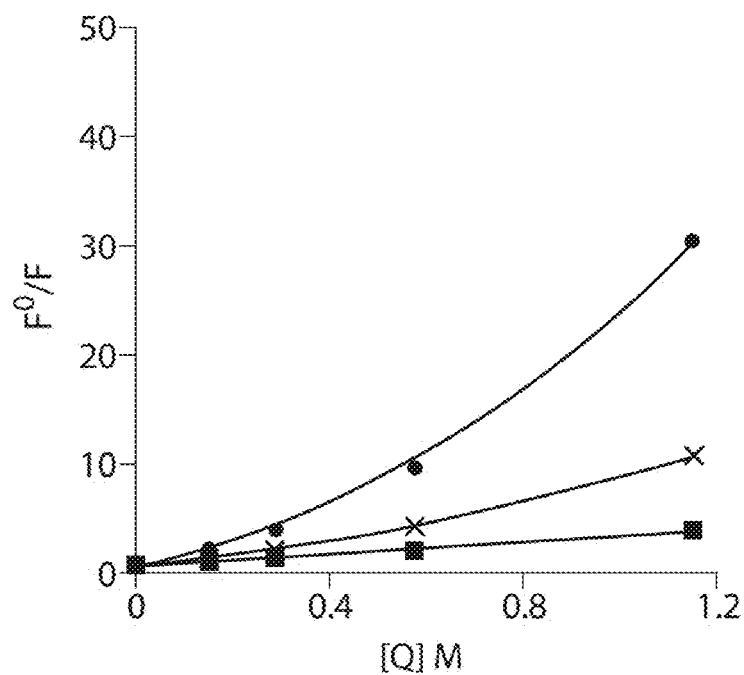
Figure 17D:
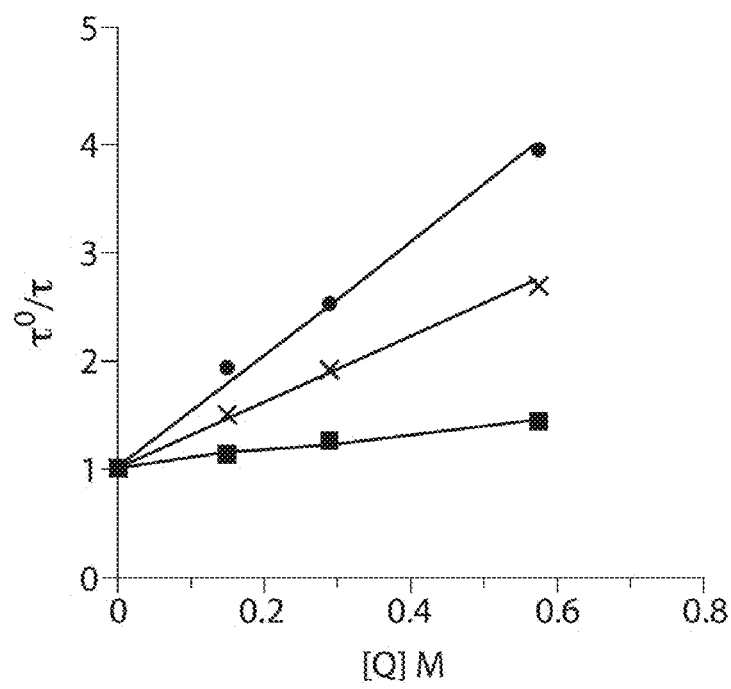

To further investigate the quenching behavior, solution Stern-Volmer quenching studies were conducted to determine the rates of static and dynamic quenching by performing steady state and time-resolved experiments (FIGS. 17C-17D). Static quenching, involving a preformed complex, did not reduce the excited state lifetime whereas dynamic quenching, resulting from diffusion, lowered the lifetime.

The trends in the solution Stern-Volmer rate constants, summarized in Table 2, contrasted markedly to those from the thin film studies. The electron-poor polymer 14b exhibited the largest quenching (both static and dynamic) with DMT (FIGS. 17C-17D). However, polymer 14d, the most electron-rich polymer, had a much higher diffusive quenching rate than diester containing polymer 14a. The deviations from thin film behaviors were even more pronounced with DNT quenching. In this case, polymer 14d exhibited the lowest static quenching ($K_{sv}$), even though it has the best sensitivity in thin films. These results underscore the fact that, in many cases, the sensory behaviors of conjugated polymers in solution can be very different than their responses in devices that often employ thin films. There are multiple origins for these differences, including different hydrodynamic volumes for each polymer that can be influenced by the analyte, steric effects that restrict the close approach of quenchers, and the degree of amplification by energy migration. For polymer 14d, its relatively lower solution sensitivity to DNT may be due to the steric bulk of its alkyl side chains, and as a result it may exhibit smaller static quenching than polymers 14a and 14b.

TABLE 2

| Polymer | Quencher | $K_D$ (M$^{-1}$) | $K_S$ (M$^{-1}$) | $k_q$ (M$^{-1}$s$^{-1}$) |
|---|---|---|---|---|
| 14a | DMT | 0.80 | 0.92 ± 0.58 | 6.9 × 10$^8$ |
| 14b | DMT | 5.19 | 2.49 ± 0.60 | 7.0 × 10$^9$ |
| 14d | DMT | 2.99 | 0.94 ± 0.67 | 4.8 × 10$^9$ |
| 14a | DNT | 11.00 | 86 ± 65 | 9.4 × 10$^9$ |
| 14b | DNT | 7.60 | 108 ± 93 | 1.0 × 10$^{10}$ |
| 14d | DNT | 8.00 | 25 ± 15 | 1.3 × 10$^{10}$ |

EXAMPLE 7

Figure 18A:
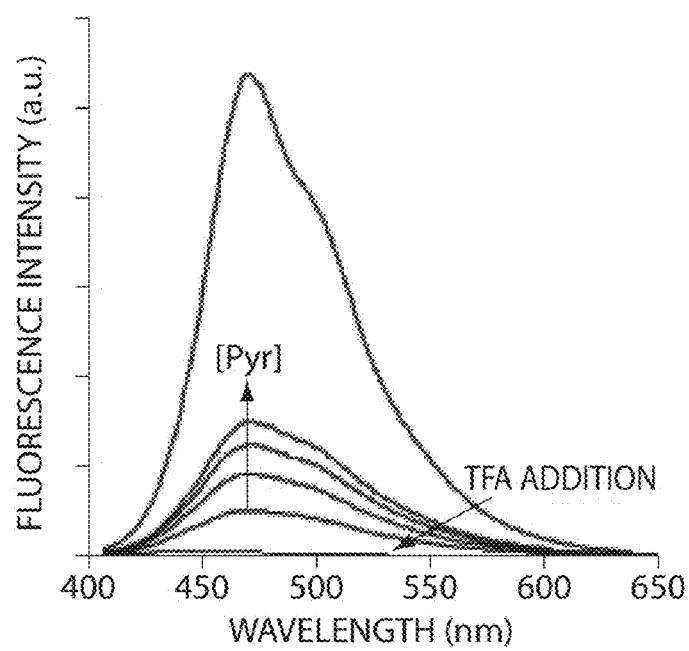
FIGS. 18A-18B illustrate various emission spectra of certain polymers of the invention.
Figure 18B:
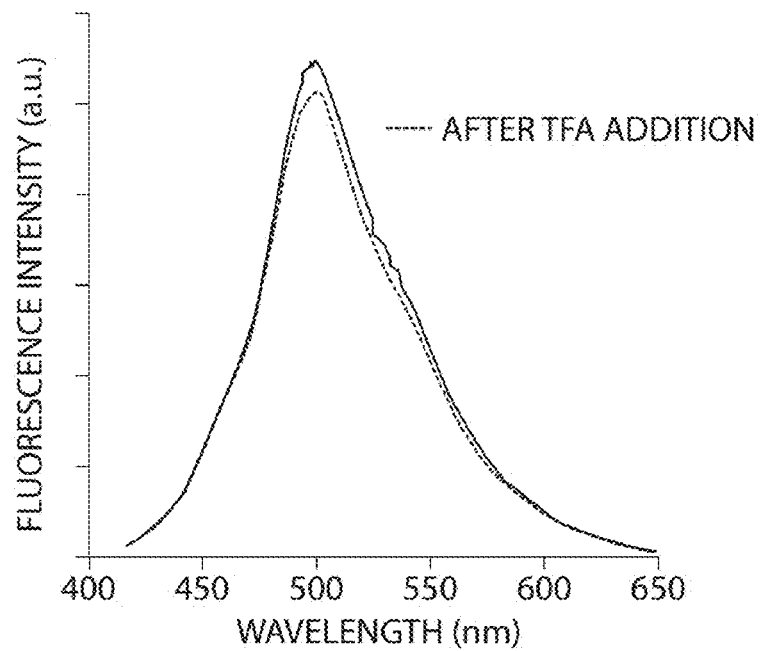

This example illustrates the acid-base response of certain PPV polymers which may be suitable for use in the present invention. Emerging sensor applications of certain conjugated polymers may require conjugation to biorecognition elements. In this example, the stability of polymers 14a and 14b to conditions associated with solid phase peptide synthesis was tested. Conjugated polymers often may exhibit reactivity with strong electrophiles such as trifluoroacetic acid ("TFA"). However exposure of polymer 14b in CH$_2$Cl$_2$ (methylene chloride) solutions of TFA or immersion of solids in neat TFA resulted in no apparent reduction/modification of its emission. Three drops of trifluoroacetic acid was added to 1 cm quartz cuvette containing polymers 14a and 14b dissolved in CH$_2$Cl$_2$ at room temperature, respectively, and their emission spectra were observed. In the case of polymer 14a, the fluorescence spectra were recorded with the increase of concentration of pyridine added to the CH$_2$Cl$_2$-TFA suspension of polymer 14a (FIGS. 18A-18B). Methylene chloride solutions containing polymer 14a were quenched with the addition of TFA; however, its fluorescence appeared to be immediately and completely recovered without any spectral shift after neutralization with pyridine. Aqueous acid treatment of polymer 14a lead to the hydrolysis of both ester groups to give polymer 14c. Polymer 14a may also be readily modified with amide or glycol moieties, which are of interest from the standpoint of biocompatibility.

EXAMPLE 8

Figure 19A:
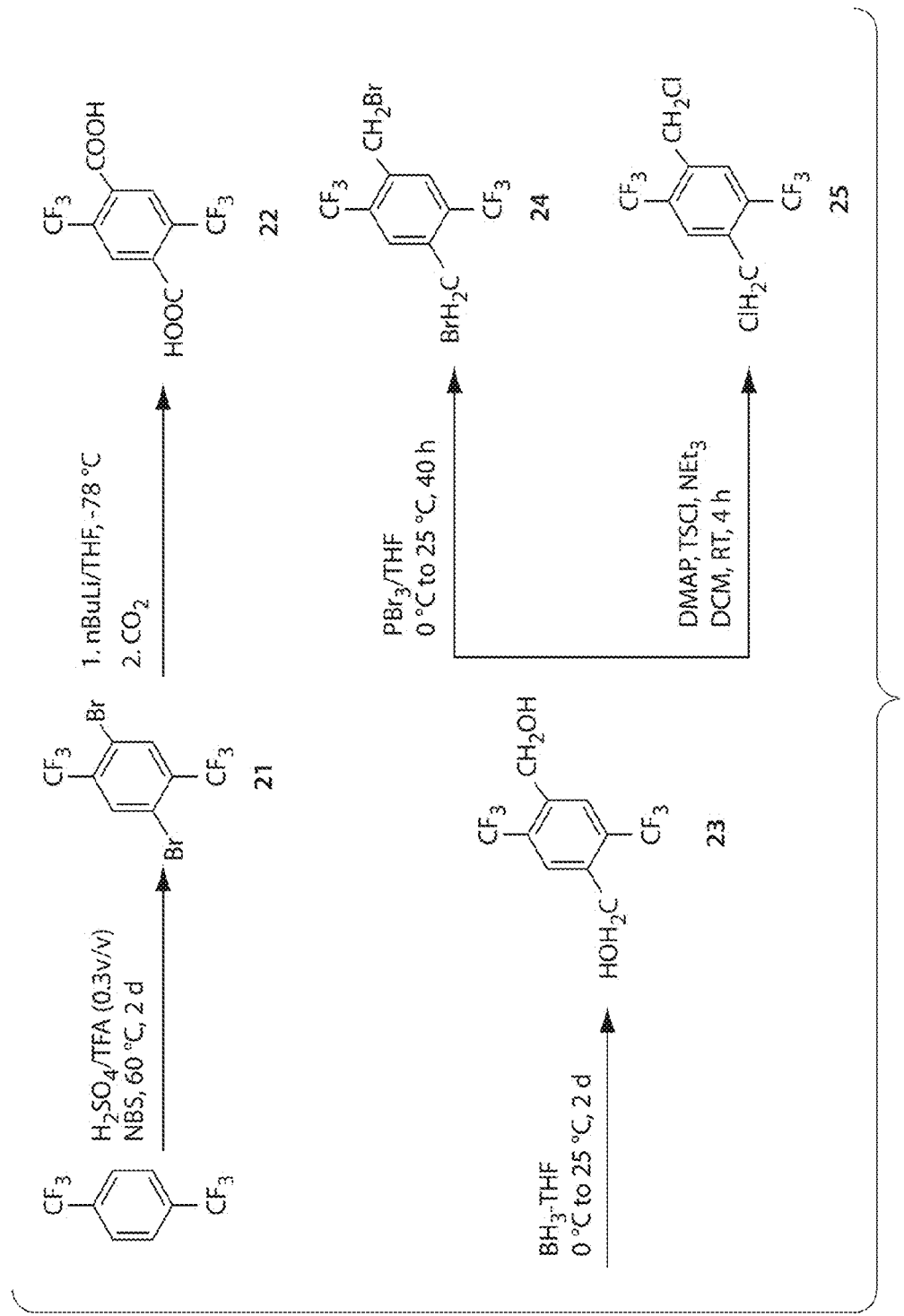
FIGS. 19A-19N illustrate certain reaction pathways useful for preparing certain polymers of the present invention.
Figure 19B:
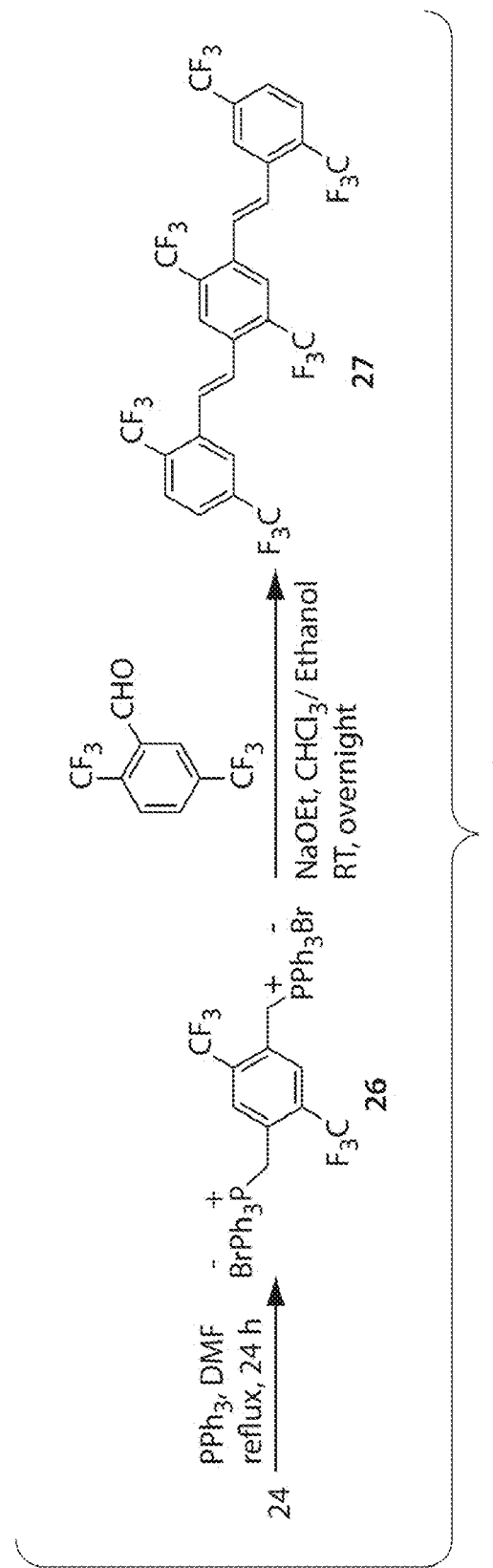
Figure 19C:
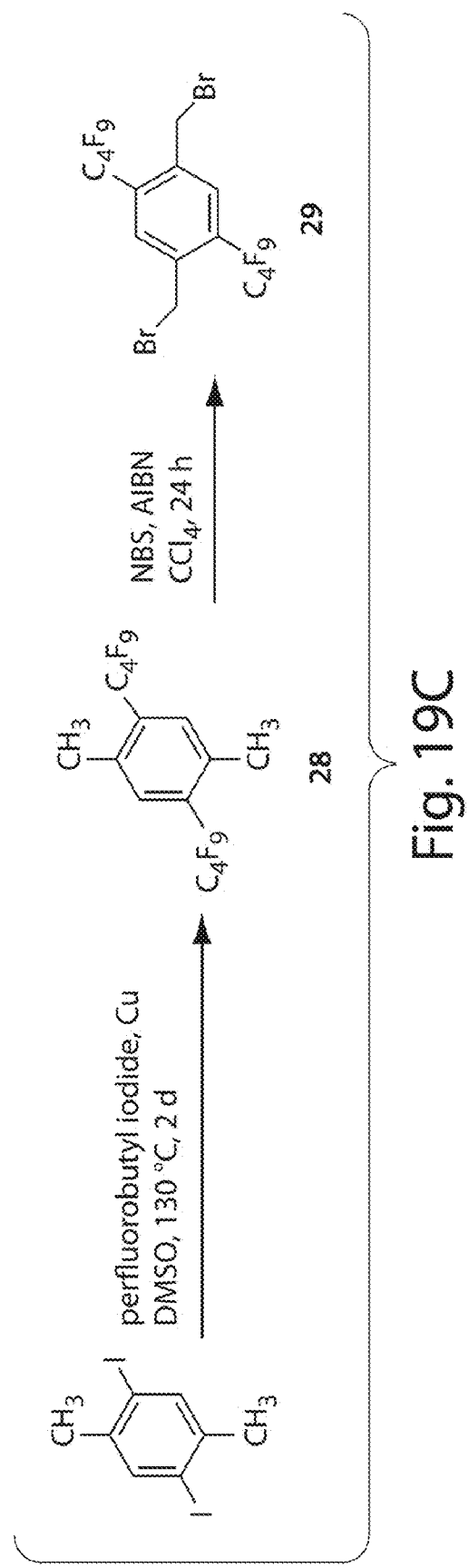
Figure 19D:
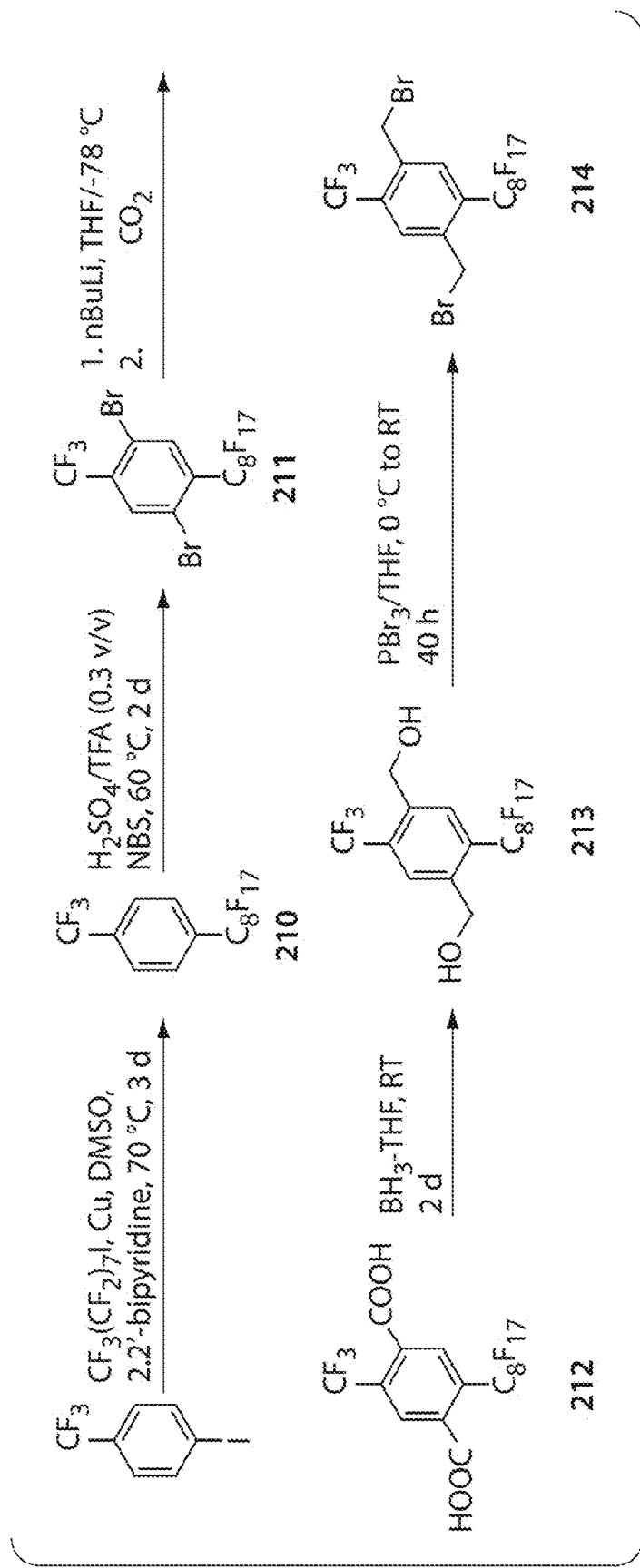
Figure 19E:
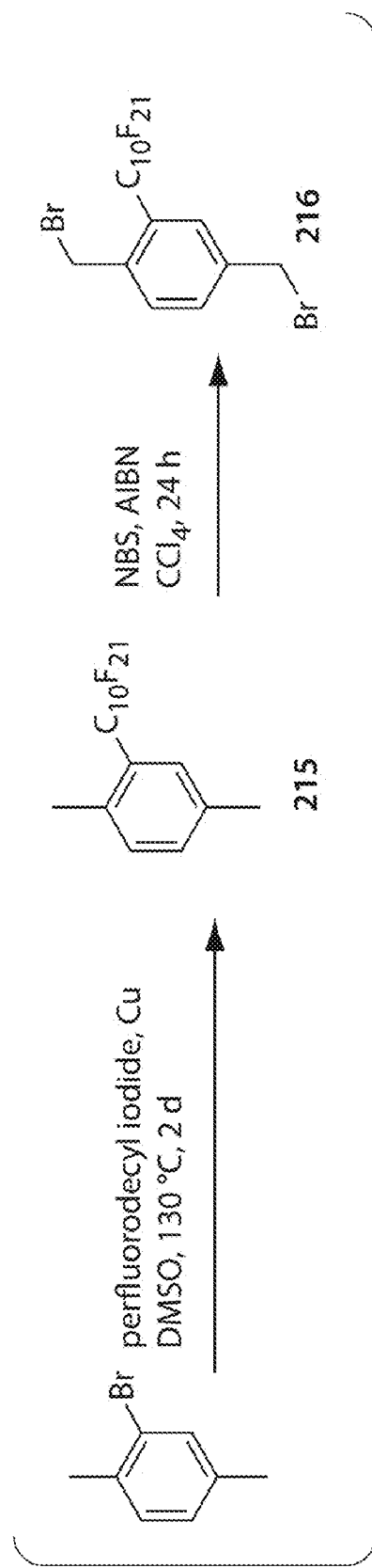
Figure 19F:
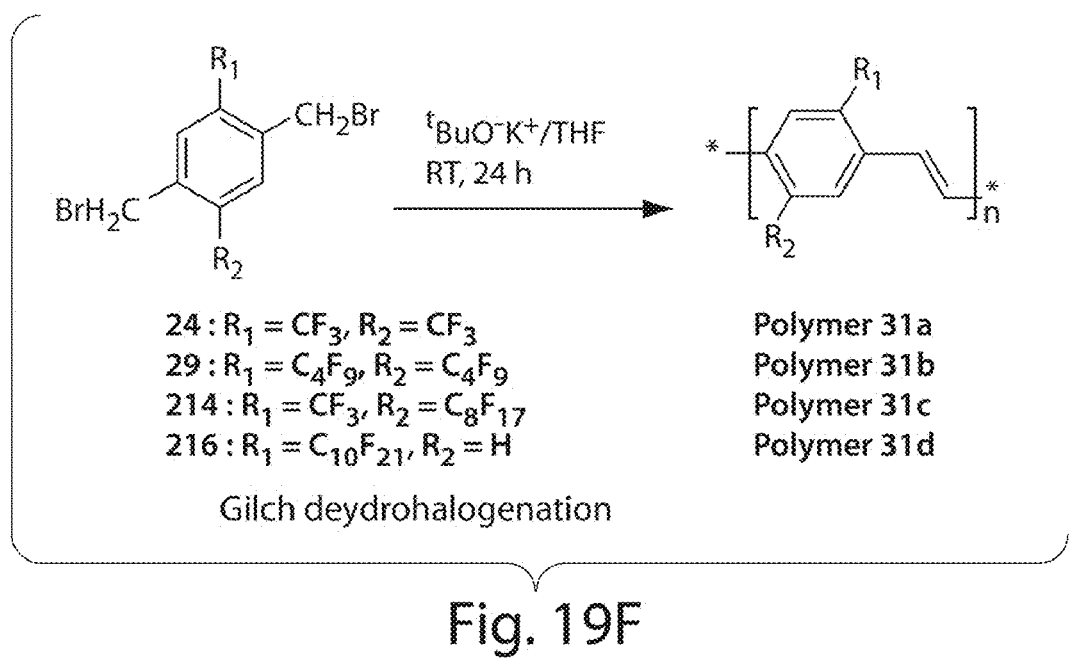
Figure 19G:
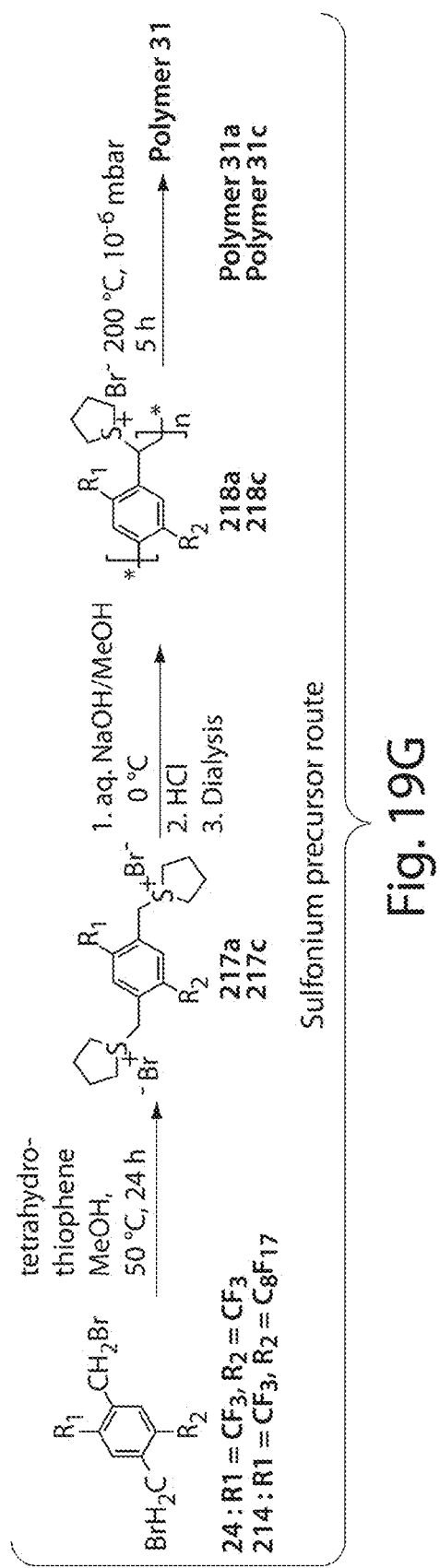
Figure 19H:
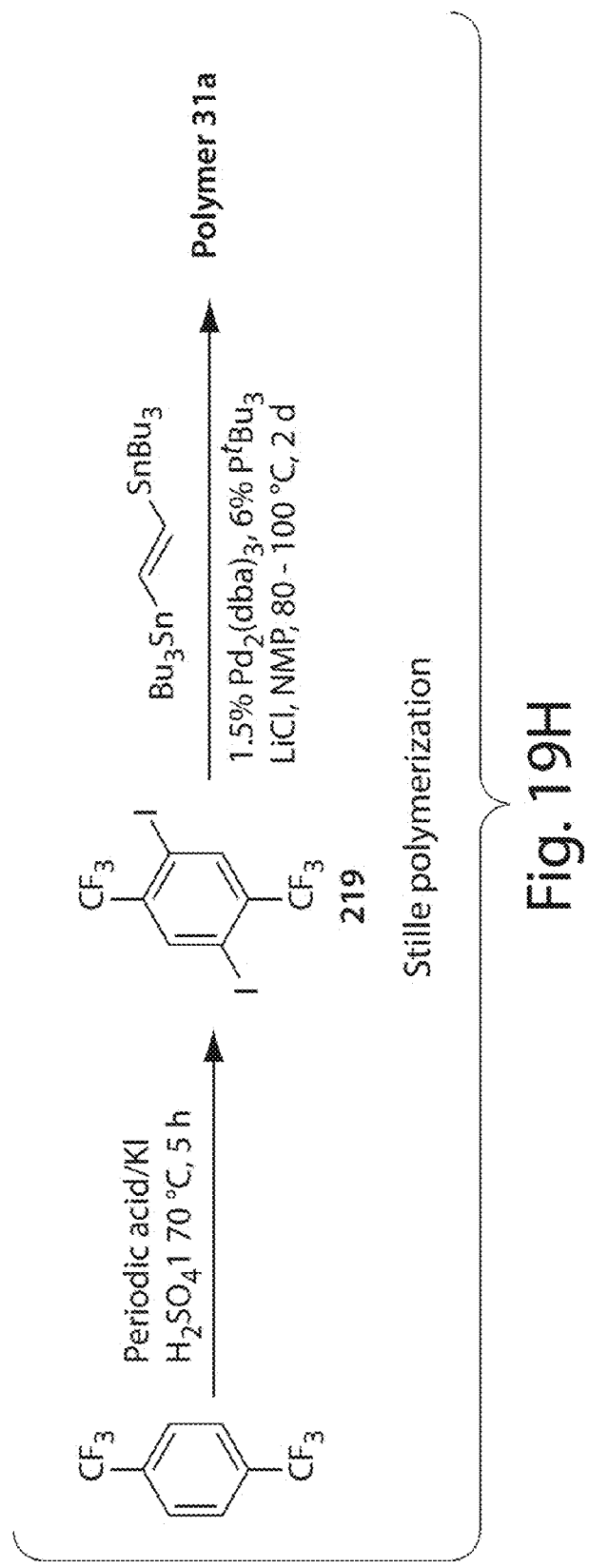
Figure 19I:
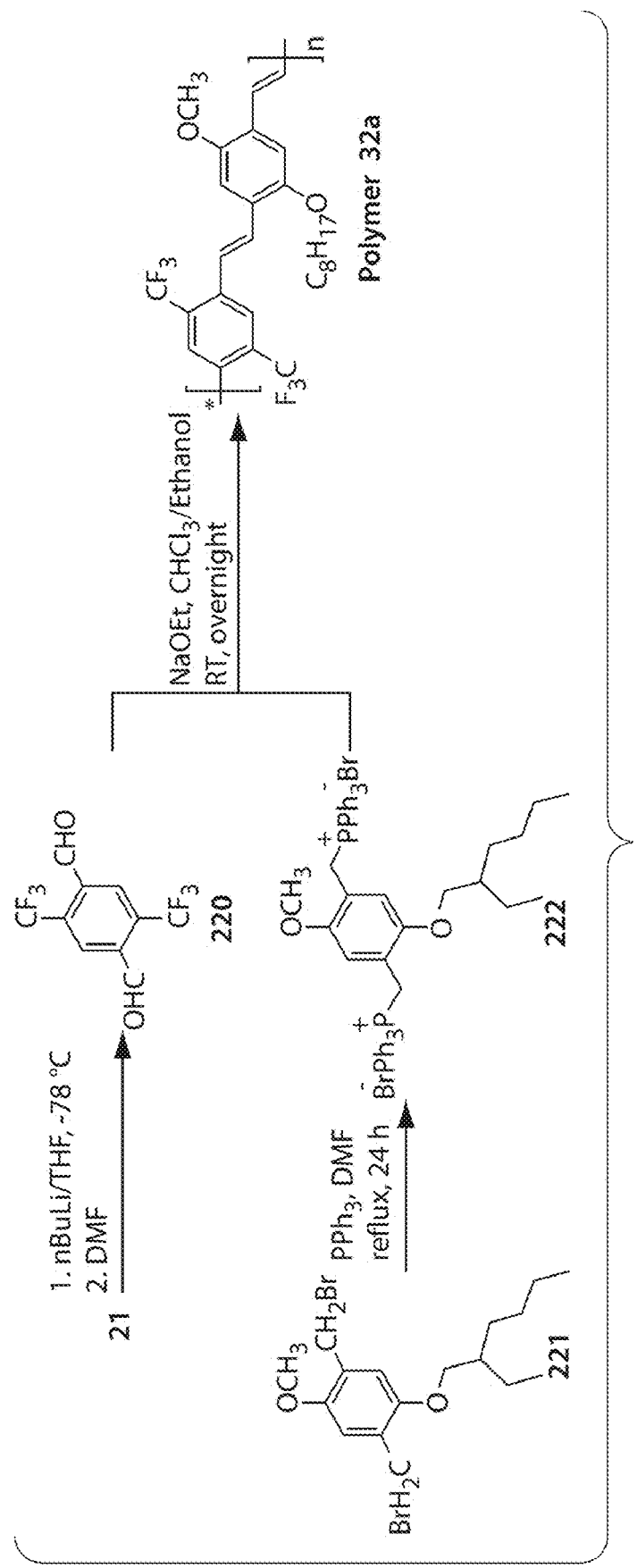
Figure 19J:
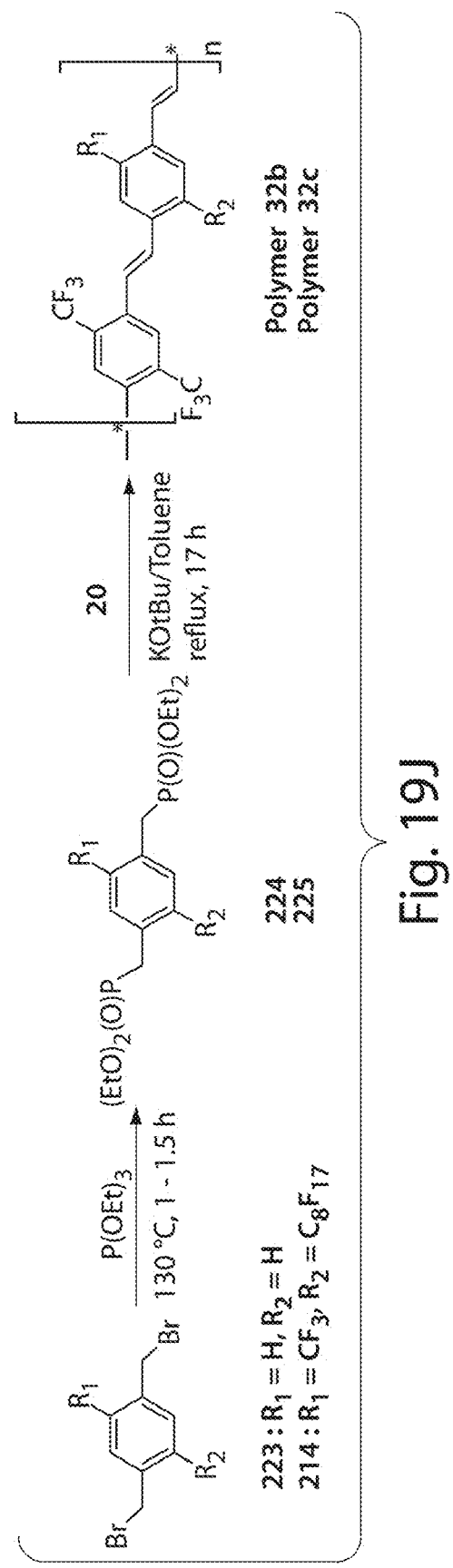
Figure 19K:
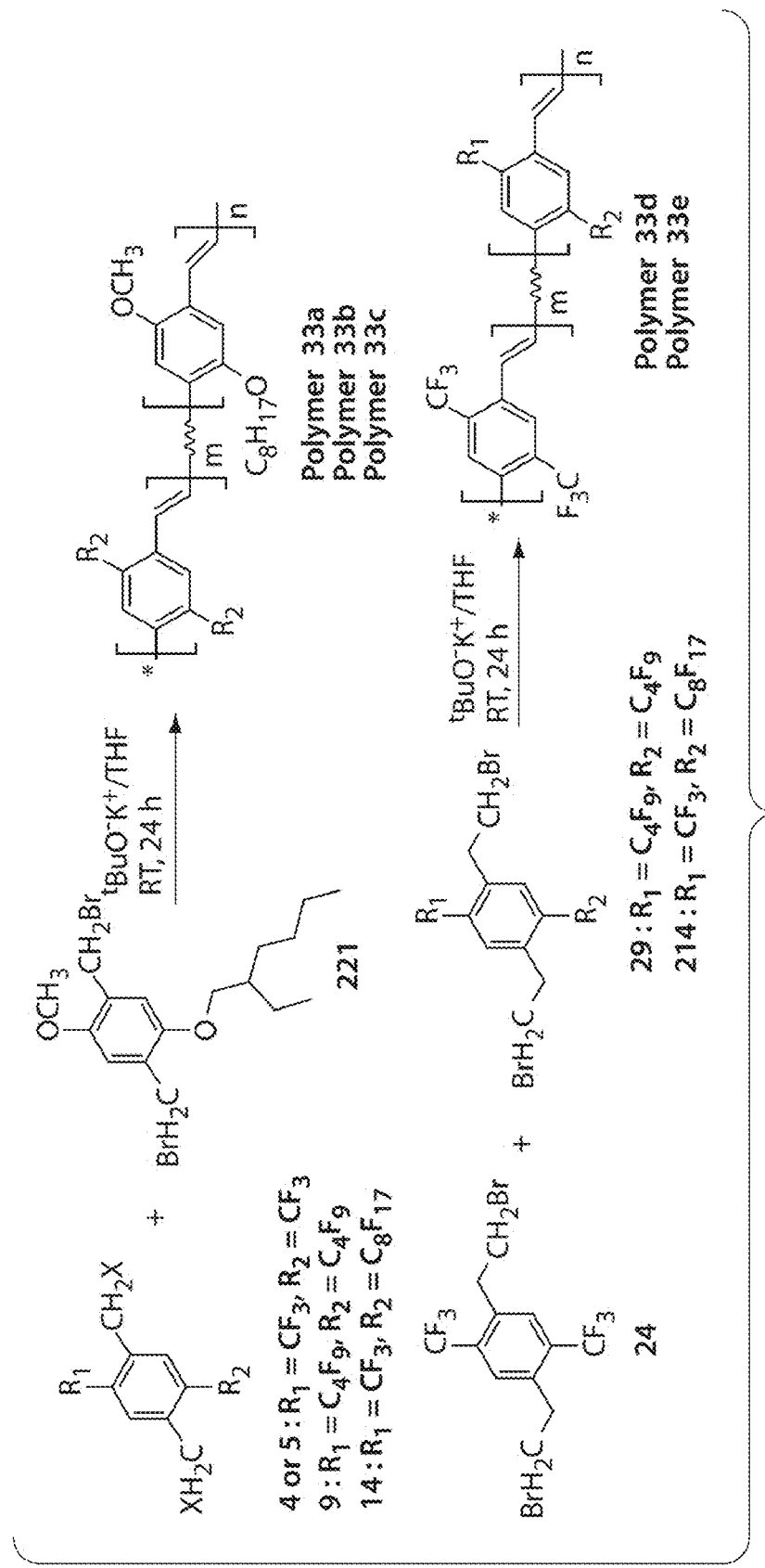
Figure 19L:
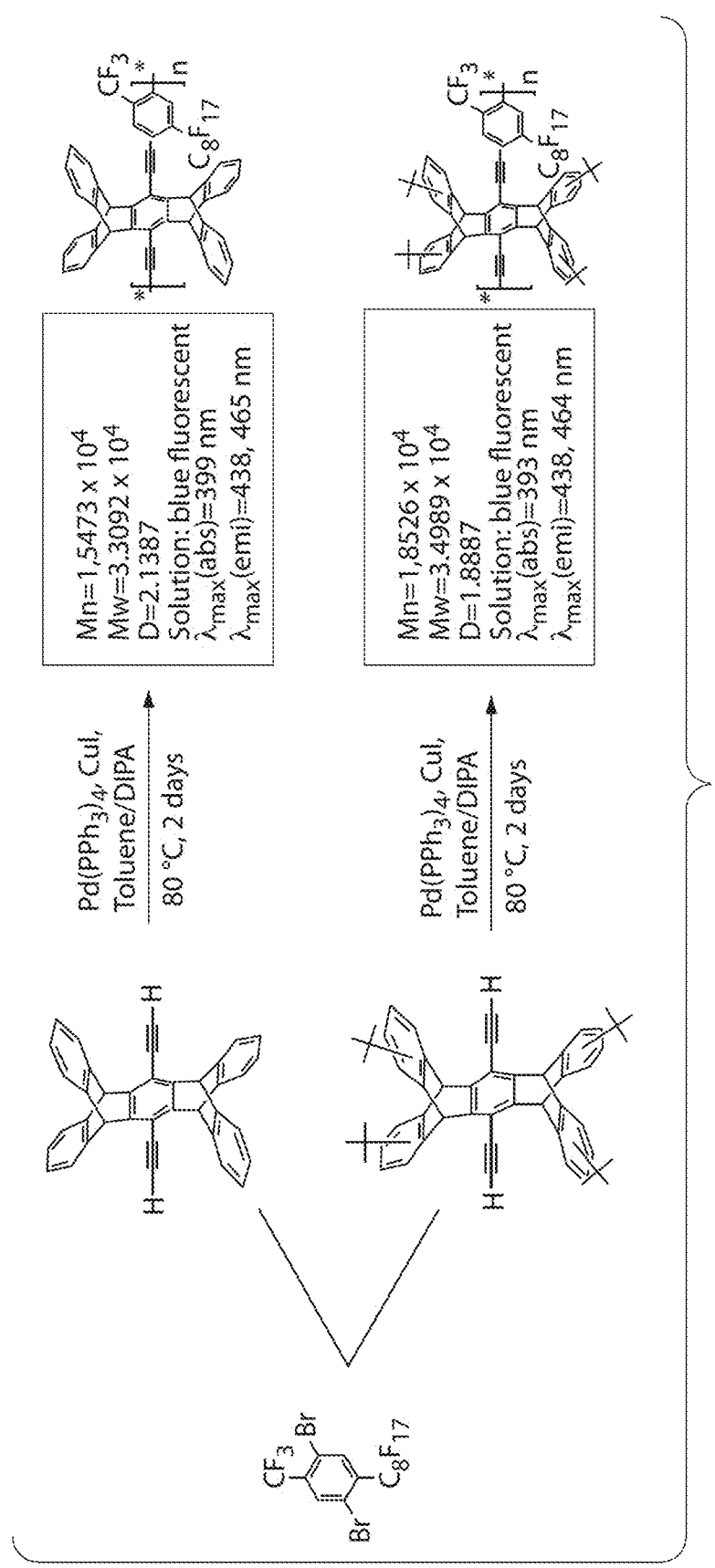
Figure 19M:
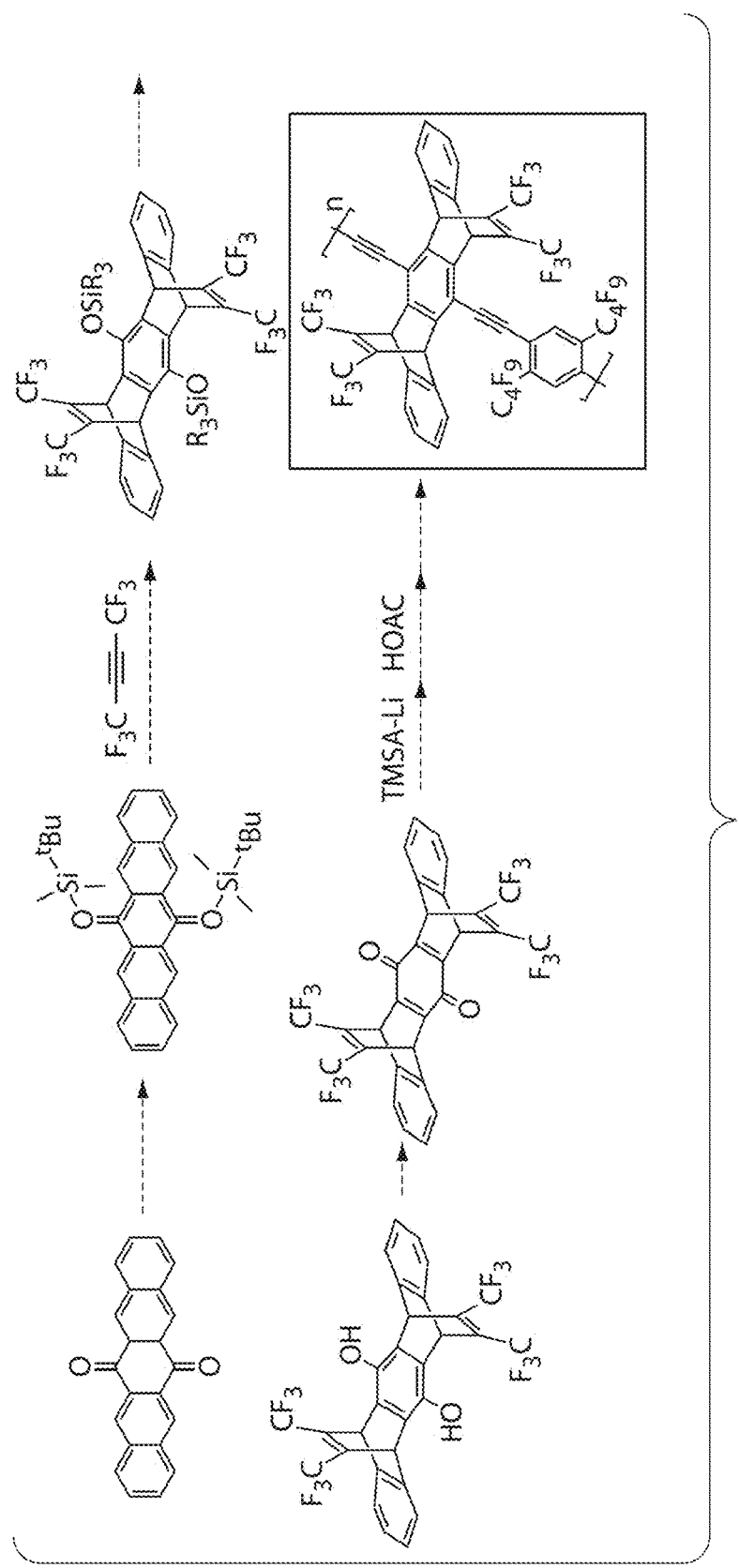
Figure 19N:
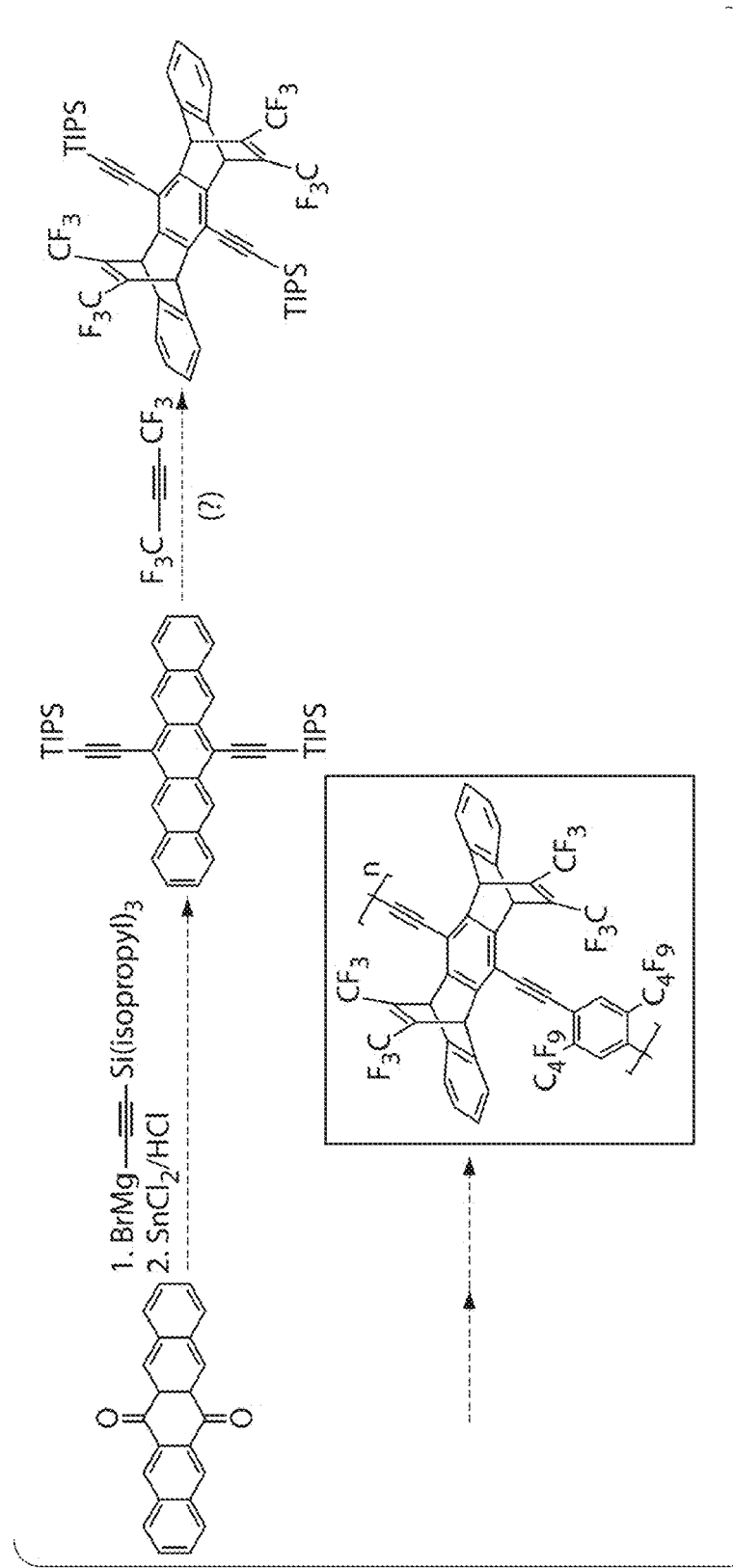

This example illustrates the synthesis of various semiconducting PPV polymers having electron withdrawing groups bonded directly to the conjugated backbone. The starting materials used in this example are known or can be prepared by known processes from commercially available materials. The products of the reactions described herein are isolated by conventional means such as extraction, crystallization, distillation, chromatography, and the like. The synthetic procedure is illustrated in FIGS. 19A-19N, where the electron withdrawing group is a perfluorinated alkyl.

EXAMPLE 9

This example demonstrates the stability of certain PPV polymers comprising perfluorinated alkyls. Semiconductive polymers containing perfluorinated alkyls have a high electron affinity that may prevent oxidative degradation (photobleaching). The photobleaching studies described in this example revealed that the perfluoroalkyl semiconductive polymers had superior stability, when compared to other semiconductive organic polymers.

Figure 14:
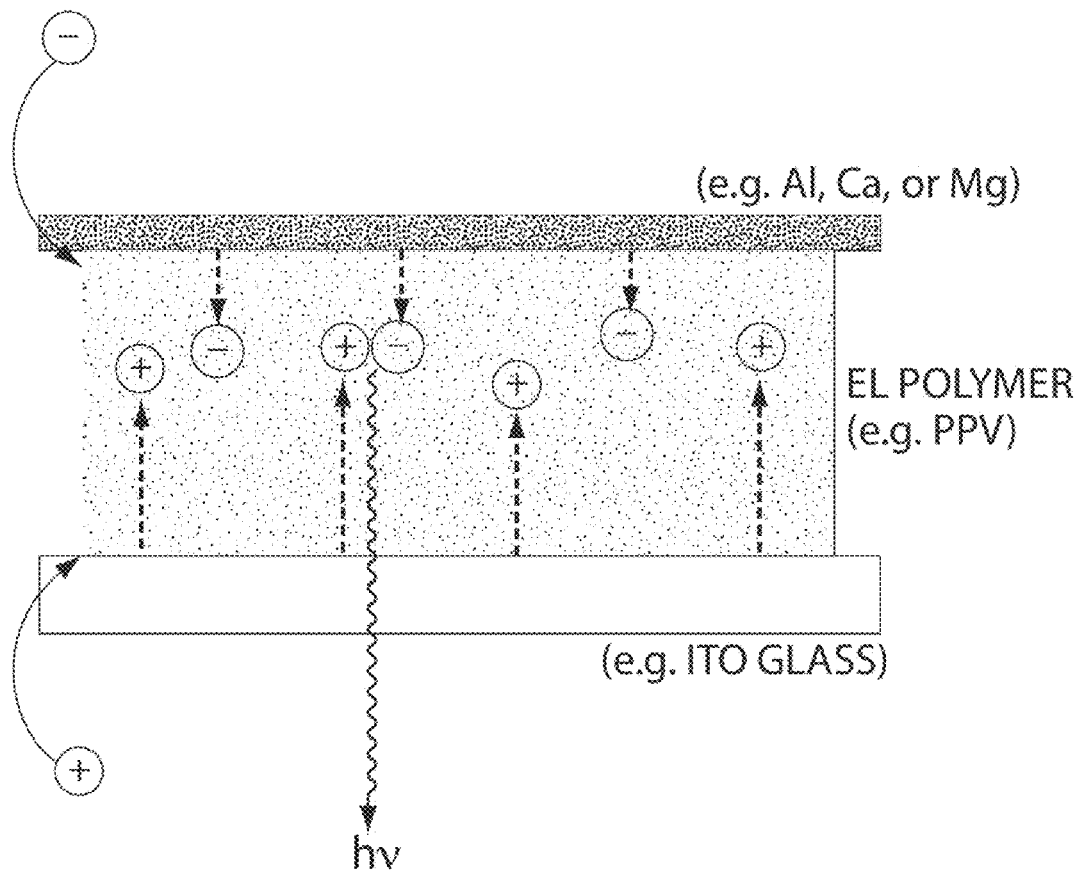
FIG. 14 is a schematic diagram of a charge transfer process in one embodiment of the invention.
Figure 15A:
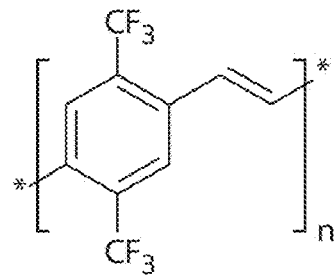
FIGS. 15A-15G illustrate various perfluorinated alkyl PPVs potentially suitable for use in certain embodiments of the invention.
Figure 15B:
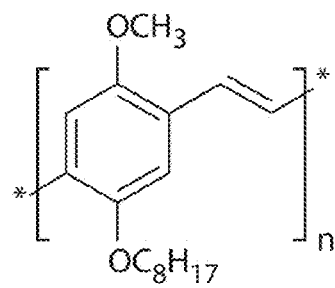
Figure 15C:
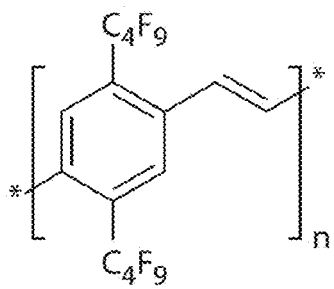
Figure 15D:
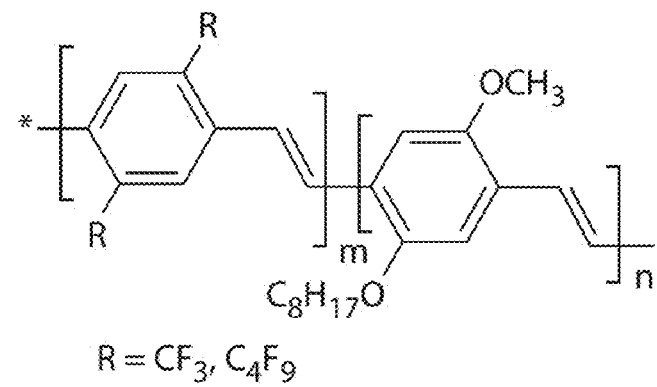
Figure 15E:
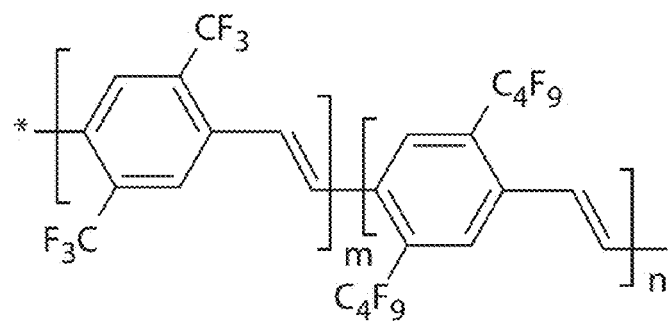
Figure 15F:
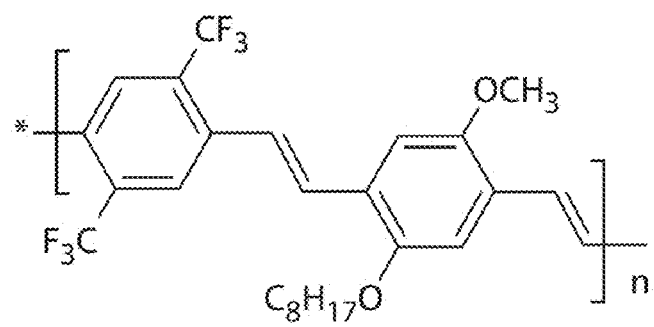
Figure 15G:
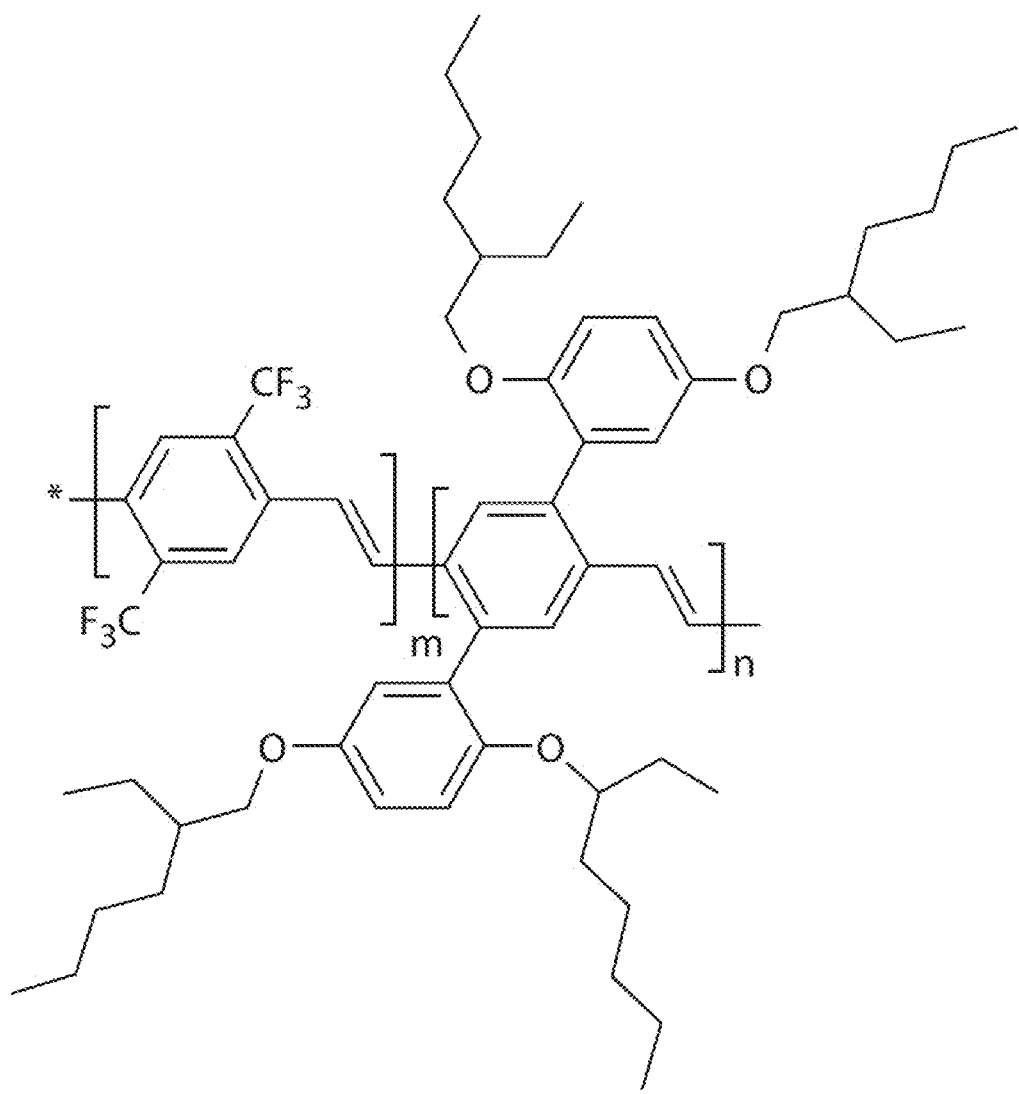
Figure 20A:
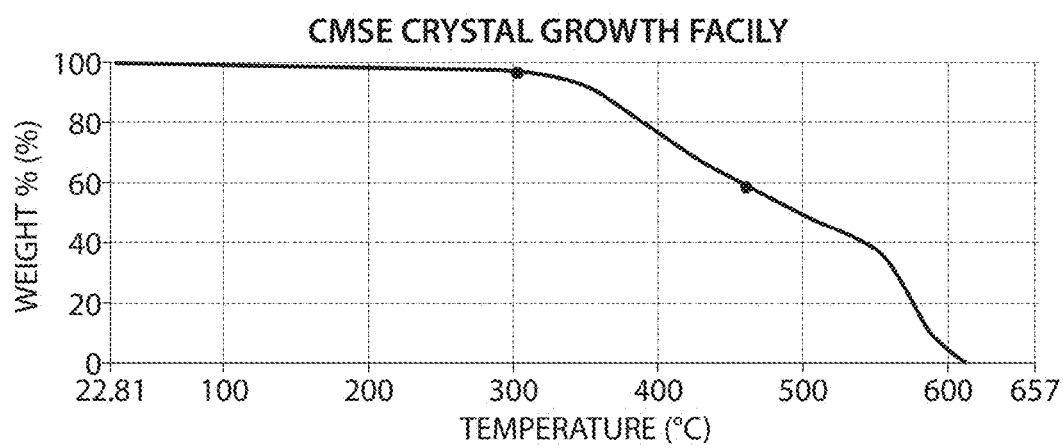
FIGS. 20A-20D illustrate the analysis of trifluoromethyl substituted PPV and MEH-PPV, according to one embodiment of the invention.
Figure 20B:
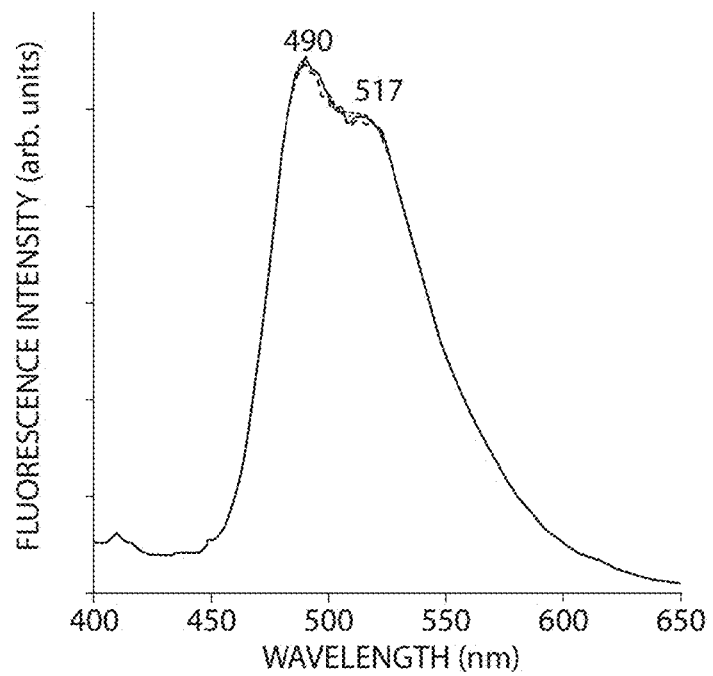
Figure 20C:
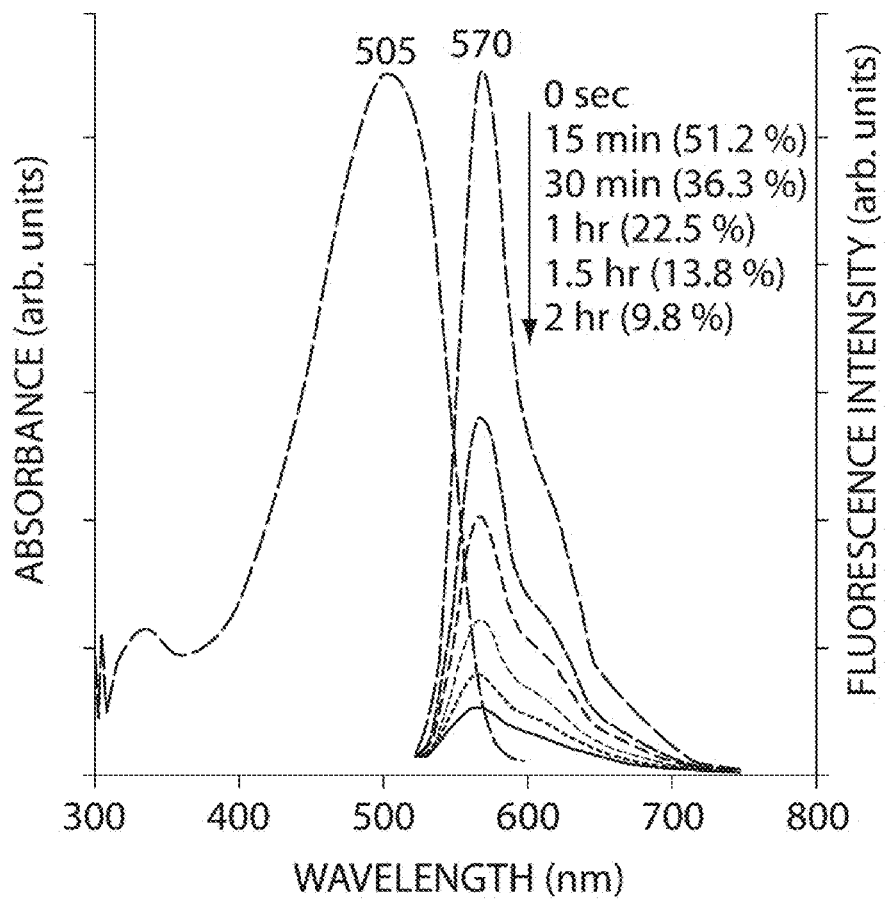
Figure 20D:
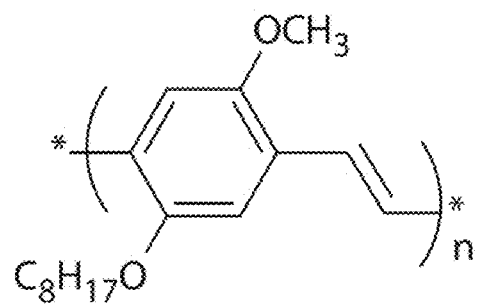

For example, photobleaching studies with UV light on trifluoromethyl containing PPV showed no change with excitation at 320 nm for 2.5 hours with slit widths of 20 nm (FIGS. 20A-20B). A schematic diagram of this process is shown in FIG. 14. FIG. 20A illustrates a thermogravimetric analysis of a trifluoromethyl substituted PPV showing no weight loss up to 300° C., and FIG. 20B illustrates the results of a photobleaching study of a trifluoromethyl substituted PPV, showing no change with excitation at 320 nm for 2.5 hours with slit widths of 20 nm. Contrastingly, the same photobleaching experiments performed on alkoxy substituted PPV (FIG. 20D) showed emissions reduced to 51.2% after just 15 min, to 36.3% after 30 min, to 22.5% after 1 hour, to 13.8% after 1.5 hours and to 9.8% after 2 hours (FIG. 20C). In these experiments, the excitation was at 320 nm and the slit width was 20 nm.

These data illustrate that certain semiconductive organic polymers may be useful in many sensors, photovoltaic, display, and electronic technologies. The performance of many electronic devices may benefit from a reduction of the contact resistance between metal electrodes and polymers. Other polymers having strongly electron withdrawing groups used in this application may also display similar stability at interfaces. In cases where electron-poor nitrogen-containing heterocyclics are present, well-defined and stable metal complexes may be formed, where nitrogen atoms can be bound to the metal ions.

EXAMPLE 10

A metal surface and a perfluorinated alkyl polymer may present a more stable interface. This greater stability may be due to the mechanism shown in FIGS. 21A and 21B, and the increased stability may be associated with sigma bonds between metals and perfluorinated alkyls. This example discusses stable interfaces of PPV comprising perfluorinated alkyls.

This increased stability may be important for certain OLEDs, also known as electric luminescence (EL) devices. OLEDs have certain advantages, such as high luminance, self-emission, low driving voltage, no limitation of view angle, and/or easy fabrication. Therefore, they can be applicable to planar displays. There are, however, still some difficulties associated with known OLEDs. These difficulties include, for example, lower efficiency of emission, limited luminance, and limited durability. An influencing factor for these problems is the efficiency of carrier injection. Since the OLED may be a light emitter having two carrier injections where electrons and holes are injected from the cathode and the anode, respectively, into the organic layers such that recombination occurs, resulting in the release of energy and the emission of light, the capability or efficiency of the electrode injections may influence the luminance and efficiency of the light emission. Therefore, it is believed that a more stable interface between the metal electrodes and certain perfluorinated alkyl polymers of the present invention may facilitate the charge injection processes and lead to more efficient light-emitting devices.

EXAMPLE 11

As with the polymers described in the previous examples, where the electron withdrawing group was bonded to the non-conjugated portion of the polymer, similar quenching characteristics may be observed with fluorescent, semiconductive polymers which have the electron withdrawing groups directly bonded to the conjugated backbone. Quenching can be observed in the presence of electron donating molecules, such as amines instead of electron deficient compounds, such as nitrated aromatic rings.

Figure 21A:
FIGS. 21A-21B illustrate certain reaction pathways potentially suitable for use in the present invention.
Figure 21B:
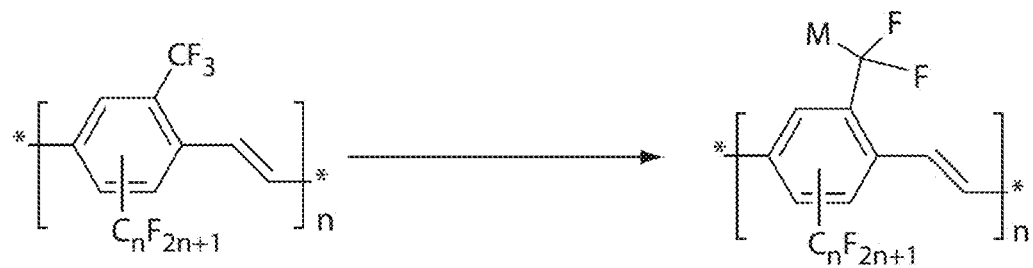
Figure 22A:
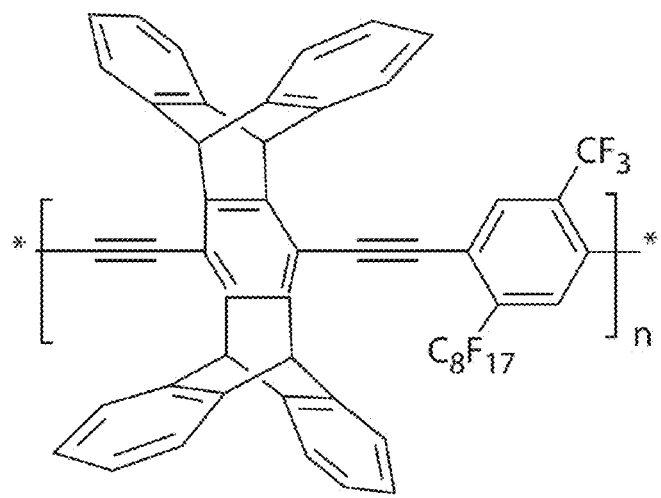
FIGS. 22A-22D illustrate certain results from indole quenching experiments on PPEs with perfluorinated alkyls bonded directly to a conjugated backbone, according to one embodiment of the invention.
Figure 22B:
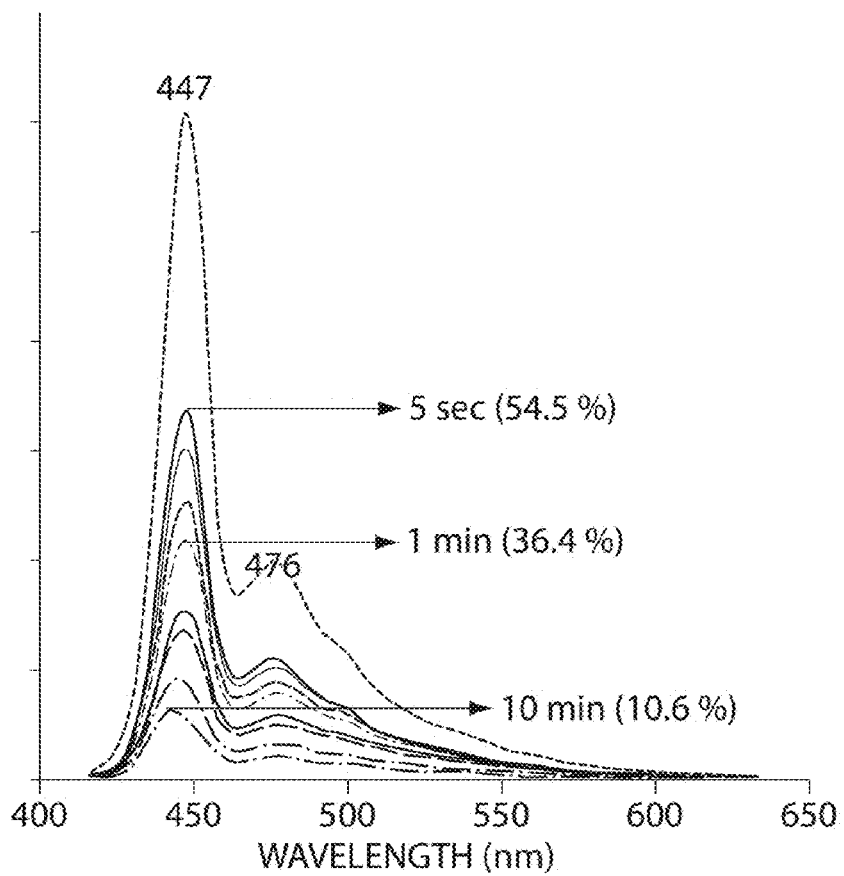
Figure 22C:
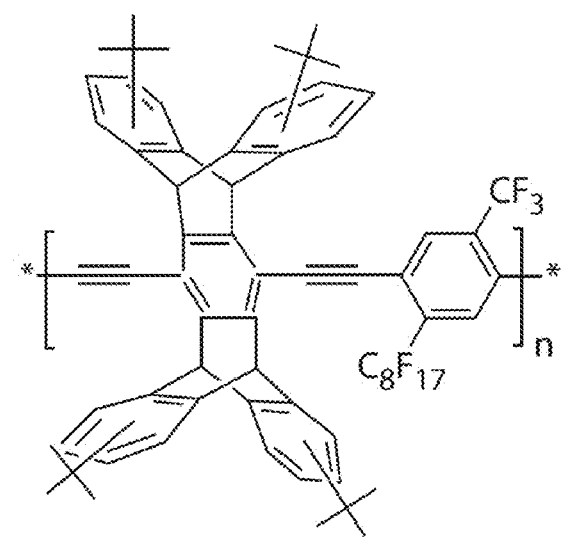
Figure 22D:
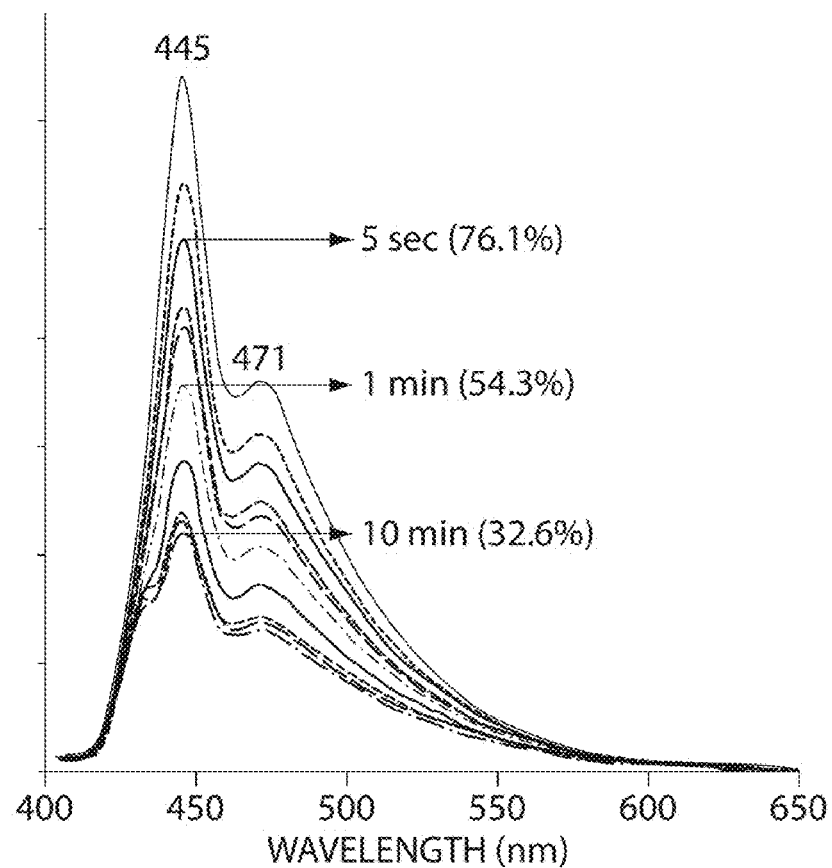

The materials described in this example may be highly quenched by indole and potentially tyrosine (see FIG. 21A). Quenching studies measuring the effect of indole on perfluorinated alkyl substituted PPE shows a reduction in fluorescence to 54.5% in 5 seconds, to 36.4% in 1 minute, and to 10.6% in 10 minutes (FIG. 21B). Interestingly, when the same set of experiments was carried out on the same perfluorinated alkyl substituted PPE, except for the presence of t-butyl groups on the non-conjugated aryls (FIG. 21C), the reduction in fluorescence was not as great. After 5 seconds, fluorescence reduced to 76.1%, after 1 minute to 54.3%, and after 10 minutes to 32.6% (FIG. 21D).

This decreased quenching effect indole has on the PPE may be due to the presence of the electron donating t-butyl groups, which may result in a more electron rich and sterically bulky system. Because the fluorescent, semiconductive polymers discussed above quench in the presence of tyrosine and indole (present in tryptophan), these polymers may be useful as a general sensor for certain proteins. Similar results may be expected from the interaction of nucleotide bases with highly electron poor polymers, thereby representing a detection technology for these analytes. The detectible signal would be the reduction in fluorescence resulting from protein induced quenching. In a broader sense, any oxidizable material could potentially be detected. The basic materials can include, for example, nerve agent stimulants, such as dimethyl-methylphosphonate (DMMP).

EXAMPLE 12

This example describes several synthesis techniques useful for preparing various polymers potentially suitable for use in the present invention. Following are general methods used in this example. NMR ($^1$H and $^{13}$C) spectra were recorded on Varian Mercury 300 MHz or Bruker Avance 400 MHz spectrometers. The chemical shift data for each signal are given in units of δ (delta) (ppm) relative to tetramethylsilane (TMS) where delta(TMS)=0, and referenced to the residual solvent. High-resolution mass spectra were obtained with a Finnigan MAT 8200 system using sector double focus and an electron impact source with an ionizing voltage of 70 V. UV-vis spectra were obtained from a Cary 50 UV-Visible Spectrophotometer. Fluorescence spectra were measured with a SPEX Fluorolog-τ3 (tau-3) fluorometer (model FL312, 450W xenon lamp) equipped with a model 1935B polarization kit. The spectra in solution were obtained at room temperature using a quartz cuvette with a path length of 1 cm. Polymer thin film spectra were recorded by front-face (22.5° detection. Fluorescence quantum yields of polymers in THF solution were determined relative equal-absorbing solutions of quinine sulfate ($\Phi_F$ (phi-F)=0.53 in 0.1 N sulfuric acid). The quantum yields for solid-state thin films were obtained relative to 0.01 mol % 9,10-diphenylanthracene in PMMA (phi-F=0.83) as a reference. The time decay of fluorescence was determined by a phase-modulation method, using frequencies from 10 to 300 MHz. The molecular weights of polymers were determined by using a PLgel 5 micron Mixed-C (300×7.5 mm) column and a diode detector at 254 nm at a flow rate of 1.0 mL/min in THF. The molecular weights were reported relative to polystyrene standards purchased from Polysciences, Inc. Polymer thin films on a cover glass (18×18 mm) were spin cast on a EC101DT photoresist spinner (Headway Research, Inc.) using a spin rate of 3000 rpm from THF solution. Melting point (m.p.) determination was performed using a Laboratory Devices MEL-TEMP instrument (open capillaries used) and was uncorrected. All solvents were spectral grade unless otherwise noted. Anhydrous THF, xylene, isopropanol, and carbon tetrachloride were purchased from Aldrich Chemical Co., Inc. All other compounds including analytes (Aldrich) were used as received. All air and water-sensitive synthetic manipulations were performed under an argon atmosphere using standard Schlenk techniques.

1,4-Dimethylanthracene (11). To a solution of 1,4-dimethylanthraquinone (1 g, 4.24 mmol) suspended in 40 mL of isopropanol was added sodium borohydride (1.6 g, 42.4 mmol) in portions over 1 h at room temperature with stirring. The reaction mixture was left to stir at this temperature for an additional 30 min before heating to reflux overnight. The solution was then cooled to room temperature and quenched by pouring into 5% HCl solution. The mixture was left to stir for 1 hr and the solution was filtered to give a yellow solid. The solid was further recrystallized from ethanol to give the product 11 as a bright yellow solid (0.795 g, 92%): m.p. 70-72° C. (lit. m.p. 74° C.); $^1$H NMR (300 MHz, CDCl$_3$): 8.56 (2 H, s), 8.06 (2 H, dd, J=6.5 and 3.3 Hz), 7.50 (2 H, dd, J=6.5 and 3.3 Hz), 7.22 (2 H, s), 2.82 (6 H, s); HR-MS (EI) calcd. for C$_{16}$H$_{14}$ (M+): 206.11, found: 206.11.

9,10-Dihydro-9,10-(1',2'-dicarbomethoxy)etheno-1,4-dimethyl anthracene (12a). To a solution of 1,4-dimethylanthracene 11 (0.55 g, 2.67 mmol) in 10 mL xylene was added dimethylacetylenedicarboxylate (1.90 g, 13.34 mmol) at room temperature and stirred at 140° C. for 24 h. The mixture was allowed to cool to room temperature and the reaction solvent was removed under vacuum to give a solid. Further purification by recrystallization from a mixture of dichloromethane and methanol (1:3) gave the product 12a as a white solid (0.84 g, 90%): m.p. 139-140° C.; $^1$H NMR (300 MHz, CDCl$_3$): 7.38 (2 H, dd, J=5.4 and 3.0 Hz), 7.03 (2 H, dd, J=5.4 and 3.0 Hz), 6.75 (2 H, s), 5.72 (2 H, s), 3.81 (6 H, s), 2.46 (6 H, s); $^{13}$C NMR (75 MHz, CDCl$_3$): 166.2, 147.3, 144.0, 142.1, 130.1, 126.8, 125.6, 124.0, 52.8, 49.6, 18.7; HR-MS (EI) calcd. for C$_{22}$H$_{20}$O$_4$ (M$^+$): 348.14, found: 348.13.

9,10-Dihydro-9,10-(1',2'-bis(trifluoromethyl))etheno-1,4-dimethyl anthracene (12b). m.p. 155-156° C.; $^1$H NMR (300 MHz, CDCl$_3$): 7.41 (2 H, dd, J=5.4 and 3.0 Hz), 7.07 (2 H, dd, J=5.4 and 3.0 Hz), 6.79 (2 H, s), 5.67 (2 H, s), 2.44 (6 H, s); $^{13}$C NMR (75 MHz, CDCl$_3$): 167.3, 143.2, 141.3, 130.3, 127.2, 126.1, 124.1, 48.1, 18.3; HR-MS (EI) calcd. for C$_{20}$H$_{14}$F$_6$ (M$^+$): 368.0994, found: 368.0995.

1,4-Bis(2-ethylhexyloxy)-5,8-dimethyl-9,10-dihydro-9,10[1',2']benzenoanthracene (12d). 1,4-dimethylanthracene (4.10 g, 19.87 mmol) and 1,4-benzoquinone (3.22 g, 29.9 mmol) were refluxed in xylenes for 40 min. Solvent was removed in vacuo and the residue were separated by flash chromatography (with polarity ramped from hexanes to 1:1 hexane:dichloromethane). The fraction containing benzenoanthracene-1,4-dione was separated, dried and redissolved in acetic acid. The solution was heated to reflux and a drop of hydrobromic acid was added. Reflux was continued for 30 min and solvent was removed under vacuum. The residue was purified by chromatography (1:10 ethyl acetate/dichloromethane) to afford 5,8-dimethyl-9,10-dihydro-9,10 [1',2']benzenoanthracene-1,4-diol (4.9 g, 79%): HR-MS (EI) calcd. for C$_{22}$H$_{18}$O$_2$ (M$^+$): 314.1307, found: 314.1313. This material was used in subsequent reactions without further characterization.

5,8-Dimethyl-9,10-dihydro-9,10[1',2']benzenoanthracene-1,4-diol (8.3 g, 26.4 mmol) was dissolved in DMF (30 mL) and sodium hydride (60% suspension in mineral oil, 4.2 g, 0.11 mol) was added in small portions. The reaction mixture was stirred for 30 min under nitrogen and 2-ethylhexyl bromide (17.8 g, 0.092 mol) was added. The reaction mixture was heated for 16 h at 100° C. and the solvent was removed. The residue was purified by column chromatography (1:10 dichloromethane/hexane) to afford the product 12d as an amorphous solid (9.90 g, 70%). $^1$H NMR (300 MHz, CDCl$_3$): 7.42 (2H, m), 7.02 (2H, m), 6.75 (2H, s), 6.50 (2H, s), 6.18 (2H, s), 3.87 (2H, s), 3.85 (2H, s), 2.53 (6H, s), 1.86 (2H, m), 1.72-1.44 (18H, m), 1.07-0.96 (12H, m); $^{13}$C NMR (75 MHz, CDCl$_3$): 148.47, 146.09, 144.04, 135.63, 135.59, 129.60, 126.12, 124.92, 123.81, 109.36, 109.25, 71.10, 44.12, 40.00, 39.93, 31.22, 31.14, 29.60, 19.45, 24.51, 24.48, 23.50, 23.46, 18.61, 18.58, 14.48, 11.74, 11.58; HR-MS (EI) calcd. for C$_{38}$H$_{50}$O$_2$ (M$^+$): 538.3811, found: 538.3824.

9,10-Dihydro-9,10-(1',2'-dicarbomethoxy)etheno-1,4-bis(bromomethyl) anthracene (13a). A mixture of the methyl ester 12a (200 mg, 0.575 mmol), N-bromosuccimide (214 mg, 1.2 mmol) and 3 mg AIBN in 5 mL carbon tetrachloride was stirred under reflux for 24 h. The mixture was cooled to room temperature and filtered to remove salts. The filtrate was washed with CCl$_4$ and the solution was evaporated to give a crude product. This was purified by column chromatography (5:1 hexane/ethyl acetate as eluent) to give 13a as a white powder (174 mg, 60%): m.p. 168-170° C.; $^1$H NMR (300 MHz, CDCl$_3$): 7.53 (2 H, dd, J=5.0 and 3.0 Hz), 7.09 (2 H, dd, J=5.0 and 3.0 Hz), 6.98 (2 H, s), 5.92 (2 H, s), 4.75 (2 H, d, J=10.2 Hz), 4.55 (2 H, d, J=10.2 Hz), 3.84 (6 H, s); $^{13}$C NMR (75 MHz, CDCl$_3$): 166.0, 147.0, 145.0, 143.0, 133.1, 126.8, 126.3, 124.8, 53.0, 49.4, 30.4; HR-MS (EI) calcd. for C$_{22}$H$_{18}$O$_4$Br$_2$ (M$^+$): 503.9566, found: 505.9524.

9,10-Dihydro-9,10-(1',2'-bis(trifluoromethyl))etheno-1,4-bis(bromomethyl)-anthracene (13b). This compound was prepared in a similar procedure as 13a, except that benzene was used as a solvent and benzoyl perodide was used as the initiator. m.p. 168-170° C.; $^1$H NMR (300 MHz, CDCl$_3$): 7.53 (2 H, dd, J=5.1 and 3.0 Hz), 7.12 (2 H, dd, J=5.1 and 3.0 Hz), 7.02 (2 H, s), 5.87 (2 H, s), 4.71 (2 H, d, J=10.5 Hz), 4.53 (2 H, d, J=10.5 Hz); $^{13}$C NMR (75 MHz, CDCl$_3$): 144.0, 142.2, 133.3, 127.3, 126.6, 124.9, 47.9, 29.6; HR-MS (EI) calcd. for C$_{20}$H$_{12}$F$_6$Br$_2$ (M$^+$): 523.92, found: 523.92.

1,4-Bis(2-ethylhexyloxy)-5,8-bis(bromomethyl)-9,10-dihydro-9,10[1',2']benzeno-anthracene (13d). Compound 12d (1.37 g, 2.54 mmol), N-bromosuccimide (0.996 g, 5.60 mmol) and benzoyl peroxide (5.0 mg) were refluxed in benzene (100 mL) for 8 h. The solvent was removed and the residue was purified by column chromatography (1:4 dichloromethane/hexane) to afford the product 13d as an amorphous solid (1.07 g, 61%): $^1$H NMR (300 MHz, CDCl$_3$): 7.48 (2H, m), 7.02 (2H, m), 6.92 (2H, s), 6.51 (2H, s), 6.31 (2H, s), 4.84 (2H, m), 4.53 (2H, m), 3.88 (4H, s), 1.82 (2H, s), 1.65-1.38 (18H, m), 1.07-0.96 (12H, m); $^{13}$C NMR (75 MHz, CDCl$_3$): 148.50, 146.54, 144.70, 134.42, 134.38, 132.36, 126.00, 125.34, 124.28, 109.88, 109.78, 71.40, 71.37, 43.89, 39.97, 39.92, 31.30, 31.28, 30.51, 29.62, 29.50, 24.61, 24.56, 23.51, 23.49, 14.52, 14.50, 11.77, 11.66; HR-MS (EI) calcd. for C$_{38}$H$_{48}$Br$_2$O$_2$: 694.2021, found: 694.2001.

Polymer 14a. Compound 13a (60 mg, 0.12 mmol) was placed in a 25 mL Schlenk flask with a stir bar. The flask was evacuated and back-filled with argon three times, followed by the addition of dry THF (3 mL). Under an atmosphere of argon, an excess of potassium t-butoxide (1 M solution in THF, 0.59 mmol) was added to the reaction solution and this was left to stir for 2 hours at room temperature. The reaction mixture was then precipitated into a mixture of methanol and water (10:1). Polymer 14a (30 mg, 73%) was collected by filtration as a yellow-orange solid: $^1$H NMR (300 MHz, CDCl$_3$): 8.0-7.8 (2 H, br), 7.7-7.4 (4 H, br), 7.2-6.9 (2 H, br), 6.4-6.1 (2 H, br), 1.6-1.4 (18 H, br); M$_n$=123 kDa, PDI=2.5.

Polymer 14b. $^1$H NMR (300 MHz, CDCl$_3$): 7.9-7.6 (6 H, br), 7.4-7.3 (2 H, br), 6.4-6.2 (2 H, br); M$_n$=684 kDa, PDI=2.5.

Polymer 14d. $^1$H NMR (300 MHz, CDCl$_3$): 7.8-6.5 (m, br, 12 H), 3.8 (br, 4 H), 1.5-0.86 (m, br, 30 H); M$_n$=890 kDa, PDI=1.7.

1,4-Bis(trifluoromethyl)-2,5-dibromobenzene (21). Into a 1000 mL round-bottomed flask were placed 250 mL trifluoroacetic acid, 1,4-bis(trifluoromethyl)benzene (19 g, 88.7 mmol), and 60 mL sulfuric acid (98%). The mixture was stirred vigorously and NBS (47.4 g, 267 mmol) was added in portions at 60° C. over a 5-hour period. After stirring at the temperature for 2 d, the mixture was poured into 500 mL of ice-water. The precipitates were filtered and sublimed to give a white solid (30 g, 91%): m.p. 64-65° C.; $^1$H NMR (300 MHz, CDCl$_3$): 8.01 (2H, s); $^{13}$C NMR (75 MHz, CDCl$_3$): 134.3, 123.4, 119.7, 119.3; $^{19}$F NMR (282 MHz, CDCl$_3$): −64.4; HR-MS (EI) calcd. for C$_8$H$_2$F$_6$Br$_2$ (M$^+$): 369.8422, found: 369.8529.

1,4-Bis(trifluoromethyl)-2,5-dibenzoic acid (22). At −75° C., precooled tetrahydrofuran (80 mL) and compound 21 (12.5 g, 33.6 mmol) dissolved in THF (60 mL) were consecutively added to n-butyllithium (2.5 M solution in hexane, 30 mL, 75 mmol). A white precipitate formed instantaneously. After 30 min of vigorous stirring at −75° C., the mixture was poured on freshly crushed dry ice. The reaction mixture was diluted with diethyl ether (150 mL) and the organic layer was extracted with 2 M NaOH (3×50 mL). The acid was collected as a white powder after acidification with 2 M HCl of the aqueous phase and recrystallized from hexane to give a white solid (7 g, 70%): m.p. >230° C.; $^1$H NMR (300 MHz, CDCl$_3$): 8.34 (2 H, s), 2.06 (2H, s); $^{13}$C NMR (75 MHz, CDCl$_3$): 165.1, 134.7, 131.8, 129.1, 124.5; $^{19}$F NMR (282 MHz, CDCl$_3$): −61.5; HR-MS (ESI) calcd. for C$_{16}$H$_{14}$ ([M−H]$^−$): 300.99, found: 300.99.

1,4-Bis(trifluoromethyl)-2,5-dihydroxymethylbenzene (23). Compound 22 (10 g, 33 mmol) was placed into Schlenk flask and followed by the addition of THF (150 mL). Into the resulting solution was added BH$_3$-THF (1 M solution in THF, 86.1 mL) dropwise at 0° C. After stirring at room temperature for 48 h, a mixture of diethyl ether (100 mL) and water (100 mL) was added to the reaction mixture. The organic layer was separated, washed with water (3×50 mL), and dried over MgSO$_4$. The solid was purified by column chromatography (5:1 hexane/ethyl acetate as eluent) to afford compound 23 as a white solid (7.1 g, 79%): $^1$H NMR (300 MHz, Acetone-d$_6$): 8.14 (2H, s), 4.87 (4H, s), 2.83 (2H, s); $^{19}$F NMR (282 MHz, Acetone-d$_6$): −62.1; HR-MS (EI) calcd. for C$_{10}$H$_8$F$_6$O$_2$ (M$^+$): 274.0423, found: 274.0412.

1,4-Bis(trifluoromethyl)-2,5-dibromomethylbenzene (24). At 0° C., PBr$_3$ (10.4 mL, 109 mmol) was slowly added to compound 23 (5 g, 18 mmol) dissolved in THF (125 mL). The reaction mixture was stirred for 30 min at 0° C. and then stirred for 40 h at room temperature. After the addition of water (20 mL) to quench the reaction under ice-bath, organic layer was diluted with diethyl ether (100 mL). The organic layer was washed with water (3×100 mL), dried over anhydrous MgSO$_4$, evaporated, and sublimed to give compound 24 as a white solid (4.6 g, 65%): m.p. 80-81° C.; $^1$H NMR (300 MHz, CDCl$_3$): 7.89 (2H, s), 4.65 (4H, s); $^{13}$C NMR (75 MHz, CDCl$_3$): 137.1, 130.8, 124.9, 121.3, 27.1; $^{19}$F NMR (282 MHz, CDCl$_3$): −61.2; HR-MS (EI) calcd. for C$_{10}$H$_6$F$_6$Br$_2$ (M$^+$): 397.8735, found: 397.8744.

1,4-Bis(trifluoromethyl)-2,5-dichloromethylbenzene (25). Tosyl chloride (3.9 g, 20.4 mmol), 4-dimethylaminopyridine (936.3 mg, 7.7 mmol), and distilled triethylamine (1.73 mL, 12.4 mmol) were added sequentially to a solution of compound 23 in dichloromethane (30 mL) under Ar at room temperature. The reaction mixture was stirred at this temperature for 4 h. The resulting solution was evaporated and the residue was diluted with hexane (100 mL). The organic layer was washed with water (3×50 mL), dried over anhydrous MgSO$_4$, evaporated, and purified by column chromatography (hexane as eluent) to give product 25 as a white solid (700 mg, 62%); $^1$H NMR (300 MHz, CDCl$_3$): 7.98 (2H, s), 4.78 (4H, s); $^{19}$F NMR (282 MHz, CDCl$_3$): −60.6; HR-MS (EI) calcd. for C$_{10}$H$_6$F$_6$Cl$_2$ (M$^+$): 309.9745, found: 309.9738.

2,5-Bis(trifluoromethyl)-1,4-xylene-bis(triphenylphosphonium bromide (26). Triphenylphosphine (730 mg, 2.75 mmol) was added to compound 24 (500 mg, 1.25 mmol) dissolved in DMF (5 mL) at room temperature. The reaction mixture was stirred and heated to reflux for 24 h. After cooling to room temperature, this solution was poured into 150 mL dried ethyl acetate. The precipitate was then filtered, washed with diethyl ether and dried in vacuo to give a white solid 26 (786 mg, 95%).

Oligomer (27). A solution of sodium ethoxide (30.6 mg, 0.45 mmol) dissolved in abs. ethanol (2 mL) was added dropwise to a solution of compound 26 (60 mg, 0.09 mmol) dissolved in chloroform (2 mL) with stirring at room temperature. 2,5-Bis(trifluoromethyl)benzaldehyde (43.9 mg, 0.18 mmol) was then added to the reaction mixture. After stirring at room temperature overnight, the reaction was quenched by the addition of water. The solvent was removed in vacuo, the residue was dissolved in dichloromethane (30 mL), and the organic layer was washed with water (3×20 mL), dried over MgSO$_4$, and concentrated in vacuo again. The crude product was purified by column chromatography (hexane as eluent) to afford compound 27 as a white solid (34 mg, 56%): $^1$H NMR (300 MHz, CDCl$_3$): 7.86 (2H, d), 7.63 (2H, d), 7.16 (4H, s), 7.13 (1H, d), 7.09 (1H, d), 7.02 (1H, d), 6.99 (1H, d); $^{19}$F NMR (282 MHz, CDCl$_3$): −61.9, −62.4, −64.5; HR-MS (EI) calcd. for C$_{28}$H$_{12}$F$_{18}$(M$^+$): 690.0646, found: 690.0670; $\lambda_{max}$ (abs, CHCl$_3$)=313 nm, $\lambda_{max}$ (emi, CHCl$_3$)=393, 413 nm.

2,5-Bis(perfluorobutyl)-p-xylene (28). A solution of C$_4$F$_9$I (0.96 mL, 5.6 mmol) was added dropwise over 10 min to a stirred mixture of 2,5-diiodo-p-xylene (0.5 g, 1.4 mmol), copper powder (1.4 g, 22.4 mmol) in DMSO (10 mL) at 130° C. The reaction mixture was subsequently stirred for a further 24 h at this temperature. After cooling to room temperature, it was poured into a beaker containing dichloromethane (30 mL) and water (30 mL). After filtering, the organic layer was separated, washed with water (3×30 mL), and dried over MgSO$_4$. The residue was purified by column chromatography (hexane as eluent) to give the product 28 as a white solid (553 mg, 73%).

2,5-Bis(perfluorobutyl)-1,4-dibromomethylbenzene (29). A mixture of compound 28 (200 mg, 0.37 mmol), N-bromosuccimide (138 mg, 0.78 mmol), and AIBN (2 mg, 0.01 mmol) in carbon tetrachloride (5 mL) was stirred under reflux for 24 h. The mixture was cooled to room temperature and filtered to remove salts. The filtrate was washed with CCl$_4$ and the solution was evaporated to give a crude product. This was purified by recrystallization from hexane to give 29 as a white solid (100 mg, 39%): $^1$H NMR (300 MHz, CDCl$_3$): 7.82 (2H, s), 4.62 (4H, s); $^{19}$F NMR (282 MHz, CDCl$_3$): −81.6, −107.6, −121.9, −125.9; HR-MS (EI) calcd. for C$_{16}$H$_6$F$_{18}$Br$_2$ ([M]$^+$): 697.85, found ([M]$^+$): 697.87.

4-(Perfluorooctyl)-α,α,α-trifluorotoluene (210). A solution of C$_8$F$_{17}$I (12 g, 22 mmol) was added dropwise over 10 min to a stirred mixture of 4-iodobenzotrifluoride (3 g, 11 mmol), copper powder (5.6 g, 0.088 mmol), 2,2'-bipyridine (120 mg, 0.8 mmol), and DMSO (30 mL) at 70° C. The reaction mixture was subsequently stirred for a further 72 h at this temperature. After cooling to room temperature, it was poured into a beaker containing ether (100 mL) and water (100 mL). After filtering, the organic layer was separated, washed with water (3×50 mL) and dried over MgSO$_4$. Sublimation gave the product 210 as a white solid (5.6 g, 90%): $^1$H NMR (300 MHz, CDCl$_3$): 7.77 (4H, dd, J=8.1 and 8.4 Hz); $^{19}$F NMR (282 MHz, CDCl$_3$): −64.0, −81.4, −111.6, −121.4, −122.0, −122.1, −122.9, −126.3.

1-Perfluorooctyl-4-trifluoromethyl-2,5-dibromobenzene (211). Into a 500 mL round-bottomed flask were placed 120 mL trifluoroacetic acid, compound 210 (12 g, 21.3 mmol), and 36 mL sulfuric acid (98%). The mixture was stirred vigorously and NBS (11.4 g, 63.8 mmol) was added in portions at 60° C. over 5-hour period. After stirring at the temperature for 2 d, the mixture was poured into 200 mL of ice-water. The precipitates were filtered and sublimed to give a white solid 211 (13.5 g, 88%): $^1$H NMR (300 MHz, CDCl$_3$): 8.04 (1H, s), 7.92 (1H, s).

1-Perfluorooctyl-4-trifluoromethyl-2,5-dibenzoic acid (212). At −75° C., precooled tetrahydrofuran (20 mL) and compound 211 (3 g, 4.16 mmol) dissolved in THF (20 mL) were consecutively added to n-butyllithium (2.5 M solution in hexane, 3.66 mL, 9.14 mmol). After stirring at −75° C. for 60 min, the mixture was poured into freshly crushed dry ice. The reaction mixture was diluted with diethyl ether (100 mL) and the organic layer was extracted with 2 M NaOH (3×30 mL). The acid was collected as a white powder after acidification with 2 M HCl of the aqueous phase and recrystallized from hexane to give a white solid 212 (1.65 g, 61%): $^1$H NMR (300 MHz, CDCl$_3$): 8.27 (1H, s), 8.26 (1H, s), 2.07 (2H, s); $^{19}$F NMR (282 MHz, CDCl$_3$): −61.5, −82.3, −106.2, −119.4, −121.5, −122.6, −123.5, −126.9.

1-Perfluorooctyl-4-trifluoromethyl-2,5-dihydroxymethylbenzene (213). Compound 212 (294 mg, 0.45 mmol) was placed into a Schlenk flask and followed by the addition of THF (5 mL). Into the resulting solution was added BH$_3$-THF (1 M solution in THF, 1.17 mL) dropwise at 0° C. After stirring at room temperature for 48 h, a mixture of diethyl ether (10 mL) and water (10 mL) was added to the reaction mixture. The organic layer was separated, washed with water (3×10 mL) and dried over MgSO$_4$. The solid was purified by column chromatography (5:1 hexane/ethyl acetate as eluant) to afford compound 213 as a white solid (284 mg, 51%): $^1$H NMR (300 MHz, Acetone-d$_6$): 8.26 (1H, s), 8.26 (1H, s), 4.92 (2H, s), 4.90 (2H, s), 2.86 (2H, s); $^{19}$F NMR (282 MHz, Acetone-d$_6$): −62.6, −82.3, −106.7, −121.5, −122.2, 122.6, −123.5, −126.9.

1-Perfluorooctyl-4-trifluoromethyl-2,5-dibromomethylbenzene (214). At 0° C., PBr$_3$ (0.24 mL, 2.54 mmol) was slowly added to compound 213 (317 mg, 0.51 mmol) dissolved in THF (10 mL). The reaction mixture was stirred for 30 min at 0° C. and then stirred for 40 h at room temperature. After the addition of water (2 mL) to quench the reaction under ice-bath, organic layer was diluted with diethyl ether (20 mL). The organic layer was washed with water (3×10 mL), dried with anhydrous MgSO$_4$, evaporated, and sublimed to give compound 214 as a white solid (240 mg, 63%): $^1$H NMR (300 MHz, CDCl$_3$): 7.90 (1H, s), 7.79 (1H, s), 4.64 (2H, s), 4.62 (2H, s); $^{19}$F NMR (282 MHz, CDCl$_3$): −61.3, −81.3, −107.1, −120.8, −121.5, 122.0, −122.9 −126.3; HR-MS (ESI) calcd. for C$_{17}$H$_6$F$_{20}$Br$_2$ ([M−H]$^−$): 746.8433, found ([M−HBr+CH$_3$]$^−$: 682.92.

2-(Perfluorodecyl)-p-xylene (215). A solution of C$_{10}$F$_{21}$I (4.2 g, 6.5 mmol) was added dropwise over 10 min to a stirred mixture of 2-bromo-p-xylene (1 g, 5.4 mmol), copper powder (1.9 g, 29.7 mmol), and DMSO (80 mL) at 130° C. The reaction mixture was subsequently stirred for a further 2 d at this temperature. After cooling to room temperature, it was poured into a beaker containing dichloromethane (50 mL) and saturated potassium iodide solution (50 mL). After filtering, the organic layer was separated, washed with water (3×30 mL), and dried over MgSO$_4$. Recrystallization from hexane gave the product 215 as a white solid (2.7 g, 82%): $^1$H NMR (300 MHz, CDCl$_3$): 7.31 (1H, s), 7.24 (1H, d, J=8.1 Hz)), 7.17 (1H, d, J=8.1 Hz)), 2.46 (3H, t, J=3.0 Hz)), 2.39 (3H, s); $^{19}$F NMR (282 MHz, CDCl$_3$): −81.4, −106.7, −121.1, −121.8, −122.0, −122.9, −126.3; HR-MS (EI) calcd. for C$_{18}$H$_9$F$_{21}$ (M$^+$): 624.0363, found: 624.0353.

2-(Perfluorodecyl)-1,4-dibromomethylbenzene (216). A mixture of compound 215 (648 mg, 1.04 mmol), N-bromosuccimide (406 mg, 2.28 mmol), and AIBN (5.1 mg, 0.03 mmol) in carbon tetrachloride (15 mL) was stirred under reflux for 24 h. The mixture was cooled to room temperature and filtered to remove salts. The filtrate was washed with CCl$_4$ and the solution was evaporated to give a crude product. This was purified by recrystallization from hexane to give 216 as a white powder (550 mg, 68%): $^1$H NMR (300 MHz, CDCl$_3$): $^{19}$F NMR (282 MHz, CDCl$_3$): −81.3, −106.5, −120.8, −121.5, −121.9, −122.9, −126.3; HR-MS (EI) calcd. for C$_{18}$H$_7$F$_{21}$Br$_2$ ([M−H]$^+$): 778.8495, found ([M−H]$^+$): 778.8518.

Poly-[2,5-bis(trifluoromethyl)-p-phenylene vinylene] (31a). Compound 24 (360 mg, 0.9 mmol) was placed in a 50 mL Schlenk flask with a stir bar. The flask was evacuated and back-filled with argon three times, followed by the addition of dry THF (15 mL). Under an atmosphere of argon, an excess of potassium t-butoxide (1 M solution in THF, 2.7 mL) was added to the reaction mixture and this was left to stir for 24 h at room temperature. The resulting solution was then poured into a mixture of methanol and water (10:1, 250 mL). The polymer (150 mg, 71%) was collected by filtration as a sparingly soluble yellow-orange solid: $^1$H NMR (300 MHz, THF-d$_6$): 8.5-8.3 (1H, br), 8.0-7.8 (1H, br), 5.7-5.5 (2H, br); M$_n$=13 kDa, PDI=1.9; $\lambda_{max}$(abs, THF)=374 nm, $\lambda_{max}$(emi, THF)=489, 519 nm.

Poly-[2,5-bis(perfluorobutyl)-p-phenylene vinylene] (31b). M$_n$=5,005, PDI=1.04; $\lambda_{max}$(abs, THF)=320 nm, $\lambda_{max}$(emi, THF)=440 nm.

Poly-[1-perfluorooctyl-4-trifluoromethyl-p-phenylene vinylene] (31c). M$_n$=3,040, PDI=1.16; $\lambda_{max}$(abs, THF)=354 nm, $\lambda_{max}$(emi, THF)=470, 496 nm.

Poly-[2-(perfluorodecyl)-p-phenylene vinylene] (31d). M$_n$=1,800, PDI=1.40; $\lambda_{max}$(abs, DMF)=378 nm, $\lambda_{max}$(emi, DMF)=488 nm.

1,1'-[2,5-Bis (trifluoromethyl)-1,4-phenylene-bis(methylene)]-bis[tetrahydrothiophenium]dibromide (217a). Tetrahydrothiophene (0.27 mL, 3 mmol) was added to a suspension of compound 24 (200 mg, 0.5 mmol) in dry methanol (5 mL). The solid was dissolved to form a clear solution within 10 min. This solution was filtered via 0.45 µm membrane filter and then heated to 50° C. with stirring for 24 h. After cooling down to room temperature, the solvent was completely removed in vacuo and cold acetone (10 mL) was added to the residue. The precipitate was then filtered and dried to give compound 217a as a colorless, hygroscopic solid (192 mg, 67%): $^1$H NMR (300 MHz, D$_2$O): 8.17 (2H, s), 4.76 (4H, s), 3.52-3.62 (8H, m), 2.34-2.47 (8H, m); $^{19}$F NMR (282 MHz, D$_2$O): −60.2; HR-MS (EI) calcd. for C$_{18}$H$_{22}$F$_6$S$_2$Br$_2$ (M$^+$): 573.94, found ([M−Br]$^+$): 495.04.

Poly[2,5-bis(trifluoromethyl)-1,4-phenylene vinylene] (218a). To a deoxygenated solution of compound 217a (267 mg, 0.46 mmol) in a mixture of water (2 mL) and methanol (1 mL) cooled in an ice bath was added dropwise an ice-cold aqueous sodium hydroxide solution (1 M, 0.46 mL) over 10 min. The reaction mixture was stirred at 0° C. for 8 h under Ar and then neutralized with 0.5 M HCl (0.5 mL). The solution was then dialyzed against water over 3 days (3×500 mL), after which the solvent was completely removed.

Polymer 31a. Thin films of polymer 31a were obtained by spin-coating the precursor polymer solution comprising 218a by thermal conversion at 200° C. and 10$^{-6}$ mbar for 5 h: $\lambda_{max}$(emi)=485, 513 nm.

1,4-Bis(trifluoromethyl)-2,5-diiodobenzene (219). To a solution of 30 mL H$_2$SO$_4$ was added periodic acid (3.18 g, 14 mmol) and potassium iodide (6.90 g, 42 mmol) under an ice bath, and then 1,4-bis(trifluoromethyl)benzene (2.17 mL, 14 mmol) was added. The reaction mixture was then stirred at 70° C. for 5 h. After cooling down to room temperature, the resulting solution was poured into ice water and then extracted with diethyl ether (100 mL) and 10% sodium thiosulfate (50 mL). The organic layer was washed with 10% sodium thiosulfate (3×50 mL), dried over MgSO$_4$, filtered, and concentrated. The residue was recrystallized from hexane to give 219 as a white solid (4.24 g, 65%): $^1$H NMR (300 MHz, CDCl$_3$): δ 8.20 (s, 2H); $^{19}$F NMR (282 MHz, CDCl$_3$): −64.2; HR-MS (EI) calcd. for C$_8$H$_2$F$_6$I$_2$ (M$^+$): 465.81, found: 465.8387.

Poly[2,5-bis(trifluoromethyl)-p-phenylene vinylene] (31a). A mixture of compound 219 (30 mg, 0.06 mmol), bis(tributylstannyl)ethylene (36.4 mg, 0.06 mmol), tri(t-butylphosphine) (0.73 mg, 0.004 mmol), tri(dibenzylideneacetone)dipalladium (0.82 mg, 0.001 mmol), and LiCl (5.1 mg, 0.12 mmol) dissolved in NMP was stirred at 80-100° C. for 48 h. The reaction mixture was cooled to room temperature and then extracted with chloroform and water. The organic layer was evaporated and the collected precipitate was washed with methanol to give sparingly soluble polymer 31a. GPC data was obtained from soluble portion in THF: M$_n$=2,650, PDI=1.05. $\lambda_{max}$(abs, CHCl$_3$)=339 nm, $\lambda_{max}$(emi, CHCl$_3$)=406, 423 nm.

2,5-Bis(trifluoromethyl)-1,4-benzenedicarboxyaldehyde (220). At −75° C., precooled tetrahydrofuran (10 mL) and compound 21 (2 g, 5.4 mmol) dissolved in THF (10 mL) were consecutively added to n-butyllithium (1.6 M solution in hexane, 7.4 mL, 11.8 mmol). A white precipitate formed instantaneously. After 30 min of vigorous stirring at −75° C., N,N-dimethylformaldehyde (3 mL, 38.8 mmol) was slowly added to the reaction mixture and then stirred for 1 h at −40° C. The dialdehyde was isolated after neutralization with 2 M HCl, ethereal extraction, and recrystallization from hexane to give a white solid 220 (539 mg, 37%): $^1$H NMR (300 MHz, CDCl$_3$): δ 10.47 (s, 2H), 8.55 (s, 2H); HR-MS (EI) calcd. for C$_{10}$H$_4$F$_6$O$_2$ (M$^+$): 270.01, found: 270.01.

2-Methoxy-5-(2'-ethylhexyloxy)-1,4-xylene-bis(triphenylphosphonium bromide (222). Triphenylphosphine (1.38 g, 5.24 mmol) was added to 1,4-bis(bromomethyl)-2((2-ethylhexyl)oxy)-5-methoxybenzene 221 (1 g, 2.38 mmol) dissolved in DMF (10 mL) at room temperature. The reaction mixture was stirred and heated to reflux for 24 h. After cooling to room temperature, this solution was poured into 300 mL dried ethyl acetate. The precipitate was then filtered, washed with diethyl ether and dried in vacuo to give a white solid 222 (1.4 g, 93%).

Poly-[(2-methoxy-5-(2'-ethylhexyloxy)-1,4-phenylene vinylene-alt-2,5-bis(trifluoro methyl)-1,4-phenylene vinylene] (32a). Into a mixture of compound 220 (10 mg, 0.037 mmol) and 222 (24.6 mg, 0.037 mmol) dissolved in chloroform (1.5 mL) was added sodium ethoxide (12.6 mg, 0.19 mmol) dissolved in ethanol (1.5 mL). The reaction mixture was stirred at room temperature overnight. The reaction was quenched with 2% HCl solution and the solution was poured into 100 mL of methanol to give orange polymer. Polymer 32a was isolated by filtration, dried, and reprecipitated in methanol: $^1$H NMR (300 MHz, CDCl$_3$): 8.05-7.75 (2 H, br), 7.55-7.20 (2 H, br), 6.96-6.55 (4 H, br), 3.85-3.65 (3 H, br), 1.45-0.45 (17 H, br); $M_n$=5,522, PDI=1.32; $\lambda_{max}$(abs, THF)=483 nm, $\lambda_{max}$(emi, THF)=531,564 nm.

1,4-Xylene-bis(diethyl)phosphonate (224). A mixture of bis(halomethyl)benzene 223 (1 g, 3.79 mmol) and triethylphosphite (1.64 g, 9.85 mmol) was heated to 130° C. for 1 to 1.5 h with distillation set-up to collect ethyl halide in situ. The temperature was increased to 160° C. under reduced pressure to distill the excess phosphite. The mixture was allowed to cool to room temperature and the product was purified by recrystallization from ether as a white solid (700 mg, 48.9%).

2-Perfluorooctyl-5-trifluoromethyl-1,4-xylene-bis(diethyl)phosphonate (225). The synthetic procedure of compound 225 generally followed that of compound 224.

Polymer 32b. A mixture of compound 220 (10 mg, 0.037 mmol) and 224 (13.99 mg, 0.037 mmol) in toluene was stirred and heated to 110° C. under Ar. A solution of potassium tert-butoxide (1 M solution in THF, 0.15 mL) was added all at once into hot mixture resulting in color change. The mixture was heated to reflux for 17 h, and then cooled down to room temperature. The resulting solution was diluted with toluene (10 mL) and 10% acetic acid (5 mL) was added. Organic layer was separated and washed with water until neutral. Water was removed from organic layer by Dean-Stark distillation to give insoluble orange solid (polymer 32b).

Polymer 32c. $M_n$=3,138, PDI=1.23; $\lambda_{max}$(abs, THF)=508 nm, $\lambda_{max}$(emi, THF)=549, 594 nm.

Polymer 33a. A solution of potassium tert-butoxide (1 M solution in THF, 0.45 mL) was added dropwise to a mixture of compound 24 (21 mg, 0.05 mmol) and compound 221 (20 mg, 0.05 mmol) in tetrahydrofuran ("TFT") (4.5 mL) at room temperature. After stirring at the temperature for 24 h, the resulting mixture was poured into methanol (125 mL). The precipitate was filtered out and reprecipitated from tetrahydrofuran/methanol to afford polymer 33a: $^1$H NMR (300 MHz, CDCl$_3$): 8.05-7.75 (2H, br); $M_n$=19 kDa, PDI=2.14; $\lambda_{max}$(abs, CHCl$_3$)=488 nm, $\lambda_{max}$(emi, CHCl$_3$)=548 nm.

Polymer 33b. $M_n$=20 kDa, PDI=8.98; $\lambda_{max}$(abs, THF)=331, 485 nm, $\lambda_{max}$(emi, THF)=440, 564 nm.

Polymer 33c. $M_n$=28 kDa, PDI=2.70; $\lambda_{max}$(abs, THF)=508 nm, $\lambda_{max}$(emi, THF)=549, 594 nm.

Polymer 33d. $M_n$=8,368, PDI=2.22; $\lambda_{max}$(abs, THF)=329 nm, $\lambda_{max}$(emi, THF)=483, 508 nm.

Polymer 33e. $\lambda_{max}$(abs, THF)=342 nm, $\lambda_{max}$(emi, THF)=449 nm.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device for detecting an analyte, comprising:
a source of a substance suspected of containing an analyte, wherein the presence and/or quantity of the analyte is unknown,
a polymer positioned to interact with the analyte, if present, wherein, upon interaction with the analyte, the polymer exhibits a change in a lasing characteristic;
an energy source able to cause the polymer to lase; and
a detector positioned to detect the change in the lasing characteristic, wherein detection of the change in the lasing characteristic is indicative of the presence and/or quantity of the analyte.

2. The device of claim 1, wherein the analyte is able to directly interact with the polymer.

3. The device of claim 1, wherein the analyte is an explosive.

4. The device of claim 1, wherein the lasing characteristic is gain.

5. The device of claim 1, wherein the lasing characteristic is a lasing threshold.

6. The device of claim 5, wherein the lasing threshold increases upon interaction of the polymer with the analyte.

7. The device of claim 1, wherein at least a portion of the polymer is conjugated.

8. The device of claim 1, wherein the polymer comprises a structure:

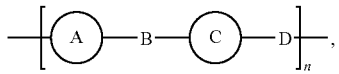

wherein n is at least 1, A and C are each aromatic, and at least one of B and D comprises a double bond or a triple bond.

9. The device of claim 1, wherein the polymer comprises a structure:

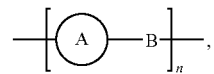

wherein n is at least 1, A is aromatic, and B comprises a double bond or a triple bond.

10. The device of claim 1, wherein the polymer has a quantum yield of at least about 50% at a wavelength of electromagnetic radiation produced by the energy source.

11. The device of claim 1, wherein the polymer can be exposed to air without substantially altering the lasing characteristic.

12. The device of claim 1, wherein the device comprises a film comprising the polymer, the film having a thickness of less than about 1 micron, the film being present on a substrate, the substrate and the polymer each having a refractive index, wherein the refractive index of the substrate is substantially equal to the refractive index of the polymer.

13. The device of claim 1, wherein the device comprises a film comprising the polymer, the film having a thickness of less than about 1 micron, the film being present on a substrate, wherein the substrate comprises a distributed feedback structure.

14. The device of claim 1, wherein the interaction comprises binding.

15. The device of claim 1, wherein the analyte is aromatic.

16. The device of claim 1, wherein the analyte is 2,4,6-trinitrotoluene or 2,4-dinitrotoluene.

17. The device of claim 1, wherein lasing of the polymer decreases upon interaction of the polymer with the analyte.

18. The device of claim 1, wherein lasing of the polymer increases upon interaction of the polymer with the analyte.

19. The device of claim 5, wherein the lasing threshold decreases upon interaction of the polymer with the analyte.

20. The device of claim 5, wherein the lasing threshold is the excitation intensity necessary to cause lasing in the polymer.

21. The device of claim 5, wherein the lasing threshold is the power necessary to cause lasing in the polymer.

22. The device of claim 1, wherein the polymer comprises triptycene.

23. The device of claim 1, wherein the device comprises a film comprising the polymer, the film having a thickness of less than about 1 micron, wherein the film is present on a fiber.

24. The device of claim 23, wherein the fiber comprises silica.

25. The device of claim 1, wherein the device comprises a film comprising the polymer, the film having a thickness of less than about 1 micron, wherein the film is present on a substrate.

26. The device of claim 25, wherein the substrate is substantially planar.

27. The device of claim 25, wherein the substrate comprises parylene.

28. The device of claim 25, wherein the substrate and the polymer together form a waveguide.

29. The device of claim 25, wherein the substrate is substantially optically transparent.

* * * * *